United States Patent
Ham et al.

(10) Patent No.: US 10,280,154 B2
(45) Date of Patent: May 7, 2019

(54) PYRIMIDINE COMPOUND AND PHARMACEUTICAL USE THEREOF

(71) Applicant: HANMI PHARM. CO., LTD., Hwaseong-si, Gyeonggi-do (KR)

(72) Inventors: Young Jin Ham, Hwaseong-si (KR); Seok Jong Kang, Hwaseong-si (KR); Jae Yul Choi, Hwaseong-si (KR); Seo Hee Kim, Hwaseong-si (KR); Tae Woo Kim, Hwaseong-si (KR); In Hwan Bae, Hwaseong-si (KR); Young Gil Ahn, Hwaseong-si (KR); Kwee Hyun Suh, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 16/127,487

(22) Filed: Sep. 11, 2018

(65) Prior Publication Data
US 2019/0031643 A1    Jan. 31, 2019

Related U.S. Application Data

(63) Continuation of application No. PCT/KR2018/001193, filed on Jan. 26, 2018.

(30) Foreign Application Priority Data

Jan. 26, 2017 (KR) .................. 10-2017-0012766

(51) Int. Cl.
| | | |
|---|---|---|
| *C07D 403/14* | (2006.01) | |
| *A61P 35/00* | (2006.01) | |
| *C07D 401/14* | (2006.01) | |
| *C07D 403/04* | (2006.01) | |

(52) U.S. Cl.
CPC ............ *C07D 403/14* (2013.01); *A61P 35/00* (2018.01); *C07D 401/14* (2013.01); *C07D 403/04* (2013.01)

(58) Field of Classification Search
CPC .. C07D 403/13; C07D 401/14; C07D 403/04; A61P 35/00
USPC .................................................... 514/210.2
See application file for complete search history.

(56) References Cited

U.S. PATENT DOCUMENTS

| | | | |
|---|---|---|---|
| 8,461,170 B2 * | 6/2013 | Aquila | ............... C07F 9/65685 514/275 |
| 2009/0318446 A1 | 12/2009 | Fischer et al. | |
| 2011/0015173 A1 | 1/2011 | Florjancic et al. | |
| 2011/0183975 A1 | 7/2011 | Goto et al. | |

FOREIGN PATENT DOCUMENTS

| | | |
|---|---|---|
| WO | 2014/155300 A2 | 10/2014 |
| WO | 2015/154039 A2 | 10/2015 |
| WO | 2016029839 A1 | 3/2016 |
| WO | 2018134213 A1 | 7/2018 |

OTHER PUBLICATIONS

Irena Melnikova et al., "Targeting protein kinases", Nature Reviews Drug Discovery, Dec. 2004, 2 pages, col. 3.
Stefanie Kliche et al., "VEGF Receptor Signaling and Endothelial Function", IUBMB Life, 2001, 6 pages, vol. 51.
Michael Simons et al., "Mechanisms and regulation of endothelial VEGF receptor signalling", Nature Reviews Molecular Cell Biology, Oct. 2016, 15 pages, vol. 17.
Xiaoliang Wu et al., "AXL kinase as a novel target for cancer therapy", Oncotarget, Oct. 16, 2014, 18 pages, vol. 5, No. 20.
Juliano D. Paccez et al., "The receptor tyrosine kinase Axl in cancer: biological functions and therapeutic implications", International Journal of Cancer, 2014, 39 pages, vol. 134.
Xianglan Sun et al., :"The regulation and function of the NUAK family", Journal of Molecular Endocrinology, 2013, 9 pages, vol. 51.
Shinsuke Araki et al., "Inhibitors of CLK Protein Kinases Suppress Cell Growth and Induce Apoptosis by Modulating Pre-mRNA Splicing", PLOS One, Jan. 12, 2015, 18 pages, vol. 10.
International Search Report for PCT/KR2018/001193 dated May 2, 2018.
Australian Patent Office; Communication dated Sep. 5, 2018 in counterpart application No. 2018211880.

* cited by examiner

*Primary Examiner* — Yevgeny Valenrod
(74) *Attorney, Agent, or Firm* — Sughrue Mion, PLLC

(57) ABSTRACT

Provided are a pyrimidine compound represented by Formula 1, a method of preparing the same, and a pharmaceutical use of the pyrimidine compound for the prevention or treatment of cancer.

18 Claims, No Drawings

PYRIMIDINE COMPOUND AND PHARMACEUTICAL USE THEREOF

This application is a bypass continuation application of PCT Application No. PCT/KR2018/001193, filed Jan. 26, 2018, and claiming the benefit of priority from Korean Patent Application No. 10-2017-0012766, filed Jan. 26, 2017.

TECHNICAL FIELD

The present invention is related to a novel pyrimidine compound, a method of preparing the same, and a pharmaceutical use of the novel pyrimidine compound.

PRIOR ART

Kinases mediate a reaction in which a phosphate group from high-energy molecules, in particular, ATP, is transferred to a substrate. Kinases stabilize phosphoric anhydride bonds, and locate the substrate and the phosphate group at a specific position to increase a reaction rate. In most cases, the transition state resulting from the interaction with a phosphate group having a negative charge is electrostatically stabilized through surrounding amino acids having a positive charge, and some kinases may be coordinated with the phosphate group through a metal cofactor.

Kinases can be classified as, for example, protein kinases, lipid kinases, and carbohydrate kinases, according to the substrate and characteristics. Proteins, lipids, or carbohydrates may vary in their activity, reactivity, ability to bind to other molecules, etc., depending on the phosphorylation state. Kinases affect intracellular signal transduction and regulate complex biological mechanisms within cells. Due to phosphorylation, some molecules may have enhanced or reduced activities, and their ability to interact with other molecules may be controlled. Because many kinases respond to environmental conditions or signals, cells may control intracellular molecules through kinases, depending on the situation. As such, kinase plays a crucial role in cell growth, differentiation, proliferation, survival, metabolism, signal transduction, cell transport, secretion, and many other cellular reaction pathways.

Kinases have been found in a variety of species including bacteria, fungi, insects, and mammals, and 500 or more kinases have been found in humans to date.

Protein kinases may increase or decrease the activity of a protein, become a marker for stabilization or degradation, place a protein in a specific cell compartment, or initiate or disturb interactions of a protein with other proteins. Protein kinases are known to account for the majority of kinases and are considered to be an important research target. Protein kinases regulate, together with phosphatase, proteins and enzymes as well as cell signal transduction. Although cell proteins are subject to numerous covalent bonds, there are not many of these reversible bonds, such as phosphorylation. Accordingly, it can be said that phosphorylation of proteins has a regulatory function. Protein kinases may often have multiple substrates, and sometimes, a particular protein may act as a substrate for at least one kinase. For this reason, protein kinases are named using factors that regulate their activities. For example, a calmodulin-dependent protein kinase is regulated by calmodulin. In some cases, kinases may be classified as sub-groups. For example, type I and type II cyclic AMP-dependent protein kinases include identical enzyme subunits, but their regulatory subunits binding to cyclic AMP are different from each other.

A protein kinase is an enzyme that catalyzes the phosphorylation of the hydroxy group located in tyrosine, serine, and threonine residues of proteins and plays an important role in signaling growth factors that induce cell growth, differentiation, and proliferation (Melnikova, I. et al., Nature Reviews Drug Discovery, 3 (2004), 993), and it is reported that abnormal expression or mutation of a specific kinase frequently occurs in cancer cells.

One of the ways that cells recognize external stimuli is recognition via tyrosine kinase, which is a receptor in the cell membrane. A receptor tyrosine kinase (RTK) consists of an extracellular part exposed to the outside of a cell, an intracellular part exposed to the intracellular cytoplasm, and a transmembrane part passing through the plasma membrane between the extracellular part and the intracellular part. The extracellular part of the receptor is the part to which a specific ligand binds, and the intracellular part functions to transmit the activation signal of the receptor activated by the ligand into the cell. The RTK has a domain having tyrosine kinase activity at the C-terminal region exposed in the cell, and when a specific ligand attaches to the extracellular part, the kinase enzyme of the C-terminal tyrosine kinase domain exposed to the cytoplasmic portion of the receptor protein is activated, and the two RTKs cross-phosphorylate the tyrosines at the C-terminals of the neighboring RTKs. This phosphorylation process of tyrosine is the most important process in the transmission of signals corresponding to extracellular stimulation into cells. There are many known receptors that have tyrosine kinase activities for transmitting extracellular stimuli into cells with this mechanism. Examples of such receptors are SRC, EGFR, IR, IGFR, c-fms, VEGFR, FGFR, AXL, CLK2, and NUAK1.

Among these, vascular endothelial growth factor receptor (VEGFR) refers to a kinase known to be involved in the regulation of angiogenesis. In particular, solid tumors require more nutrients and oxygen than normal tissues. Therefore, compared to normal states, the blood supply is an important factor when blood is insufficient. Also, overexpression or overactivation of VEGFR induces angiogenesis, which plays an important role in angiogenesis necessary for the growth and proliferation of tumor cells (Kliche, S. and Waltenberger, J., Life, 52, (2002), 61). Therefore, various clinical studies for the treatment of tumors through inhibition of angiogenesis have been performed, and several promising results have been obtained. In addition, VEGF plays an important role in blood cancer and is overexpressed in various malignant solid tumors. The overexpression of VEGF is known to have a high correlation with disease progression of malignant tumors. VEGFRs are classified according to subtypes including VEGFR-1, VEGFR-2, and VEGFR-3. VEGFR-2 (KDR) is a typical target for tumor diseases having VEGFR expression. Representative diseases caused by the overexpression of VEGFR-2 is lung cancer, breast cancer, non-Hodgkin's lymphoma, ovarian carcinoma, pancreatic cancer, etc. In addition to its angiogenic activity, VEGF, which is a ligand of VEGFR, may promote tumor growth by a direct pro-survival effect in tumor cells (Simons, M., Gordon, E. and Claesson-Welsh, L., Nature Reviews Drug Discovery, 17, (2016), 611).

Tyrosine-protein kinase receptor UFO (AXL) kinase refers to a kinase that functions to transfer signals of extracellular substrates to the cytoplasm by binding growth factors such as vitamin K-dependent protein growth regulating gene 6 (GAS6) (Wu, X., et al., Oncotarget, 5, (2014), 9546). In addition, AXL kinase is heavily involved in cell proliferation and survival. AXL may mediate cell aggregation by homologous binding. AXL protein is expressed in bone marrow stroma, bone marrow cells, tumor cells, and tumor vasculature. In tumor cells, AXL is expressed not only in immune cells including dendritic cells, macrophages and NK cells, but also in tumor cells. AXL is a component in a variety of cellular processes that plays a crucial role in the development, growth, and spread of tumors, including proliferation, invasion and migration, epithelial-mesenchymal transition, stemness, angiogenesis, and immune modulation, is associated with oncogenes, and is associated with the survival and proliferation of various tumors including triple-negative breast cancer (TNBC), blood cancer, non-small cell lung cancer (NSCLC), pancreatic cancer, and ovarian cancer (Paccez, J. et al., Int. J. Cancer, 134, (2014), 1024).

Recent research results show that NUAK1 kinase, also known as AMPK-related protein kinase 5 (ARK5), plays an important role in regulating tumor growth and survival through metabolic changes in various carcinomas, in particular, hepatocellular carcinoma. Regarding the physiological and pathological role of NUAK in tumor and metabolic diseases, NUAK is known to act as an important regulator of cellular physiological activities such as cell polarity and cell motility, and through interaction with a kinase associated with AMP-activated protein kinase (AMPK), NUAK maintains homeostasis for tumor growth and proliferation. Thus, a key strategy against anticancer and related diseases may be to inhibit the attainment of energy homeostasis in tumors (Sun, X et al., J Mol Endocrinol, 51, (2013), R15).

Dual specificity protein kinase (CLK2) interacts with and phosphorylates a serine/arginine (SR) protein of a spliceosomal complex. The interaction and phosphorylation are part of regulatory mechanisms that allow the SR proteins to regulate RNA splicing. This protein kinase is involved as a regulator in growth processes for various tumor cells and acts as a link among cell cycle progression, apoptosis, and telomere length regulation (Araki, S., PLoS ONE, 10, (2015), e0116929).

PRIOR ART DOCUMENT

1. Melnikova, I. et al., Nature Reviews Drug Discovery, 3, (2004), 993
2. Kliche, S. et al., Life, 52, (2002), 61
3. Simons, M. et al., Nature Reviews Drug Discovery, 17, (2016), 611
4. Wu, X., et al., Oncotarget, 5, (2014), 9546
5. Paccez, J. et al., Int. J. Cancer, 134, (2014), 1024
6. Sun, X et al., J Mol Endocrinol, 51, (2013), R15
7. Araki, S., PLoS ONE, 10, (2015), e0116929

DISCLOSURE OF THE INVENTION

Technical Goal of the Invention

In accordance with an aspect of the present invention, provided is a novel pyrimidine compound having kinase inhibitory activity.

In accordance with another aspect of the present invention, provided is a method of preparing the pyrimidine compound.

In accordance with still another aspect of the present invention, provided is a pharmaceutical use of the pyrimidine compound.

Means for Achieving Technical Goal

In accordance with an aspect of the present invention, provided is a compound selected from a substance of Formula 1, a stereoisomer thereof, a tautomer thereof, a solvate thereof, and a pharmaceutically acceptable salt thereof:

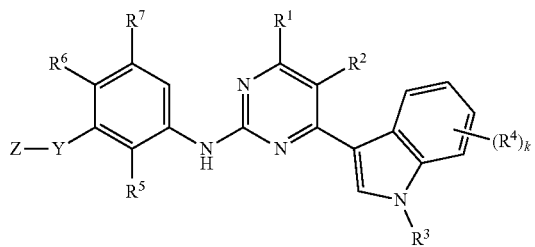

Formula 1 wherein, in Formula 1,
$R^1$ is hydrogen, a halogen, a hydroxy group, or a $C_{1-4}$ alkoxy group,
$R^2$ is hydrogen, a halogen, a cyano group, a nitro group, an amino group, a carboxamide group, a formyl group, a halo $C_{1-4}$ alkyl group, or a $C_{1-4}$ alkyl group,
$R^3$ is hydrogen, a halo $C_{1-4}$ alkyl group, a $C_{1-4}$ alkyl group, a $C_{2-4}$ alkenyl group, or a $C_{2-4}$ alkynyl group,
$R^4$(s) are each independently a halogen, a hydroxy group, a cyano group, a nitro group, an amino group, —$SR_c$, —S(=O)$R_c$, —S(=O)$_2R_c$, a halo $C_{1-4}$ alkyl group, a $C_{1-4}$ alkoxy group, a hydroxy $C_{1-4}$ alkyl group, a $C_{1-4}$ alkyl group, a $C_{2-4}$ alkenyl group, a $C_{2-4}$ alkynyl group, —$NR_aR_b$, —$CO_2R_b$, or —CO—$NR_aR_b$,
wherein, $R_a$ and $R_b$ are each independently hydrogen or a $C_{1-6}$ alkyl group, and
$R_c$ is a $C_{1-4}$ alkyl group or —$NR_aR_b$,
k is an integer from 0 to 4,
$R^5$ and $R^6$ are each independently hydrogen, a halogen, a hydroxy group, a nitro group, an amino group, a $C_{1-4}$ alkoxy group, a hydroxy $C_{1-4}$ alkyl group, a $C_{1-4}$ alkyl group, a $C_{2-4}$ alkenyl group, a $C_{2-4}$ alkynyl group, a $C_{3-10}$ cycloalkyl group, or a $C_{3-9}$ heterocycloalkyl group,
wherein, the $C_{3-10}$ cycloalkyl group and the $C_{3-9}$ heterocycloalkyl group are each independently unsubstituted or substituted with a halogen, a $C_{1-4}$ alkyl group, a halo $C_{1-4}$ alkyl group,
$R^7$ is hydrogen, a linear or branched $C_{1-6}$ alkyl group, a $C_{3-7}$ cycloalkyl group, a $C_{3-9}$ heterocycloalkyl group, or a $C_{1-4}$ alkoxy group,
Y is a direct bond, —(CH$_2$)$_m$—, —O—, —O(CH$_2$)$_m$—, —(CH$_2$)$_m$O—, —C(=O)—, —NR$^9$—, —SO$_2$—, —(CH$_2$)$_m$—O—(CH$_2$)$_n$—, —CO(CH$_2$)$_m$—, —(CH$_2$)$_m$CO—, —(CH$_2$)$_m$—CO—(CH$_2$)$_n$—, —(CH$_2$)$_m$NR$^9$—, —NR$^9$(CH$_2$)$_m$—, —(CH$_2$)$_m$—NR$^9$—(CH$_2$)$_n$—, —(CH$_2$)$_m$SO$_2$—, —SO$_2$(CH$_2$)$_m$—, or —(CH$_2$)$_m$—SO$_2$—(CH$_2$)$_n$—,
wherein R$^9$ is hydrogen, a $C_{1-4}$ alkyl group, a $C_{3-10}$ cycloalkyl group, or a $C_{3-9}$ heterocycloalkyl group, and
m and n are each independently an integer from 1 to 3,
Z is represented by Formula 2:

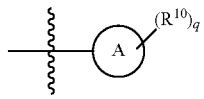

Formula 2 wherein, in Formula 2,
Ⓐ is a $C_{3-10}$ cycloalkyl group or a $C_{2-11}$ heterocycloalkyl group, R$^{10}$(s) are each independently a halogen, a hydroxy group, a cyano group, a nitro group, an amino group, a thiol group, a formyl group, a linear or branched halo C$_{1-4}$ alkyl group, a linear or branched C$_{1-4}$ alkoxy group, a linear or branched hydroxy C$_{1-4}$ alkyl group, a linear or branched C$_{1-4}$ alkyl group, a linear or branched hydroxy C$_{1-4}$ alkylcarbonyl group, a C$_{2-4}$ alkenyl group, a C$_{2-4}$ alkynyl group, a C$_{3-10}$ cycloalkyl group, a C$_{2-9}$ heterocycloalkyl group, a hydroxy C$_{2-9}$ heterocycloalkyl group, —NR$^{11}$R$^{12}$, —COR$^{13}$, —COOR$^{13}$, or —SO$_2$R$^{14}$, R$^{11}$ and R$^{12}$ are each independently hydrogen, a linear or branched hydroxy C$_{1-4}$ alkyl group, a linear or branched halo C$_{1-4}$ alkyl group, a linear or branched C$_{1-4}$ alkyl group, a C$_{2-4}$ alkenyl group, or a C$_{2-4}$ alkynyl group, R$^{13}$ is hydrogen, a hydroxy group, a hydroxy C$_{1-4}$ alkyl group, a halo C$_{1-4}$ alkyl group, a C$_{1-4}$ alkyl group, a C$_{2-4}$ alkenyl group, a C$_{2-4}$ alkynyl group, a C$_{3-10}$ cycloalkyl group, or a C$_{2-9}$ heterocycloalkyl group, R$^{14}$ is a hydroxyl group, a halo C$_{1-4}$ alkyl group, a C$_{1-4}$ alkyl group, a C$_{2-4}$ alkenyl group, a C$_{2-4}$ alkynyl group, a C$_{3-10}$ cycloalkyl group, a C$_{2-9}$ heterocycloalkyl group, an aryl group, or —NR$_a$R$_b$, and q is an integer from 0 to 5.

In accordance with another aspect of the present invention, provided is a pharmaceutical compound for prevention and treatment of cancer that may include the compound of Formula 1 as an active ingredient.

Effect of the Invention

Because the compound of Formula 1 according to an aspect of the present invention has kinase inhibitory activity, the compound may be applicable to inhibition of kinase.

DESCRIPTION OF EMBODIMENT

The present invention will be described in further detail.

Unless otherwise defined, all terms (including technical and scientific terms) used herein have the same meaning as commonly understood by one of ordinary skill in the art to which this invention belongs. Although exemplary methods or materials are listed herein, other similar or equivalent ones are also within the scope of the present invention. Also, the numerical values set forth herein are considered to include the meaning of "about" unless explicitly stated. All publications disclosed as references herein are incorporated in their entirety by reference.

In Formula 1, residues described as R$^1$ to R$^{15}$ are each used in the meaning as commonly understood by one of ordinary skill in the art.

The term "halogen", unless otherwise stated, include fluorine, chlorine, bromine, or iodine, in particular, fluorine or chlorine.

The term "alkyl" refers to a saturated monovalent hydrocarbon radical. The term "alkenyl" as used herein refers to a monovalent hydrocarbon radical containing at least one carbon-carbon double bond, wherein each double bond may have a steric configuration of E-form or Z-form. The term "alkynyl" as used herein refers to a monovalent hydrocarbon radical containing at least one carbon-carbon triple bond. Such an alkyl group, an alkenyl group, and an alkynyl group may be linear, i.e., straight-chained or branched having a side chain. As defined above, the number of carbon atoms in an alkyl group may be 1, 2, 3, 4, 5, or 6; or 1, 2, 3, or 4.

Examples of alkyl include methyl, ethyl, propyl including n-propyl and iso-propyl, n-butyl, sec-butyl, butyl including iso-butyl and a tert-butyl, pentyl including n-pentyl, 1-methylbutyl, iso-pentyl, neo-pentyl, and tert-pentyl, hexyl including n-hexyl, 3,3-dimethylbutyl, and iso-hexyl. A double bond of an alkenyl group and a triple bond of an alkynyl group may each be in any position. Examples of alkenyl and alkynyl include ethenyl, prop-1-enyl, prop-2-enyl(=allyl), but-2-enyl, 2-methylprop-2-enyl, 3-methylbut-2-enyl, hex-3-enyl, hex-4-enyl, prop-2-ynyl(=propargyl), but-2-ynyl, but-3-ynyl, hex-4-ynyl, or hex-5-ynyl. In a case where each of the compounds is sufficiently stable and suitable for a desirable use as, for example, a pharmaceutical substance, a substituted alkyl group, a substituted alkenyl group, and a substituted alkynyl group may be substituted at any position.

The term "cycloalkyl", unless otherwise stated, refers to a substituted or unsubstituted cyclic alkyl, e.g., mono- or bicycloaliphatic group. Examples of cycloalkyl include cyclopropyl, cyclobutyl, cyclopentyl, cyclohexyl, cyclohexenyl, cycloheptyl, cycloheptenyl, cyclooctyl, cyclooctenyl, 2,5-cyclohexadienyl, bicyclo[2.2.2]octyl, adamant-1-yl, decahydronaphthyl group, oxo cyclohexyl, dioxo cyclohexyl, thio cyclohexyl, 2-oxo bicyclo[2.2.1]hept-1-yl, or any suitable isomer thereof without limitation.

The term "heterocycloalkyl" as used herein, unless otherwise stated, refers to a single ring including at least one selected from O, N, and S, in particular, 1 to 4 heteroatoms, or cyclicalkyl, which may be substituted or unsubstituted, having at least two rings. Examples of monoheterocycloalkyl include piperidinyl, morpholinyl, thiamorpholinyl, pyrrolidinyl, imidazolidinyl, tetrahydrofuranyl, diazabicycloheptanyl, diazabicyclooctanyl, diazaspirooctanyl, and the like, but examples thereof are not limited thereto.

The term "aryl" as used herein, unless otherwise stated, refers to an aromatic group which may be substituted or unsubstituted, such as phenyl, biphenyl, naphthyl, toluyl, naphthalenyl, anthracenyl, or any suitable isomer thereof without limitation.

The term "heteroaryl" as used herein, unless otherwise stated, refers to a monocyclic or bicyclic or higher aromatic group containing at least one heteroatom selected from O, N, and S, for example, from 1 to 4 heteroatoms. Examples of monocyclic heteroaryl include thiazolyl, oxazolyl, thiophenyl, furanyl, pyrrolyl, imidazolyl, isoxazolyl, pyrazolyl, triazolyl, thiadiazolyl, tetrazolyl, oxadiazolyl, pyridinyl, pyridazinyl, pyrimidinyl, pyrazinyl, and the like, but examples thereof are not limited thereto. Examples of bicyclic heteroaryl include indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, purinyl, furopyridinyl, and the like, but examples thereof are not limited thereto.

In the present specification, the numerical range indicated by using the term "to" refers to a range including the numerical values described before and after the term as the lower limit and the upper limit, respectively.

In an example embodiment of an aspect of the present invention, R$^1$ in the compound of Formula 1 may be hydrogen, a C$_{1-4}$ alkoxy group or a hydroxy group.

In an example embodiment, R$^2$ in the compound of Formula 1 may be hydrogen, halogen, a C$_{1-4}$ alkyl group or a halo C$_{1-4}$ alkyl group.

In an example embodiment, R$^3$ in the compound of Formula 1 may be hydrogen.

In an example embodiment, R$^4$ in the compound of Formula 1 may be hydrogen, halogen, a hydroxy group, a C$_{1-4}$ alkoxy group, a hydroxy C$_{1-4}$ alkyl group or a C$_{1-4}$ alkyl group.

In an example embodiment, $R^5$ and $R^6$ in the compound of Formula 1 may each independently be hydrogen or a hydroxy group.

In an example embodiment, $R^7$ in the compound of Formula 1 may be a $C_{3-7}$ cycloalkyl group.

In an example embodiment, Y in the compound of Formula 1 may be —$(CH_2)_m$—, —$(CH_2)_m$—O—$(CH_2)_n$—, or —$(CH_2)_m$—CO—$(CH_2)_n$—, wherein m and n may each independently be an integer selected from 1 and 2.

In an example embodiment, Z in the compound of Formula 1 may be represented by Formula 2.

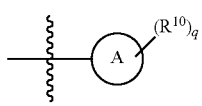

Formula 2 wherein, in Formula 2,
Ⓐ may be a $C_{3-6}$ heterocycloalkyl group including one or two heteroatoms selected from O, N, and S,
$R^{10}$(s) may each independently be hydrogen, a hydroxy group, a linear or branched hydroxy $C_{1-4}$ alkyl group, a linear or branched $C_{1-4}$ alkyl group, a $C_{3-10}$ cycloalkyl group, a $C_{2-9}$ heterocycloalkyl group, a hydroxy $C_{2-9}$ heterocycloalkyl group, —$NR^{11}R^{12}$, or —$COR^{13}$,
$R^{11}$ and $R^{12}$ may each independently be hydrogen, a linear or branched hydroxy $C_{1-4}$ alkyl group or a linear or branched $C_{1-4}$ alkyl group,
$R^{13}$ may be hydrogen, a hydroxy group, a linear or branched hydroxy $C_{1-4}$ alkyl group, a linear or branched halo $C_{1-4}$ alkyl group, or a linear or branched $C_{1-4}$ alkyl group, and
q may each independently be an integer from 0 to 5.

In an example embodiment, in the compound of Formula 1,
$R^1$ may be hydrogen, a hydroxy group, a $C_{1-4}$ alkoxy group or a $C_{1-4}$ alkyl group,
$R^2$ may be hydrogen, halogen, a $C_{1-4}$ alkyl group or a halo $C_{1-4}$ alkyl group,
$R^3$ may be hydrogen,
$R^4$ may be hydrogen, halogen, a hydroxy group, a $C_{1-4}$ alkoxy group, a hydroxy $C_{1-4}$ alkyl group, or a $C_{1-4}$ alkyl group,
k may be an integer from 0 to 2,
$R^5$ and $R^6$ may each independently be hydrogen or a hydroxy group,
$R^7$ may be a cyclopropyl group,
Y may be a direct bond, —$(CH_2)_m$—, —O—, —C(=O)—, —$(CH_2)_m$—O—$(CH_2)_n$—, or —$(CH_2)_m$—CO—$(CH_2)_n$—,
Z may be represented by Formula 2,

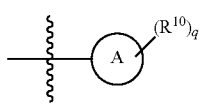

Formula 2 wherein, in Formula 2,
Ⓐ may be a $C_{3-6}$ heterocycloalkyl group including one or two heteroatoms selected from O, N, and S,
$R^{10}$(s) may each independently be a hydroxy group, a hydroxy $C_{1-4}$ alkyl group, a $C_{1-4}$ alkyl group, a $C_{3-10}$ cycloalkyl group, a $C_{2-9}$ heterocycloalkyl group, a hydroxy $C_{2-9}$ heterocycloalkyl group, —$NR^{11}R^{12}$, or —$COR^{13}$,
$R^{11}$ and $R^{12}$ may each independently be hydrogen, a hydroxy $C_{1-4}$ alkyl group or a $C_{1-4}$ alkyl group,
$R^{13}$ may be hydrogen, a hydroxy $C_{1-4}$ alkyl group, a halo $C_{1-4}$ alkyl group, or a $C_{1-4}$ alkyl group, and
q may each independently be an integer from 0 to 3.

In an example embodiment, in the compound of Formula 1,
$R^1$, $R^3$, $R^5$, and $R^6$ may each be hydrogen,
$R^2$ may be hydrogen or halogen,
$R^4$ may be a $C_{1-4}$ alkyl group or halogen,
$R^7$ may be hydrogen, a linear or branched $C_{1-6}$ alkyl group, a $C_{3-7}$ cycloalkyl group, or a $C_{1-4}$ alkoxy group,
Y may be a direct bond, —$CH_2$—, —O—, ethyleneoxy, or —C(=O)—, and
Z may be any one selected from Formulae 3 to 5:

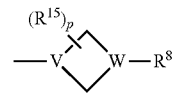

Formula 3

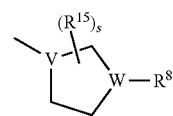

Formula 4

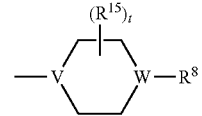

Formula 5 wherein, in Formulae 3 to 5,
V and W may each independently be N or a CH, provided that at least one of V and W is not CH,
$R^8$ may be selected from the group consisting of hydrogen, halogen, a linear or branched $C_{1-4}$ alkyl group, a linear or branched hydroxy $C_{1-4}$ alkyl group, a hydroxy group, —$NR^{11}R^{12}$, a linear or branched hydroxy $C_{1-4}$ alkylcarbonyl group, a heterocycloalkyl group, a hydroxy substituted heterocycloalkyl group, a linear or branched halo $C_{1-4}$ alkyl group, and a linear or branched $C_{1-4}$ alkoxy group,
$R^{11}$ and $R^{12}$ may each independently be a hydrogen, a linear or branched $C_{1-4}$ alkyl group, or a linear or branched hydroxy $C_{1-4}$ alkyl group,
$R^{15}$ may each independently be a linear or branched $C_{1-4}$ alkyl group, a linear or branched hydroxy $C_{1-4}$ alkyl group, or halogen,
p may be an integer from 0 to 4, and
s and t may each independently be an integer from 0 to 5, provided that $R^8$ is hydrogen, or an an integer from 0 to 4, provided that $R^8$ is not hydrogen.

In particular, in the compound of Formula 1,
$R^7$ may be hydrogen or a $C_{3-7}$ cycloalkyl group,
Y may be a direct bond or —$CH_2$—,
Z may be Formula 4 or Formula 5,
$R^8$ may be hydrogen, a linear or branched $C_{1-4}$ alkyl group, a linear or branched hydroxy $C_{1-4}$ alkyl group, a heterocycloalkyl group or a hydroxy substituted heterocycloalkyl group, and
$R^{15}$ may each independently be a linear or branched $C_{1-4}$ alkyl group, a linear or branched hydroxy $C_{1-4}$ alkyl group, or halogen.

In an example embodiment, the compound of Formula 1 may be selected from the group consisting of compounds shown in Table 1:

TABLE 1

| No. | Compound |
|---|---|
| 1 | 2-(4-(3-((5-chloro-4-(6-fluoro-1H-indole-3-yl)pyrimidine-2-yl)amino)-5-cyclopropylphenyl)piperazine-1-yl)ethane-1-ol |
| 2 | 2-(4-(3-((5-chloro-4-(6-methyl-1H-indole-3-yl)pyrimidine-2yl)amino)-5-cyclopropylphenyl)piperazine-1-yl)ethane-1-ol |
| 3 | 5-chloro-N-(3-cyclopropyl-5-(4-(dimethylamino)piperidine-1-yl)phenyl)-4-(1H-indole-3-yl)pyrimidine-2-amine |
| 4 | (S)-1-((1-(3-((5-chloro-4-(1H-indole-3-yl)pyrimidine-2-yl)amino)-5-cyclopropylphenyl)piperidine-4-yl)(methyl)amino)propane-2-ol |
| 5 | (S)-1-((1-(3-((5-chloro-4-(6-methyl-1H-indole-3-yl)pyrimidine-2-yl)amino)-5-cyclopropylphenyl)piperidine-4-yl)(methyl)amino)propane-2-ol |
| 6 | 5-chloro-N-(3-cyclopropyl-5-(4-(dimethylamino)piperidine-1-yl)phenyl)-4-(6-methyl-1H-indole-3-yl)pyrimidine-2-amine |
| 7 | 2-(4-(3-((5-chloro-4-(6-methoxy-1H-indole-3-yl)pyrimidine-2-yl)amino)-5-cyclopropylphenyl)piperazine-1-yl)ethane-1-ol |
| 8 | (S)-1-(1-(3-((5-chloro-4-(1H-indole-3-yl)pyrimidine-2-yl)amino)-5-cyclopropylphenyl)piperidine-4-yl)pyrrolidine-3-ol |
| 9 | (S)-1-(1-(3-((5-chloro-4-(6-methyl-1H-indole-3-yl)pyrimidine-2-yl)amino)-5-cyclopropylphenyl)piperidine-4-yl)pyrrolidine-3-ol |
| 10 | 5-chloro-N-(3-cyclopropyl-5-(4-(dimethylamino)piperidine-1-yl)phenyl)-4-(6-methoxy-1H-indole-3-yl)pyrimidine-2-amine |
| 11 | (S)-1-(1-(3-((5-chloro-4-(6-methoxy-1H-indole-3-yl)pyrimidine-2-yl)amino)-5-cyclopropylphenyl)piperidine-4-yl)pyrrolidine-3-ol |
| 12 | 2-(4-(3-((4-(1H-indole-3-yl)-5-methylpyrimidine-2-yl)amino)-5-cyclopropylphenyl)piperazine-1-yl)ethane-1-ol |
| 13 | 5-chloro-N-(3-cyclopropyl-5-(4-morpholinopiperidine-1-yl)phenyl)-4-(6-methyl-1H-indole-3-yl)pyrimidine-2-amine |
| 14 | 5-chloro-N-(3-cyclopropyl-5-(4-(ethyl(methyl)amino)piperidine-1-yl)phenyl)-4-(6-methyl-1H-indole-3-yl)pyrimidine-2-amine |
| 15 | 5-chloro-N-(3-cyclopropyl-5-(4-(diethylamino)piperidine-1-yl)phenyl)-4-(6-methyl-1H-indole-3-yl)pyrimidine-2-amine |
| 16 | 5-chloro-N-(3-cyclopropyl-5-(3-(dimethylamino)pyrrolidine-1-yl)phenyl)-4-(6-methyl-1H-indole-3-yl)pyrimidine-2-amine |
| 17 | 2-(4-(3-((5-chloro-4-(6-methyl-1H-indole-3-yl)pyrimidine-2-yl)amino)-5-cyclopropylphenyl)piperazine-1-yl)-2-methylpropane-1-ol |
| 18 | N-(3-(4-aminopiperidine-1-yl)-5-cyclopropylphenyl)-5-chloro-4-(6-methyl-1H-indole-3-yl)pyrimidine-2-amine |
| 19 | 5-chloro-N-(3-cyclopropyl-5-(4-(methylamino)piperidine-1-yl)phenyl)-4-(6-methyl-1H-indole-3-yl)pyrimidine-2-amine |
| 20 | 2-(4-(3-((5-chloro-4-(6-fluoro-1H-indole-3-yl)pyrimidine-2-yl)amino)-5-cyclopropylphenyl)piperazine-1-yl)-2-methylpropane-1-ol |
| 21 | 2-(4-(3-((5-chloro-4-(6-methyl-1H-indole-3-yl)pyrimidine-2-yl)amino)-5-cyclopropylphenyl)piperidine-1-yl)ethane-1-ol |
| 22 | 2-(4-(3-((5-chloro-4-(6-chloro-1H-indole-3-yl)pyrimidine-2-yl)amino)-5-cyclopropylphenyl)piperazine-1-yl)ethane-1-ol |
| 23 | 5-chloro-N-(3-cyclopropyl-5-(4-(pyrrolidine-1-yl)piperidine-1-yl)phenyl)-4-(6-methyl-1H-indole-3-yl)pyrimidine-2-amine |
| 24 | 1-(1-(3-((5-chloro-4-(6-methyl-1H-indole-3-yl)pyrimidine-2-yl)amino)-5-cyclopropylphenyl)piperidine-4-yl)azetidine-3-ol |
| 25 | 2-(4-(3-((5-chloro-4-(1H-indole-3-yl)pyrimidine-2-yl)amino)-5-methoxyphenyl)piperazine-1-yl)ethane-1-ol |
| 26 | 2-(4-(3-((5-chloro-4-(6-fluoro-1H-indole-3-yl)pyrimidine-2-yl)amino)phenyl)piperazine-1-yl)ethane-1-ol |
| 27 | 2-(4-(3-((5-chloro-4-(1H-indole-3-yl)pyrimidine-2-yl)amino)phenyl)piperidine-1-yl)ethane-1-ol |
| 28 | 2-(4-(3-((5-chloro-4-(1H-indole-3-yl)pyrimidine-2-yl)amino)phenyl)piperazine-1-yl)ethane-1-ol |
| 29 | 5-chloro-N-(3-(4-(dimethylamino)piperidine-1-yl)phenyl)-4-(1H-indole-3-yl)pyrimidine-2-amine |
| 30 | 5-chloro-N-(3-(3-(dimethylamino)pyrrolidine-1-yl)phenyl)-4-(1H-indole-3-yl)pyrimidine-2-amine |
| 31 | 2-(4-(3-((5-chloro-4-(6-fluoro-1H-indole-3-yl)pyrimidine-2-yl)amino)-5-methoxyphenyl)piperazine-1-yl)ethane-1-ol |
| 32 | 2-(4-(3-((5-chloro-4-(1H-indole-3-yl)pyrimidine-2-yl)amino)-5-isopropoxyphenyl)piperazine-1-yl)ethane-1-ol |
| 33 | 2-(4-(3-((5-chloro-4-(6-fluoro-1H-indole-3-yl)pyrimidine-2-yl)amino)-5-isopropoxyphenyl)piperazine-1-yl)ethane-1-ol |
| 34 | 5-chloro-N-(3-cyclopropyl-5-(piperazine-1-ylmethyl)phenyl)-4-(6-fluoro-1H-indole-3-yl)pyrimidine-2-amine |
| 35 | 2-(4-(3-((5-chloro-4-(6-fluoro-1H-indole-3-yl)pyrimidine-2-yl)amino)-5-methoxybenzyl)piperazine-1-yl)ethane-1-ol |
| 36 | 2-(4-(3-((5-chloro-4-(6-fluoro-1H-indole-3-yl)pyrimidine-2-yl)amino)benzyl)piperazine-1-yl)ethane-1-ol |

TABLE 1-continued

| No. | Compound |
|---|---|
| 37 | 2-(4-(3-((5-chloro-4-(1H-indole-3-yl)pyrimidine-2-yl)amino)-5-methoxybenzyl)piperazine-1-yl)ethane-1-ol |
| 38 | 2-(4-(3-((5-chloro-4-(1H-indole-3-yl)pyrimidine-2-yl)amino)-5-cyclopropylbenzyl)piperazine-1-yl)-2-methylpropane-1-ol |
| 39 | (S)-1-((1-(3-((5-chloro-4-(1H-indole-3-yl)pyrimidine-2-yl)amino)-5-cyclopropylbenzyl)piperidine-4-yl)(methyl)amino)propane-2-ol |
| 40 | (S)-1-((1-(3-((5-chloro-4-(6-methyl-1H-indole-3-yl)pyrimidine-2-yl)amino)-5-cyclopropylbenzyl)piperidine-4-yl)(methyl)amino)propane-2-ol |
| 41 | 2-(4-(3-((5-chloro-4-(6-methyl-1H-indole-3-yl)pyrimidine-2-yl)amino)-5-cyclopropylbenzyl)piperazine-1-yl)-2-methylpropane-1-ol |
| 42 | (S)-1-(1-(3-((5-chloro-4-(1H-indole-3-yl)pyrimidine-2-yl)amino)-5-cyclopropylbenzyl)piperidine-4-yl)pyrrolidine-3-ol |
| 43 | (S)-1-(1-(3-((5-chloro-4-(6-methyl-1H-indole-3-yl)pyrimidine-2-yl)amino)-5-cyclopropylbenzyl)piperidine-4-yl)pyrrolidine-3-ol |
| 44 | (S)-1-(1-(3-((5-chloro-4-(6-methoxy-1H-indole-3-yl)pyrimidine-2-yl)amino)-5-cyclopropylbenzyl)piperidine-4-yl)pyrrolidine-3-ol |
| 45 | 1-(3-((5-chloro-4-(6-methyl-1H-indole-3-yl)pyrimidine-2-yl)amino)-5-cyclopropylbenzyl)piperidine-4-ol |
| 46 | (S)-5-chloro-N-(3-cyclopropyl-5-((3-(dimethylamino)pyrrolidine-1-yl)methyl)phenyl)-4-(6-methyl-1H-indole-3-yl)pyrimidine-2-amine |
| 47 | 1-(4-(3-((5-chloro-4-(6-fluoro-1H-indole-3-yl)pyrimidine-2-yl)amino)-5-cyclopropylbenzyl)piperazine-1-yl)-2-hydroxyethane-1-one |
| 48 | 1-(4-(3-((5-chloro-4-(6-methyl-1H-indole-3-yl)pyrimidine-2-yl)amino)-5-cyclopropylbenzyl)piperazine-1-yl)-2-hydroxyethane-1-one |
| 49 | 2-(4-(3-((5-chloro-4-(6-ethyl-1H-indole-3-yl)pyrimidine-2-yl)amino)-5-cyclopropylbenzyl)piperazine-1-yl)ethane-1-ol |
| 50 | (3-((5-chloro-4-(1H-indole-3-yl)pyrimidine-2-yl)amino)-5-methoxyphenyl)(4-(2-hydroxyethyl)piperazine-1-yl)methanone |
| 51 | 1-(2-(3-((5-chloro-4-(6-methyl-1H-indole-3-yl)pyrimidine-2-yl)amino)-5-cyclopropylphenoxy)ethyl)piperidine-4-ol |
| 52 | 1-(2-(3-((5-chloro-4-(6-methyl-1H-indole-3-yl)pyrimidine-2-yl)amino-5-ethylphenoxy)ethyl)piperidine-4-ol |
| 53 | (R)-2-(3-(3-((5-chloro-4-(6-methyl-1H-indole-3-yl)pyrimidine-2-yl)amino)-5-cyclopropylphenoxy)pyrrolidine-1-yl)ethane-1-ol |
| 54 | 2-(4-(3-((5-chloro-4-(6-methyl-1H-indole-3-yl)pyrimidine-2-yl)amino)-5-cyclopropylphenoxy)piperidine-1-yl)ethane-1-ol |
| 55 | 2-(4-(3-((5-chloro-4-(1H-indole-3-yl)pyrimidine-2-yl)amino)-5-methoxyphenoxy)piperidine-1-yl)ethane-1-ol |

The term "optical isomer" as used herein refers to various stereoisomers and geometrical isomers for the compound according to the present invention. Since the compounds of formula 1 may have an asymmetric carbon center (asymmetric carbon), the compounds of formula 1 according to an aspect of the present invention may be in form of an enantiomer (R or S isomer), racemate, diastereomer, or any mixture thereof. All these isomers and mixtures are included within the scope of the present invention. The optically active (R)- and (S)-isomers may be resolved using conventional techniques or can be prepared using chiral synthon or chiral reagents. When a compound includes a double bond, a substituent may be in an E form or an Z form. When a compound includes a cycloalkyl group that has two substituents, the compound may be in a cis-form or a trans-form. In addition, when the compound of Formula 1 includes a bridged ring, the compound may be in a form of an exo-isomer or an endo isomer. The compound of Formula 1 may include all tautomers.

In accordance with an aspect, the compound of Formula 1 and an optical isomer thereof may be in a form of a solvate. The term "solvate" may include a molecular complex including the compound and at least one pharmaceutically acceptable solvent molecule, e.g., ethanol or water. A complex, in which the solvent molecule is water, is also referred to as "hydrate".

In accordance with an aspect, the compound of Formula 1, an optical isomer thereof, and a solvate thereof may be in a form of a pharmaceutically acceptable salt. The term "pharmaceutically acceptable salt" as used herein refers to a salt that are low in toxicity to humans and do not adversely affect the biological activity and physicochemical properties of the parent compound. A pharmaceutically acceptable salt may include acid addition salts of a pharmaceutically acceptable free acid and a base compound of Formula 1, alkali metal salts (such as sodium salts) and alkaline earth metal salts (such as calcium salts), organic base addition salts of an organic base group and a carboxylic acid structure of Formula 1, amino acid addition salts, and the like, but are embodiments not limited thereto.

The pharmaceutically acceptable salt may be prepared by a conventional method. For example, the compound of Formula 1 may be dissolved in a solvent, which may be mixed with water, e.g., methanol, ethanol, acetone, 1,4-dioxane, and then a free acid or a free base may be added thereto for crystallization to thereby prepare a pharmaceutically acceptable salt.

In accordance with another aspect of the present invention, provided is a method of preparing the compound of Formula 1 including reacting a compound of Formula 6 with a compound of Formula 7:

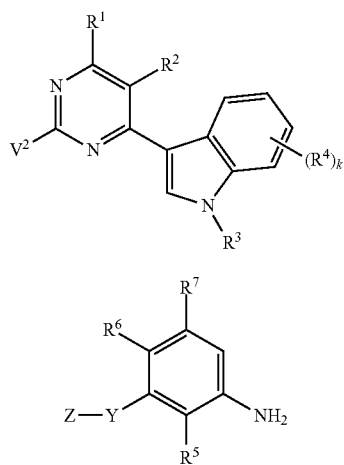

Formula 6

Formula 7 wherein, in Formulae 6 and 7, $R^1$, $R^2$, $R^3$, $R^4$, $R^5$, $R^6$, $R^7$, Y, Z, and k may respectively be defined the same as those of Formulae 1 and 2, and $V^2$ may be halogen.

An organic base, e.g., triethylamine, diisopropylethylamine, pyridine, and the like; an inorganic base, e.g., sodium carbonate, potassium carbonate, hydrogenated sodium, and the like; an organic acid, e.g., trifluoroacetic acid, toluenesulfonic acid, and the like; or an inorganic acid, e.g., hydrochloric acid, sulfuric acid, phosphoric acid, and the like, may or may not be added to a reaction solution when performing the reaction. A solvent used in the reaction may be any solvent that does not inhibit the reaction, for example, a polar aprotic solvent such as dimethylsulfoxide, N, N-dimethylformamide, acetonitrile, or tetrahydrofuran (THF); a polar protic solvent such as methanol, ethanol, 2-propanol, or 2-butanol; or a nonpolar aprotic solvent such as toluene or 1,4-dioxane. A reaction temperature may be in a range of 0° C. to 15° C., for example, from room temperature to about 100° C.

The compounds of Formulae 6 and 7 may be prepared using conventional knowledge in the field of organic chemistry.

In an example embodiment, the compound of Formula 1 may be prepared as shown in Reaction Scheme 1:

Reaction Scheme 1

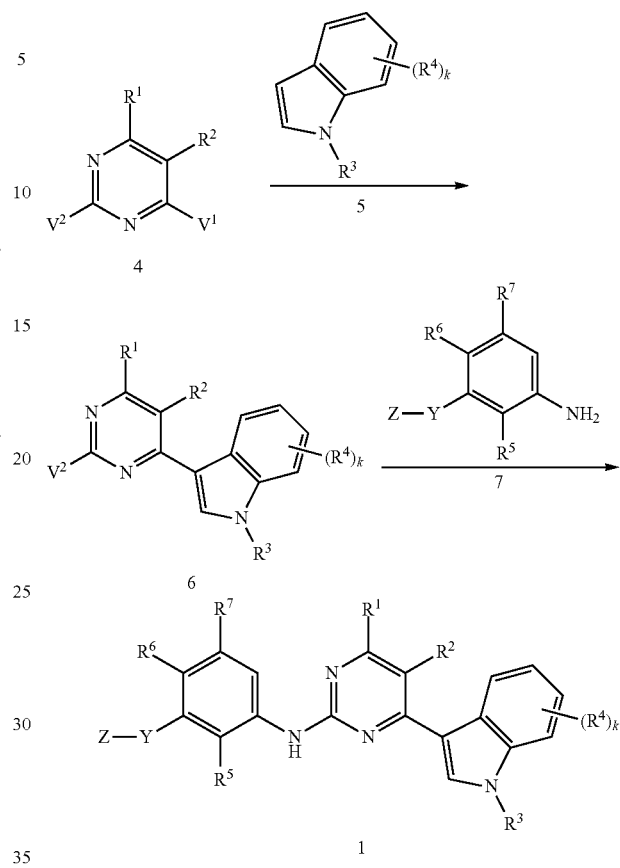

wherein, in Reaction Scheme 1, $R^1$, $R^2$, $R^3$, $R^4$, $R^6$, $R^7$, Y, Z, and k may respectively be defined the same as those of Formulae 1 and 2, and $V^1$ and $V^2$ may each independently be halogen.

In preparing the compound of Formula 6 by reacting the compound of Formula 4 with the compound of Formula 5, the reaction may be performed by adding an organometallic compound. For example, the organometallic compound may be an alkyl magnesium compound or an alkyl lithium compound.

A solvent used in the reacting may be any solvent that does not inhibit the reaction, for example, a polar aprotic solvent such as dimethylsulfoxide, N, N-dimethylformamide, acetonitrile, or THF; or a nonpolar aprotic solvent such as toluene or 1,4-dioxane. A reaction temperature may be in a range of 0° C. to 100° C. for example, from 0° C. to 60° C.

In preparing the compound of Formula 7, in a case where Y is —$(CH_2)_m$—, m may each independently be 0 and 1, in a case where Y is —$(CH_2)_m$—O—$(CH_2)_n$—, m may be 0, and n may each independently be 0 and 2, in a case where Y is —$(CH_2)_m$—CO—$(CH_2)_n$—, m and n may each be 0, and the compound of Formula 7 may be prepared using conventional knowledge in the field of organic chemistry, as shown in Preparation Schemes 1 to 3:

Preparation Scheme 1 in case where Y is ——(CH$_2$)$_m$——;

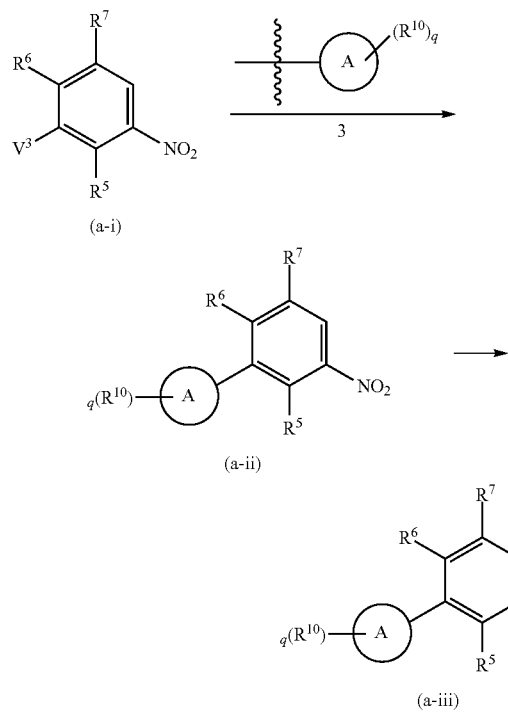

m = 0,

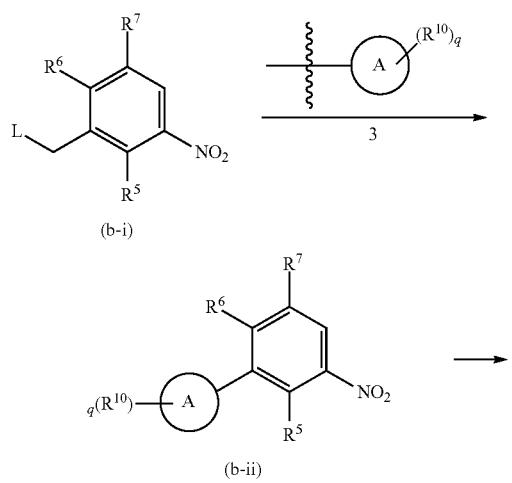

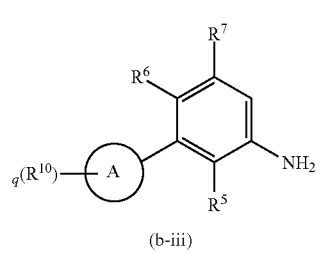

m = 1,

Preparation Scheme 2 in case where Y is ——(CH$_2$)$_m$——O——(CH$_2$)$_n$——;

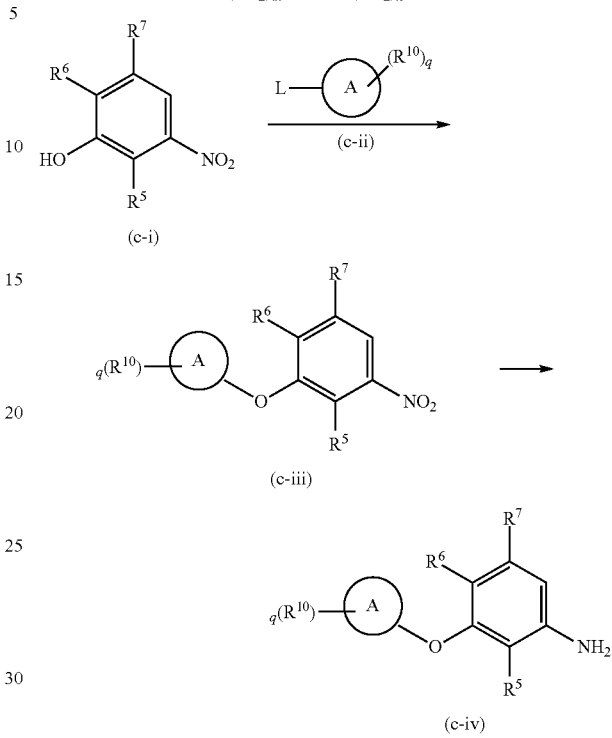

n = 0,

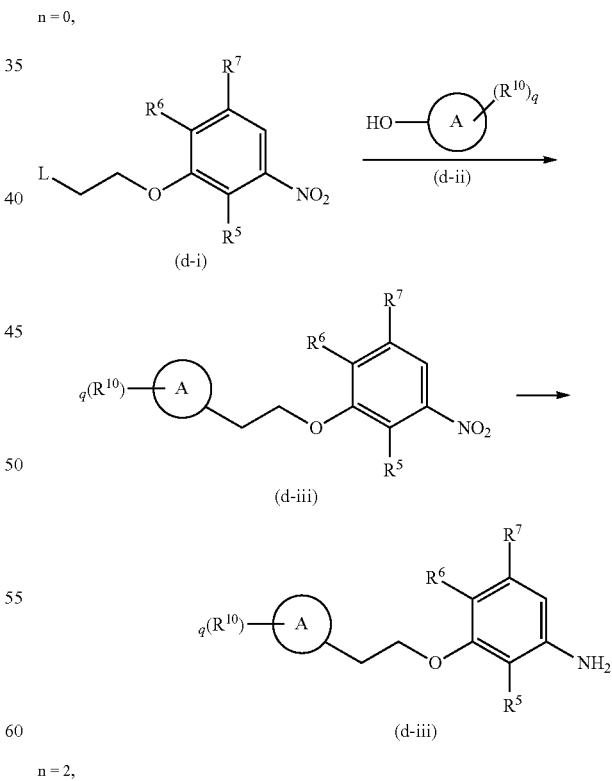

n = 2, wherein, in Preparation Scheme 1, R$^5$, R$^6$, R$^7$, R$^{10}$, Ⓐ, and q may respectively be defined the same as those of Formulae 1 and 3, V$^3$ may be halogen, and L may be Cl, Br, I, OMs, OTs, or the like, wherein, in Preparation Scheme 2, R$^6$, R$^7$, R$^{10}$, Ⓐ, and q may respectively be defined the same as those of Formulae 1 and 3, and L may be Cl, Br, I, OMs, OTs, or the like, and

Preparation Scheme 3 in case where Y is ——(CH$_2$)$_m$—CO—(CH$_2$)$_n$——;

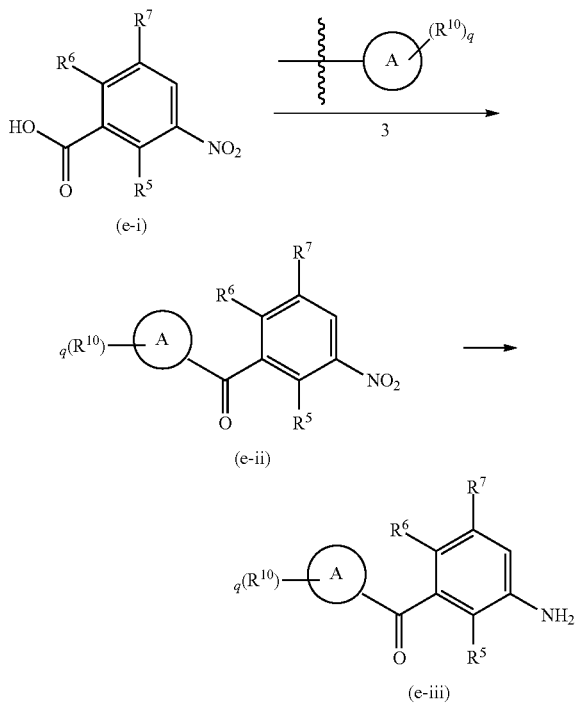

wherein, in Preparation Scheme 3, R$^6$, R$^7$, R$^{10}$, Ⓐ, and q may respectively be defined the same as those of Formulae 1 and 3.

Although the method of the preparing Formula 1 has been described by way of specific examples, specific reaction conditions, such as an amount of a reaction solvent, a base, and a reactant to be used, are not limited to those described in the present specification, and may not be construed as limiting the scope of the the present invention.

In accordance with another aspect of the present invention, provided is a pharmaceutical composition including as an active ingredient the compound of Formula 1 according to an aspect of the present invention.

In accordance with another aspect of the present invention, provided is a pharmaceutical use for the prevention and treatment of cancer of the pharmaceutical composition according to an aspect of the present invention.

In accordance with another aspect of the present invention, provided is a pharmaceutical use of the compound of Formula 1 according to an aspect of the present invention for preparing a medicine for the prevention and treatment of cancer.

In an example embodiment, the pharmaceutical composition may include a pharmaceutically acceptable excipient or additive. The pharmaceutical composition of the present invention may be formulated according to a conventional method and may be formulated into various oral dosage forms such as a tablet, a pill, powder, a capsule, syrup, emulsion, and microemulsion; or parenteral dosage forms such as intramuscular, intravenous or subcutaneous administration.

When the pharmaceutical composition of the present invention is prepared in a form of an oral formulation, examples of a carrier or additive to be used include a diluent, a disintegrant, a binder, a lubricant, a surfactant, a suspension, and an emulsifier. When the pharmaceutical composition of the present invention is prepared in a form of an injection, examples of a carrier or additive may include water, saline solution, aqueous glucose solution, pseudosaccharide solution, alcohol, glycol, ether (e.g., polyethylene glycol 400), oil, fatty acid, fatty acid ester, glyceride, a surfactant, a suspension, and an emulsifier. Such formulation methods are well known to those of ordinary skill in the pharmaceutical art.

The dose of the compound of Formula 1 as an active ingredient is an effective amount for treating or preventing cancer in a subject or a patient. The compound may be administered orally or parenterally, as desired. When the compound is administered orally, the active ingredient may be administered in an amount in a range of 0.01 milligrams (mg) to 1,000 mg, more particularly, 0.1 mg to 300 mg, per kilogram (kg) of body weight per day. When the compound is administered parenterally, the active ingredient may be administered from one to several times in an amount in a range of 0.01 mg to 100 mg, more particularly, 0.1 mg to 50 mg, per kg of body weight per day. The dose for a particular subject or patient should be determined in light of the patient's weight, age, sex, health condition, diet, time of administration, method of administration, severity of disease, etc. It is to be understood that the dose may be appropriately adjusted by a practitioner. The dose is not intended to limit the scope of the invention in any way.

In accordance with another aspect of the present invention, provided is a method of preventing or treating cancer, the method including administering a subject or a patient with a compound selected from the compound of Formula 1 according to an aspect of the present invention, an optical isomer thereof, a solvate thereof, and a pharmaceutically acceptable salt thereof.

Details of the method of preventing or treating may be the same as described above with reference to the pharmaceutical composition according to an aspect of the present invention.

The term "treatment" as used herein is used as a concept that includes treatment, improvement, amelioration, or management of disease.

The term "preventing" or "prevention" as used herein refers to prevention of a disease, for example, prevention of a disease, condition, or disorder in a subject that may be predisposed to the disease, condition, or disorder but has not yet experienced or exhibited pathology or a symptom of the disease.

The term "subject" or "patient" as used herein refers to any animal, including mammals, for example, mice, rats, other rodents, rabbits, dogs, cats, pigs, cows, sheep, horses, or primates and humans.

Hereinafter, the present invention will be described in more detail with reference to the following Examples and Experimental Examples. However, these Examples and Experimental Examples are intended to help understand the present invention, and the scope of the present invention is not limited thereto in any sense.

The abbreviations used in the following Preparation Examples, preparation methods, and Examples each indicate:

BINAP: (2,2'-bis(diphenylphosphino)-1,1'-binaphthyl)

Pd(OAc)$_2$: palladium(II) acetate

Example 1: 2-(4-(3-((5-chloro-4-(6-fluoro-1H-indol-3-yl)pyrimidine-2-yl)amino)-5-cyclopropylphenyl)piperazine-1-yl)ethane-1-ol Step 1) Preparation of 4-cyclopropyl-2-nitroaniline

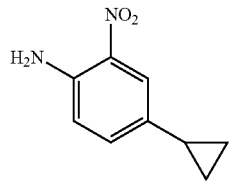 [SMILES: Nc1ccc(C2CC2)cc1[N+](=O)[O-]]

1.5 grams (g) (6.90 millimole (mmol)) of 4-bromo-2-nitroaniline, 1.22 g (13.83 mmol) of cyclopropylboronic acid, 4.5 g (20.70 mmol) of potassium phosphate, 159 mg (0.69 mmol) of palladium(II) acetate, and 543 mg (2.07 mmol) of triphenylphosphine were dissolved in 12 milliliters (mL) of toluene and 6 mL of water, and then stirred at a temperature of 100° in a sealed tube for 17 hours. Once the reaction was complete, the resultant was cooled to room temperature, and water was added dropwise thereto. An extraction process was performed thereon three times using chloroform. The result was dried using anhydrous sodium sulfate, and then concentrated under reduced pressure. The obtained residue was purified using medium pressure liquid chromatography (MPLC) (chloroform:methanol=100:1 (v/v)), and the resulting solution was concentrated under reduced pressure to thereby obtain 880 mg of a desired compound at a yield of 72%.

$^1$H-NMR (300 MHz, DMSO-$d_6$): δ 7.65 (s, 1H), 7.26 (s, 2H), 7.12 (d, 1H), 6.92 (d, 1H), 1.83 (m, 1H), 0.82 (m, 2H), 0.58 (m, 2H).

Step 2) Preparation of 2-bromo-4-cyclopropyl-6-nitroaniline

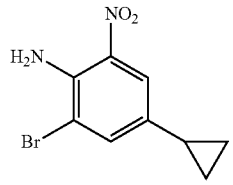 [SMILES: Nc1c(Br)cc(C2CC2)cc1[N+](=O)[O-]]

880 mg (4.94 mmol) of 4-cyclopropyl-2-nitroaniline prepared in Step 1) was dissolved in 16 mL of acetic acid, and 922 mg (5.18 mmol) of N-bromosuccinimide was slowly added thereto at a temperature of 0° C. The resultant was stirred at room temperature for 1.5 hours. Once the reaction was complete, water was added dropwise thereto. An extraction process was performed thereon three times using diethylether. The result was dried using anhydrous sodium sulfate, and then concentrated under reduced pressure to thereby obtain 1.24 g of a desired compound at a yield of 98%.

$^1$H-NMR (300 MHz, DMSO-$d_6$): δ 7.88 (s, 1H), 7.59 (s, 1H), 7.16 (m, 2H), 1.95 (m, 1H), 0.88 (m, 2H), 0.64 (m, 2H).

Step 3) Preparation of 1-bromo-3-cyclopropyl-5-nitrobenzene

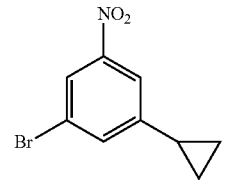 [SMILES: O=[N+]([O-])c1cc(Br)cc(C2CC2)c1]

1.24 g (4.82 mmol) of 2-bromo-4-cyclopropyl-6-nitroaniline prepared in Step 2) was dissolved in 24 mL of ethanol. Subsequently, 1.6 mL (30.39 mmol) of sulfuric acid was slowly added thereto at a temperature of 0° C. The temperature of the result was allowed to be raised up to 60° C. and then 1.06 g (15.42 mmol) of sodium nitrite was slowly added thereto. This mixture was stirred under reflux at a temperature of 100° C. for 4 hours. Once the reaction was complete, the resultant was cooled to room temperature, and ethyl acetate and water was added thereto. An organic layer was separated therefrom, which was then dried using anhydrous sodium sulfate and concentrated under reduced pressure. The obtained residue was purified using MPLC (ethyl acetate:hexane=1:50 (v/v)), and the resulting solution was concentrated under reduced pressure to thereby obtain 790 mg of a desired compound at a yield of 68%.

$^1$H-NMR (300 MHz, DMSO-$d_6$): δ8.10 (s, 1H), 7.98 (s, 1H), 7.74 (s, 1H), 2.11 (m, 1H), 1.11 (m, 2H), 0.86 (m, 2H).

Step 4) Preparation of 2-(4-(3-cyclopropyl-5-nitrophenyl)piperazine-1-yl)ethane-1-ol

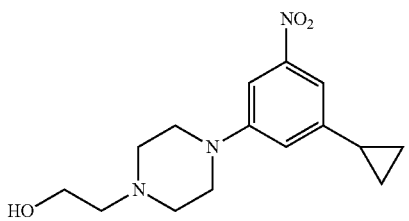 [SMILES: O=[N+]([O-])c1cc(C2CC2)cc(N2CCN(CCO)CC2)c1]

790 mg (3.26 mmol) of 1-bromo-3-cyclopropyl-5-nitrobenzene prepared in Step 3), 637 mg (4.89 mmol) of 1-(2-hydroethyl)piperazine, 300 mg (0.33 mmol) of tris(dibenzylideneacetone)dipalladium(0), 207 mg (0.33 mmol) of BINAP, and 3.2 g (9.78 mmol) of cesium carbonate were dissolved in 6 mL of 1,4-dioxane, and then the mixture was stirred at a temperature of 100° C. in a sealed tube for 15 hours. Once the reaction was complete, the resultant was cooled to room temperature, and water was added dropwise thereto. An extraction process was performed thereon three times using chloroform and methanol. The result was dried using anhydrous sodium sulfate, and then concentrated under reduced pressure. The obtained residue was purified using MPLC (chloroform:methanol=10:1 (v/v)), and the resulting solution was concentrated under reduced pressure to thereby obtain 234 mg of a desired compound at a yield of 24%.

Step 5) Preparation of 2-(4-(3-amino-5-cyclopropyl-phenyl)piperazine-1-yl)ethane-1-ol

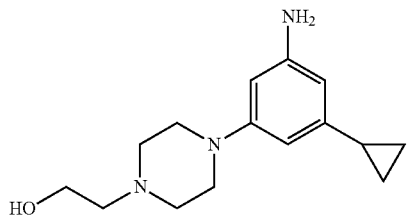

220 mg (3.96 mmol) of iron and 0.03 mL (0.32 mmol) of hydrochloric acid were dissolved in 4 mL of 50% ethanol. The mixture was stirred under reflux at a temperature of 110° C. for 1 hour. 234 mg (0.79 mmol) of 2-(4-(3-cyclopropyl-5-nitrophenyl)piperazine-1-yl)ethane-1-ol prepared in Step 4) was slowly added thereto. This mixture was stirred under reflux at a temperature of 110° C. for 1 hour. Once the reaction was complete, the mixture was cooled to room temperature, and then was neutralized using a saturated sodium hydrogen carbonate aqueous solution. A filtration process was performed thereon using a celite filter. Subsequently, a washing process was performed thereon using chloroform and methanol. An organic layer was separated therefrom, which was then dried using anhydrous sodium sulfate and concentrated under reduced pressure. The obtained residue was purified using MPLC (chloroform:methanol=8:1 (v/v)), and the resulting solution was concentrated under reduced pressure to thereby obtain 152 mg of a desired compound at a yield of 74%.

$^1$H-NMR (300 MHz, DMSO-$d_6$): δ 5.90 (s, 1H), 5.88 (s, 1H), 5.70 (s, 1H), 4.70 (s, 2H), 4.04 (m, 1H), 3.48 (m, 2H), 2.97 (m, 4H), 2.47 (m, 4H), 2.40 (m, 2H), 1.53 (m, 1H), 0.76 (m, 2H), 0.51 (m, 2H).

Step 6) Preparation of 2-(4-(3-((5-chloro-4-(6-fluoro-1H-indol-3-yl)pyrimidine-2-yl)amino)-5-cyclopropylphenyl)piperazine-1-yl)ethane-1-ol

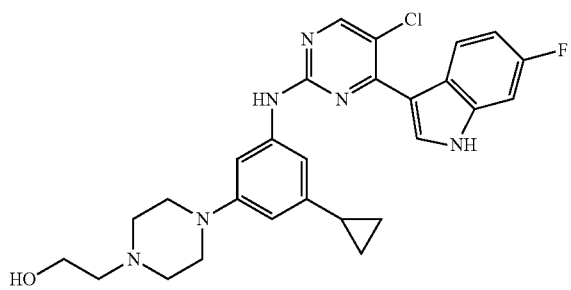 [SMILES: OCCN1CCN(c2cc(Nc3ncc(Cl)c(-c4c[nH]c5cc(F)ccc45)n3)cc(C3CC3)c2)CC1]

50 mg (0.19 mmol) of 2-(4-(3-amino-5-cyclopropylphenyl)piperazine-1-yl)ethane-1-ol prepared in Step 5), 54 mg (0.19 mmol) of 3-(2,5-dichloropyrimidine-4-yl)-6-fluoro-1H-indole, and 36 mg (0.19 mmol of p-toluenesulfonic acid monohydrate were dissolved in 1.2 mL of 2-butanol. Then, the mixture was stirred at a temperature of 120° C. in a sealed tube for 3.5 hours. Once the reaction was complete, the mixture was cooled to room temperature, and then, chloroform, methanol, and saturated sodium hydrogen carbonate were added thereto. An organic layer was separated therefrom, which was then dried using anhydrous sodium sulfate and concentrated under reduced pressure. The obtained residue was purified using MPLC (chloroform:methanol=7:1 (v/v)), and the resulting solution was concentrated under reduced pressure to thereby obtain 65 mg of a desired compound at a yield of 67%.

MS (ESI+, m/z): 507 [M+H]$^+$ $^1$H-NMR (300 MHz, DMSO-$d_6$): δ11.93 (s, 1H), 9.37 (s, 1H), 8.56 (m, 1H), 8.44 (m, 2H), 7.46 (d, 1H), 7.28 (s, 1H), 7.10 (m, 2H), 6.29 (s, 1H), 4.42 (m, 1H), 4.00 (m, 2H), 3.03 (m, 4H), 2.27 (m, 4H), 1.88 (m, 1H), 0.85 (m, 2H), 0.61 (m, 2H).

Example 2: 2-(4-(3-((5-chloro-4-(6-methyl-1H-indol-3-yl)pyrimidine-2-yl)amino)-5-cyclopropylphenyl)piperazine-1-yl)ethane-1-ol

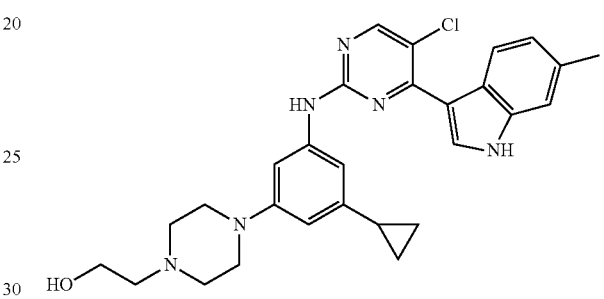

72 mg of a desired compound was obtained at a yield of 89% in substantially the same manner as in Step 6) of Example 1, except that 50 mg (0.18 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 503 [M+H]+

1H-NMR (300 MHz, DMSO-d6): δ 11.76 (s, 1H), 9.32 (s, 1H), 8.38 (m, 3H), 7.22 (d, 2H), 6.93 (d, 2H), 6.28 (s, 1H), 4.42 (t, 1H), 3.51 (q, 2H), 3.03 (bs, 4H), 2.37 (m, 9H), 1.81 (m, 1H), 0.88 (m, 2H), 0.64 (m, 2H).

Example 3: 5-chloro-N-(3-cyclopropyl-5-(4-(dimethylamino)piperidine-1-yl)phenyl)-4-(1H-indole-3-yl)pyrimidine-2-amine

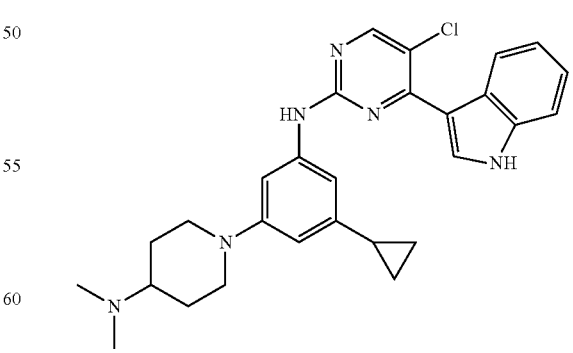

48 mg of a desired compound was obtained at a yield of 58% in substantially the same manner as in Step 6) of Example 1, except that 44 mg (0.17 mmol) of 1-(3-amino-5-cyclopropylphenyl)-N, N-dimethylpiperidine-4-amine was used instead of 2-(4-(3-amino-5-cyclopropylphenyl)piperazine-1-yl)ethane-1-ol, and 51 mg (0.19 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 487 [M+H]+

¹H-NMR (300 MHz, DMSO-d6): δ11.90 (s, 1H), 9.34 (s, 1H), 8.58 (d, 1H), 8.47 (m, 2H), 7.48 (t, 1H), 7.24 (m, 2H), 7.12 (t, 1H), 6.97 (s, 1H), 6.30 (s, 1H), 3.65 (d, 2H), 2.58 (m, 2H), 2.30 (d, 6H), 1.80 (m, 3H), 1.49 (m, 2H), 0.88 (m, 2H), 0.63 (m, 2H).

Example 4: (S)-1-((1-(3-((5-chloro-4-(1H-indole-3-yl)pyrimidine-2-yl)amino)-5-cyclopropylphenyl)piperidine-4-yl)(methyl)amino)propane-2-ol

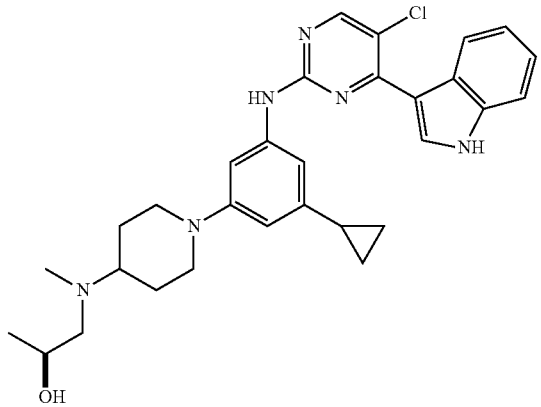 [SMILES: C[C@H](O)CN(C)C1CCN(c2cc(Nc3ncc(Cl)c(-c4c[nH]c5ccccc45)n3)cc(C3CC3)c2)CC1]

52 mg of a desired compound was obtained at a yield of 58% in substantially the same manner as in Step 6) of Example 1, except that 50 mg (0.17 mmol) of (S)-1-((1-(3-amino-5-cyclopropylphenyl)piperidine-4-yl)(methyl)amino)propane-2-ol was used instead of 2-(4-(3-amino-5-cyclopropylphenyl)piperazine-1-yl)ethane-1-ol, and 51 mg (0.19 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 531 [M+H]+

¹H-NMR (300 MHz, DMSO-d6): δ11.91 (s, 1H), 9.34 (s, 1H), 8.58 (d, 1H), 8.47 (d, 1H), 8.44 (s, 1H), 7.51 (d, 1H), 7.24 (m, 3H), 6.95 (s, 1H), 6.29 (s, 1H), 4.18 (bs, 1H), 3.65 (m, 3H), 2.59 (m, 2H), 2.29 (m, 2H), 2.20 (s, 3H), 1.78 (m, 1H), 1.64 (m, 2H), 1.46 (m, 2H), 1.24 (m, 1H), 1.10 (m, 2H), 0.85 (m, 3H), 0.63 (m, 2H).

Example 5: (S)-1-((1-(3-((5-chloro-4-(6-methyl-1H-indole-3-yl)pyrimidine-2-yl)amino)-5-cyclopropylphenyl)piperidine-4-yl)(methyl)amino)propane-2-ol

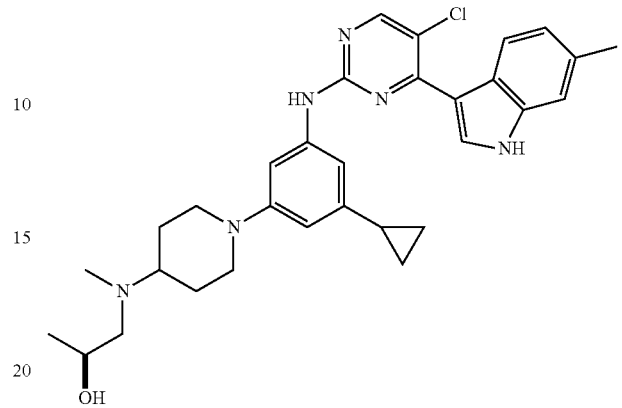

58 mg of a desired compound was obtained at a yield of 65% in substantially the same manner as in Step 6) of Example 1, except that 50 mg (0.17 mmol) of (S)-1-((1-(3-amino-5-cyclopropylphenyl)piperidine-4-yl)(methyl)amino)propane-2-ol was used instead of 2-(4-(3-amino-5-cyclopropylphenyl)piperazine-1-yl)ethane-1-ol, and 50 mg (0.18 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 545 [M+H]+

¹H-NMR (300 MHz, DMSO-d₆): δ11.75 (bs, 1H), 9.32 (s, 1H), 8.39 (m, 3H), 7.27 (d, 2H), 6.90 (m, 2H), 6.29 (s, 1H), 4.18 (bs, 1H), 3.61 (m, 3H), 2.54 (s, 1H), 2.42 (s, 3H), 2.23 (m, 2H), 2.20 (s, 3H), 1.80 (m, 1H), 1.63 (m, 2H), 1.40 (m, 2H), 1.24 (m, 2H), 1.02 (d, 6H), 0.86 (m, 2H), 0.60 (m, 2H).

Example 6: 5-chloro-N-(3-cyclopropyl-5-(4-(dimethylamino)piperidine-1-yl)phenyl)-4-(6-methyl-1H-indole-3-yl)pyrimidine-2-amine

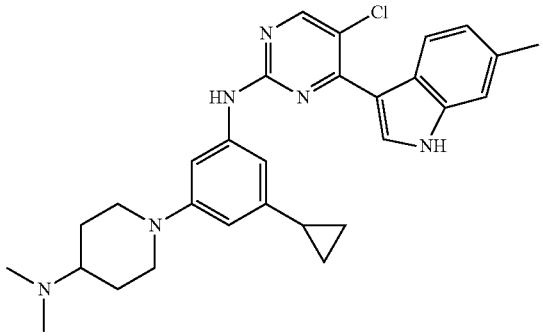

86 mg of a desired compound was obtained at a yield of 86% in substantially the same manner as in Step 6) of Example 1, except that 52 mg (0.20 mmol) of 1-(3-amino-5-cyclopropylphenyl)-N,N-dimethylpiperidine-4-amine was used instead of 2-(4-(3-amino-5-cyclopropylphenyl)piperazine-1-yl)ethane-1-ol, and 61 mg (0.22 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 501 [M+H]+
¹H-NMR (300 MHz, DMSO-d₆): δ11.77 (bs, 1H), 9.32 (s, 1H), 8.39 (m, 3H), 7.27 (s, 1H), 7.22 (s, 1H), 6.93 (d, 2H), 6.30 (s, 1H), 3.61 (d, 1H), 2.57 (m, 4H), 2.42 (s, 3H), 2.28 (m, 6H), 1.79 (m, 3H), 1.47 (m, 2H), 0.86 (m, 2H), 0.61 (m, 2H).

Example 7: 2-(4-(3-((5-chloro-4-(6-methoxy-1H-indole-3-yl)pyrimidine-2-yl)amino)-5-cyclopropyl-phenyl)piperazine-1-yl)ethane-1-ol

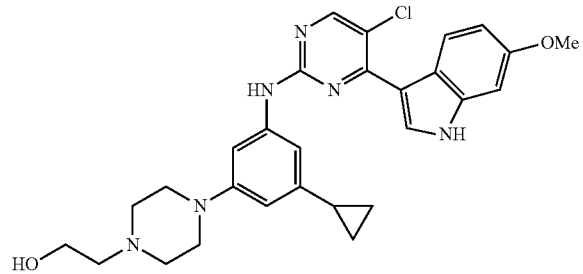 [SMILES: COc1ccc2c(-c3nc(Nc4cc(C5CC5)cc(N5CCN(CCO)CC5)c4)ncc3Cl)c[nH]c2c1]

5 mg of a desired compound was obtained at a yield of 6% in substantially the same manner as in Step 6) of Example 1, except that 50 mg (0.17 mmol) of 3-(2,5-dichloropyrimidine-4-yl)-6-methoxy-1H-indole was used instead of 3-(2,5-dichloropyrimidine-4-yl)-6-fluoro-1H-indole in Step 6) of Example 1.

MS (ESI+, m/z): 519 [M+H]+
¹H-NMR (300 MHz, DMSO-d₆): δ 11.70 (s, 1H), 9.32 (s, 1H), 8.42 (m, 3H), 7.17 (s, 1H), 6.98 (s, 1H), 6.75 (d, 1H), 6.31 (s, 1H), 3.80 (s, 3H), 3.29 (s, 1H), 3.04 (m, 2H), 1.90 (m, 1H), 0.86 (m, 2H), 0.62 (m, 2H).

Example 8: (S)-1-(1-(3-((5-chloro-4-(1H-indole-3-yl)pyrimidine-2-yl)amino)-5-cyclopropylphenyl)piperidine-4-yl)pyrrolidine-3-ol

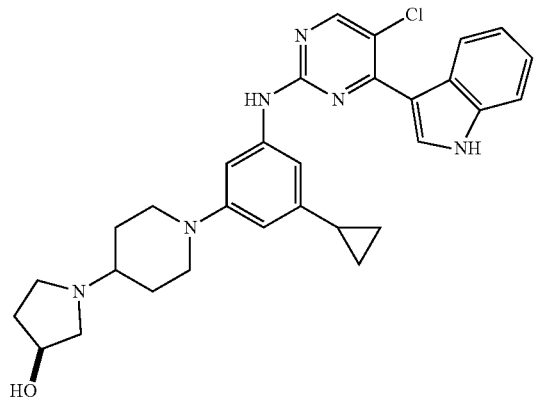 [SMILES: O[C@H]1CCN(C2CCN(c3cc(Nc4ncc(Cl)c(-c5c[nH]c6ccccc56)n4)cc(C4CC4)c3)CC2)C1]

68 mg of a desired compound was obtained at a yield of 76% in substantially the same manner as in Step 6) of Example 1, except that 50 mg (0.17 mmol) of (S)-1-(1-(3-amino-5-cyclopropylphenyl)piperidine-4-yl)pyrrolidine-3-ol was used instead of 2-(4-(3-amino-5-cyclopropylphenyl)piperazine-1-yl)ethane-1-ol, and 51 mg (0.19 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 529 [M+H]+
¹H-NMR (300 MHz, DMSO-d6): δ 11.91 (s, 1H), 9.34 (s, 1H), 8.58 (d, 1H), 8.47 (d, 1H), 8.44 (s, 1H), 7.45 (d, 1H), 7.19 (d, 2H), 7.09 (t, 1H), 6.97 (s, 1H), 6.30 (s, 1H), 4.92 (bs, 1H), 4.20 (bs, 1H), 3.77 (m, 1H), 3.54 (d, 2H), 2.58 (m, 4H), 2.28 (s, 1H), 1.98 (m, 1H), 1.83 (m, 3H), 1.70 (m, 4H), 0.86 (m, 2H), 0.62 (m, 2H).

Example 9: (S)-1-(1-(3-((5-chloro-4-(6-methyl-1H-indole-3-yl)pyrimidine-2-yl)amino)-5-cyclo propyl-phenyl)piperidine-4-yl)pyrrolidine-3-ol

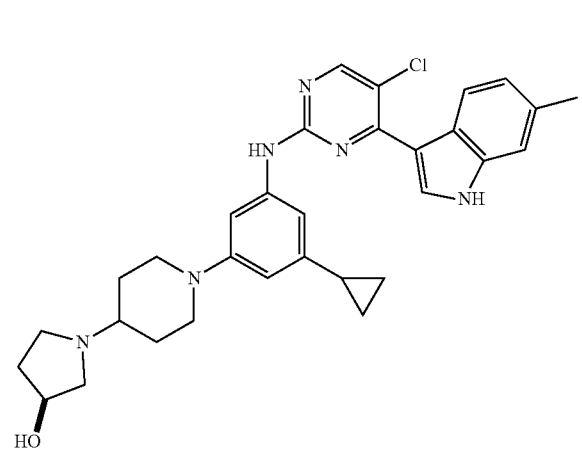 [SMILES: Cc1ccc2c(-c3nc(Nc4cc(C5CC5)cc(N5CCC(N6CC[C@H](O)C6)CC5)c4)ncc3Cl)c[nH]c2c1]

64 mg of a desired compound was obtained at a yield of 69% in substantially the same manner as in Step 6) of Example 1, except that 50 mg (0.17 mmol) of (S)-1-(1-(3-amino-5-cyclopropylphenyl)piperidine-4-yl)pyrrolidine-3-ol was used instead of 2-(4-(3-amino-5-cyclopropylphenyl)piperazine-1-yl)ethane-1-ol, and 51 mg (0.18 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 543 [M+H]+
¹H-NMR (300 MHz, DMSO-d6): δ11.77 (s, 1H), 9.32 (s, 1H), 8.45 (m, 3H), 7.27 (s, 1H), 7.22 (s, 1H), 6.96 (d, 2H), 6.29 (s, 1H), 4.92 (bs, 1H), 4.20 (bs, 1H), 3.77 (m, 1H), 3.56 (d, 2H), 2.61 (m, 4H), 2.42 (s, 3H), 2.28 (s, 1H), 1.81 (m, 4H), 1.44 (m, 4H), 0.87 (m, 2H), 0.64 (m, 2H).

Example 10: 5-chloro-N-(3-cyclopropyl-5-(4-(dimethylamino)piperidine-1-yl)phenyl)-4-(6-methoxy-1H-indole-3-yl)pyrimidine-2-amine

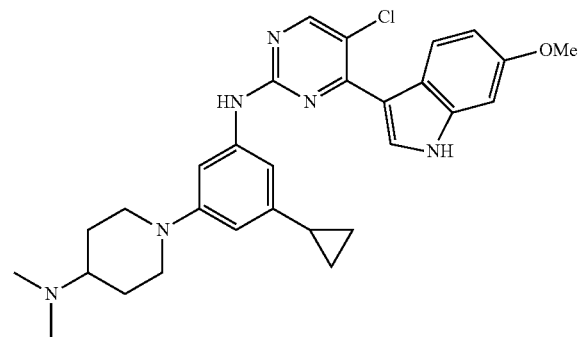 [SMILES: COc1ccc2c(-c3nc(Nc4cc(C5CC5)cc(N5CCC(N(C)C)CC5)c4)ncc3Cl)c[nH]c2c1]

20 mg of a desired compound was obtained at a yield of 23% in substantially the same manner as in Step 6) of Example 1, except that 44 mg (0.17 mmol) of 1-(3-amino-5-cyclopropylphenyl)-N, N-dimethylpiperidine-4-amine was used instead of 2-(4-(3-amino-5-cyclopropylphenyl)piperazine-1-yl)ethane-1-ol, and 50 mg (0.17 mmol) of 3-(2,5-dichloropyrimidine-4-yl)-6-methoxy-1H-indole was used instead of 3-(2,5-dichloropyrimidine-4-yl)-6-fluoro-1H-indole in Step 6) of Example 1.

MS (ESI+, m/z): 517 [M+H]+

$^1$H-NMR (300 MHz, DMSO-d$_6$): δ11.70 (s, 1H), 9.30 (s, 1H), 8.41 (m, 3H), 7.20 (s, 1H), 6.95 (d, 2H), 6.75 (d, 1H), 6.29 (s, 1H), 3.79 (s, 3H), 3.62 (d, 2H), 1.80 (m, 1H), 1.42 (m, 2H), 1.22 (m, 2H), 0.84 (d, 2H), 0.61 (d, 2H).

Example 11: (S)-1-(1-(3-((5-chloro-4-(6-methoxy-1H-indole-3-yl)pyrimidine-2-yl)amino)-5-cyclopropylphenyl)piperidine-4-yl)pyrrolidine-3-ol

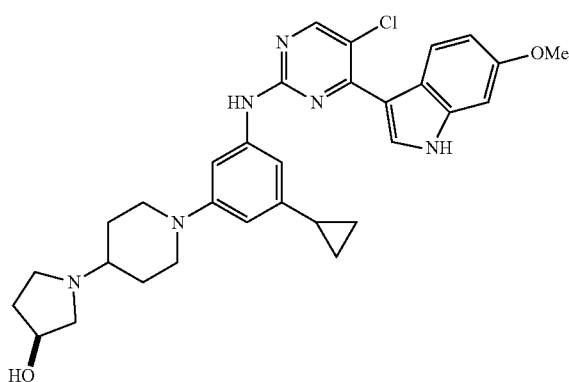 [SMILES: COc1ccc2c(-c3nc(Nc4cc(C5CC5)cc(N5CCC(N6CC[C@H](O)C6)CC5)c4)ncc3Cl)c[nH]c2c1]

9 mg of a desired compound was obtained at a yield of 10% in substantially the same manner as in Step 6) of Example 1, except that 51 mg (0.17 mmol) of (S)-1-(1-(3-amino-5-cyclopropylphenyl)piperidine-4-yl)pyrrolidine-3-ol was used instead of 2-(4-(3-amino-5-cyclopropylphenyl)piperazine-1-yl)ethane-1-ol, and 50 mg (0.17 mmol) of 3-(2,5-dichloropyrimidine-4-yl)-6-methoxy-1H-indole was used instead of 3-(2,5-dichloropyrimidine-4-yl)-6-fluoro-1H-indole in Step 6) of Example 1.

MS (ESI+, m/z): 559 [M+H]+

$^1$H-NMR (300 MHz, DMSO-d$_6$): δ 11.70 (s, 1H), 9.41 (s, 1H), 8.41 (m, 3H), 7.17 (s, 1H), 7.10 (d, 2H), 6.74 (d, 2H), 6.29 (s, 1H), 4.78 (brs, 1H), 4.19 (m, 1H), 3.77 (d, 2H), 2.65 (m, 2H), 2.62 (m, 2H), 1.84 (m, 1H), 1.80 (m, 2H), 1.45 (m, 2H), 1.22 (m, 2H), 0.83 (d, 2H), 0.60 (d, 2H).

Example 12: 2-(4-(3-((4-(1H-indole-3-yl)-5-methylpyrimidine-2-yl)amino)-5-cyclopropylphenyl)piperazine-1-yl)ethane-1-ol

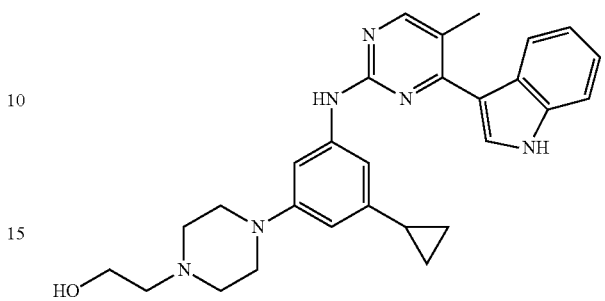

60 mg of a desired compound was obtained at a yield of 67% in substantially the same manner as in Step 6) of Example 1, except that 51 mg (0.21 mmol) of 3-(2-chloro-5-methylpyrimidine-4-yl)-1H-indole was used instead of 3-(2,5-dichloropyrimidine-4-yl)-6-fluoro-1H-indole in Step 6) of Example 1.

MS (ESI+, m/z): 469 [M+H]+

$^1$H-NMR (300 MHz, DMSO-d$_6$): δ11.69 (s, 1H), 8.96 (s, 1H), 8.52 (d, 1H), 8.29 (s, 1H), 7.96 (m, 1H), 7.46 (m, 1H), 7.25 (s, 1H), 7.19-7.02 (m, 3H), 6.19 (s, 1H), 4.40 (m, 1H), 3.51 (m, 2H), 3.00 (m, 4H), 2.44 (m, 4H), 2.39 (m, 5H), 1.96 (m, 1H), 0.82 (m, 2H), 0.58 (m, 2H).

Example 13: 5-chloro-N-(3-cyclopropyl-5-(4-morpholinopiperidine-1-yl)phenyl)-4-(6-methyl-1H-indole-3-yl)pyrimidine-2-amine

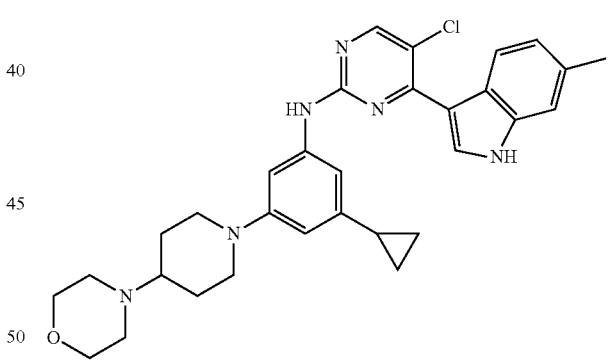

100 mg of a desired compound was obtained at a yield of 56% in substantially the same manner as in Step 6) of Example 1, except that 100 mg (0.33 mmol) of 3-cyclopropyl-5-(4-morpholinopiperidine-1-yl)aniline was used instead of 2-(4-(3-amino-5-cyclopropylphenyl)piperazine-1-yl)ethane-1-ol, and 138 mg (0.50 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 543 [M+H]+

$^1$H-NMR (300 MHz, DMSO-d$_6$): δ11.76 (s, 1H), 9.54 (s, 1H), 8.50 (m, 3H), 7.28 (s, 1H), 7.23 (s, 1H), 6.96 (m, 2H), 6.29 (s, 1H), 3.57 (s, 6H), 2.60 (m, 6H), 2.42 (s, 3H), 2.10 (m, 1H), 1.79 (m, 3H), 1.40 (q, 2H), 0.84 (m, 2H), 0.61 (m, 2H).

Example 14: 5-chloro-N-(3-cyclopropyl-5-(4-(ethyl(methyl)amino)piperidine-1-yl)phenyl)-4-(6-methyl-1H-indole-3-yl)pyrimidine-2-amine

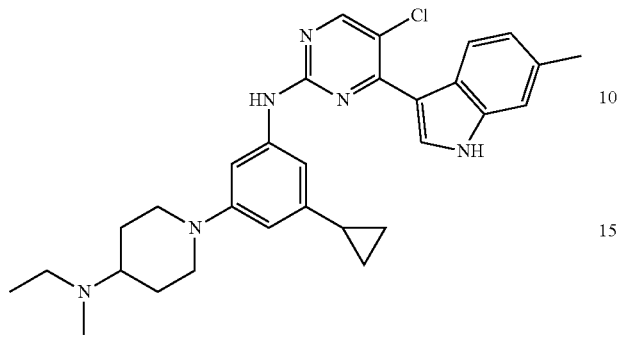

50 mg of a desired compound was obtained at a yield of 30% in substantially the same manner as in Step 6) of Example 1, except that 90 mg (0.33 mmol) of 1-(3-amino-5-cyclopropylphenyl)-N-ethyl-N-methylpiperidine-4-amine was used instead of 2-(4-(3-amino-5-cyclopropylphenyl)piperazine-1-yl)ethane-1-ol, and 137 mg (0.49 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 515 [M+H]$^+$ $^1$H-NMR (300 MHz, DMSO-d$_6$): δ 11.76 (s, 1H), 9.32 (s, 1H), 8.45 (m, 3H), 7.25 (d, 2H), 6.97 (m, 2H), 6.29 (s, 1H), 3.62 (d, 2H), 2.59 (m, 4H), 2.42 (s, 3H), 2.18 (s, 3H), 1.79 (m, 1H), 1.68 (d, 2H), 1.45 (q, 2H), 1.20 (m, 1H), 0.98 (t, 3H), 0.86 (m, 2H), 0.62 (m, 2H).

Example 15: 5-chloro-N-(3-cyclopropyl-5-(4-(diethylamino)piperidine-1-yl)phenyl)-4-(6-methyl-1H-indole-3-yl)pyrimidine-2-amine

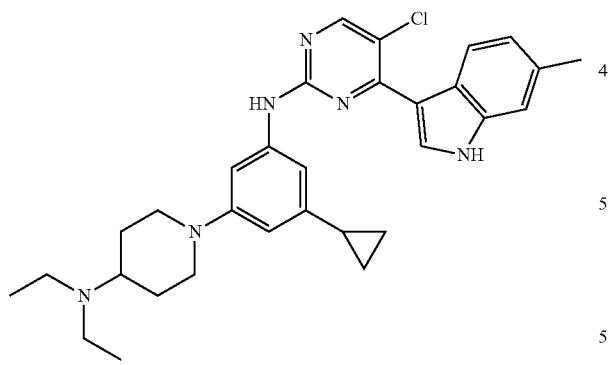

50 mg of a desired compound was obtained at a yield of 30% in substantially the same manner as in Step 6) of Example 1, except that 90 mg (0.31 mmol) of 1-(3-amino-5-cyclopropylphenyl)-N, N-dimethylpiperidine-4-amine was used instead of 2-(4-(3-amino-5-cyclopropylphenyl)piperazine-1-yl)ethane-1-ol, and 131 mg (0.47 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 529 [M+H]$^+$ $^1$H-NMR (300 MHz, DMSO-d$_6$): δ11.76 (s, 1H), 9.32 (s, 1H), 7.26 (d, 2H), 6.97 (m, 2H), 6.29 (s, 1H), 3.61 (d, 2H), 2.59 (m, 4H), 2.43 (s, 3H), 1.80 (m, 1H), 1.65 (d, 2H), 1.45 (q, 2H), 1.20 (m, 2H), 0.95 (t, 6H), 0.87 (m, 2H), 0.62 (m, 2H).

Example 16: 5-chloro-N-(3-cyclopropyl-5-(3-(dimethylamino)pyrrolidine-1-yl)phenyl)-4-(6-methyl-1H-indole-3-yl)pyrimidine-2-amine

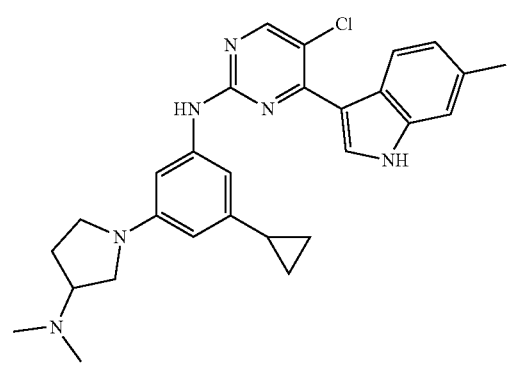

110 mg of a desired compound was obtained at a yield of 54% in substantially the same manner as in Step 6) of Example 1, except that 103 mg (0.42 mmol) of 1-(3-amino-5-cyclopropylphenyl)-N, N-dimethylpyrrolidine-3-amine was used instead of 2-(4-(3-amino-5-cyclopropylphenyl)piperazine-1-yl)ethane-1-ol, and 120 mg (0.42 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 487 [M+H]$^+$ $^1$H-NMR (300 MHz, DMSO-d$_6$): δ 11.73 (s, 1H), 9.24 (s, 1H), 8.43 (m, 3H), 7.24 (s, 1H), 6.90 (d, 1H), 6.87 (s, 1H), 6.73 (s, 1H), 5.90 (s, 1H), 3.24 (m, 1H), 3.20 (m, 1H), 2.90 (m, 1H), 2.46 (m, 1H), 2.40 (s, 3H), 1.96 (m, 6H), 1.73 (m, 2H), 0.81 (m, 2H), 0.61 (m, 2H).

Example 17: 2-(4-(3-((5-chloro-4-(6-methyl-1H-indole-3-yl)pyrimidine-2-yl)amino)-5-cyclopropylphenyl)piperazine-1-yl)-2-methylpropane-1-ol

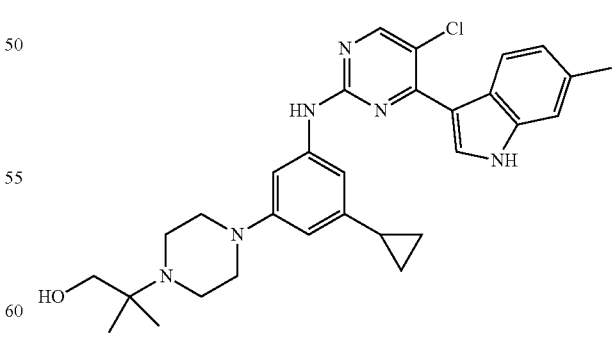

36 mg of a desired compound was obtained at a yield of 29% in substantially the same manner as in Step 6) of Example 1, except that 67 mg (0.23 mmol) of 2-(4-(3-amino-5-cyclopropylphenyl)piperazine-1-yl)-2-methylpropane-1-ol was used instead of 2-(4-(3-amino-5-cyclopropylphenyl)piperazine-1-yl)ethane-1-ol, and 70 mg (0.25 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 531 [M+H]+

$^1$H-NMR (300 MHz, DMSO-d6): δ11.75 (s, 1H), 9.32 (s, 1H), 8.44 (m, 3H), 7.27 (s, 1H), 7.23 (s, 1H), 6.97 (d, 1H), 6.89 (s, 1H), 6.27 (s, 1H), 4.24 (m, 1H), 3.26 (m, 2H), 3.00 (m, 4H), 2.58 (m, 4H), 2.42 (s, 3H), 1.79 (m, 1H), 0.94 (s, 6H), 0.88 (m, 2H), 0.63 (m, 2H).

Example 18: N-(3-(4-aminopiperidine-1-yl)-5-cyclopropylphenyl)-5-chloro-4-(6-methyl-1H-indole-3-yl)pyrimidine-2-amine

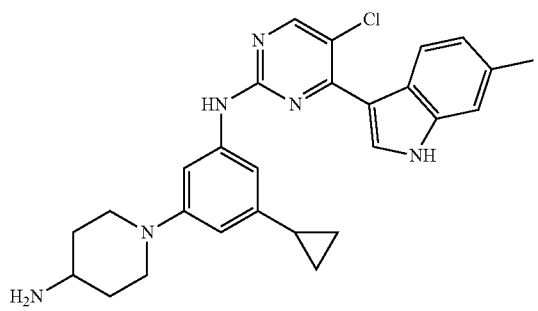 [SMILES: Cc1ccc2c(-c3nc(Nc4cc(C5CC5)cc(N5CCC(N)CC5)c4)ncc3Cl)c[nH]c2c1]

32 mg of a desired compound was obtained at a yield of 29% in substantially the same manner as in Step 6) of Example 1, except that 76 mg (0.23 mmol) of turt-butyl (1-(3-amino-5-cyclopropylphenyl)piperidine-4-yl)carbamate was used instead of 2-(4-(3-amino-5-cyclopropylphenyl)piperazine-1-yl)ethane-1-ol, and 70 mg (0.25 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 473 [M+H]+

$^1$H-NMR (300 MHz, DMSO-d6): δ11.77 (s, 1H), 9.33 (s, 1H), 8.47 (m, 3H), 7.28 (s 1H), 7.19 (m, 1H), 6.97 (m, 2H), 6.31 (s, 1H), 3.67 (d, 2H), 3.11 (m, 1H), 2.73 (m, 3H), 2.43 (s, 3H), 1.82 (m, 3H), 1.54 (m, 3H), 0.90 (m, 2H), 0.63 (m, 2H).

Example 19: 5-chloro-N-(3-cyclopropyl-5-(4-(methylamino)piperidine-1-yl)phenyl)-4-(6-methyl-1H-indole-3-yl)pyrimidine-2-amine

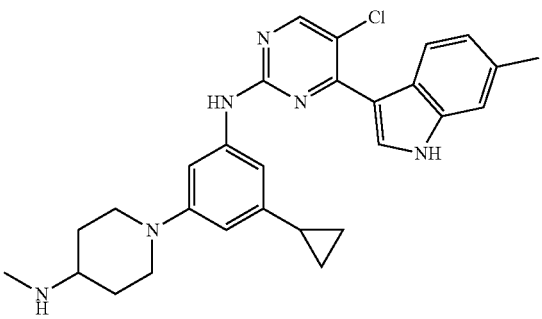

11 mg of a desired compound was obtained at a yield of 10% in substantially the same manner as in Step 6) of Example 1, except that 79 mg (0.23 mmol) of turt-butyl (1-(3-amino-5-)piperidine-4-yl)(methyl)carbamate was used instead of 2-(4-(3-amino-5-cyclopropylphenyl)piperazine-1-yl)ethane-1-ol and 70 mg (0.25 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 487 [M+H]+

$^1$H-NMR (300 MHz, DMSO-d6): δ 11.75 (bs, 1H), 9.30 (s, 1H), 8.46 (m, 3H), 7.27 (s, 1H), 7.19 (s, 1H), 6.96 (d, 1H), 6.93 (s, 1H), 6.29 (s, 1H), 3.54 (m, 2H), 3.33 (s, 3H), 2.63 (m, 4H), 2.42 (s, 3H), 1.81 (m, 3H), 1.23 (m, 2H), 0.86 (2H), 0.62 (2H).

Example 20: 2-(4-(3-((5-chloro-4-(6-fluoro-1H-indole-3-yl)pyrimidine-2-yl)amino)-5-cyclopropylphenyl)piperazine-1-yl)-2-methylpropane-1-ol

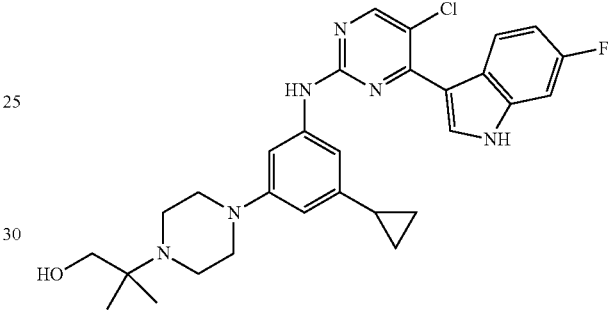

30 mg of a desired compound was obtained at a yield of 33% in substantially the same manner as in Step 6) of Example 1, except that 50 mg (0.17 mmol) of 2-(4-(3-amino-5-cyclopropylphenyl)piperazine-1-yl)-2-methylpropane-1l-ol was used instead of 2-(4-(3-amino-5-cyclopropylphenyl)piperazine-1-yl)ethane-1-ol in Step 6) of Example 1.

MS (ESI+, m/z): 535 [M+H]+

$^1$H-NMR (300 MHz, DMSO-d6): δ11.95 (s, 1H), 9.39 (s, 1H), 8.57 (m, 1H), 8.49 (d, 1H), 8.45 (s, 1H), 7.30 (dd, 1H), 7.26 (s, 1H), 6.96 (m, 1H), 6.90 (s, 1H), 6.28 (s, 1H), 4.24 (m, 1H), 3.29 (m, 2H), 3.01 (bs, 4H), 2.60 (bs, 4H), 1.79 (m, 1H), 0.95 (s, 6H), 0.87 (m, 2H), 0.63 (m, 2H).

Example 21: 2-(4-(3-((5-chloro-4-(6-methyl-1H-indole-3-yl)pyrimidine-2-yl)amino)-5-cyclopropylphenyl)piperidine-1-yl)ethane-1-ol

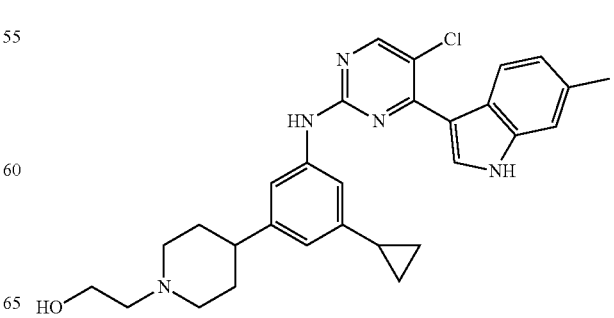

7 mg of a desired compound was obtained at a yield of 6% in substantially the same manner as in Step 6) of Example 1, except that 64 mg (0.25 mmol) of 2-(4-(3-amino-5-cyclopropylphenyl)piperidine-1-yl)ethane-1-ol was used instead of 2-(4-(3-amino-5-cyclopropylphenyl)piperazine-1-yl)ethane-1-ol, and 103 mg (0.37 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 502 [M+H]+

$^1$H-NMR (300 MHz, DMSO-$d_6$): δ 11.78 (s, 1H), 9.43 (s, 1H), 8.49 (m, 3H), 7.51 (s, 1H), 7.29 (s, 1H), 6.95 (d, 1H), 6.57 (s, 1H), 4.44 (m, 1H), 3.52 (s, 2H), 2.98 (d, 2H), 2.43 (s, 3H), 2.06 (m, 2H), 1.83 (m, 1H), 1.70 (m, 4H), 1.23 (s, 2H), 0.91 (m, 2H), 0.64 (m, 2H).

Example 22: 2-(4-(3-((5-chloro-4-(6-chloro-1H-indole-3-yl)pyrimidine-2-yl)amino)-5-cyclopropyl-phenyl)piperazine-1-yl)ethane-1-ol

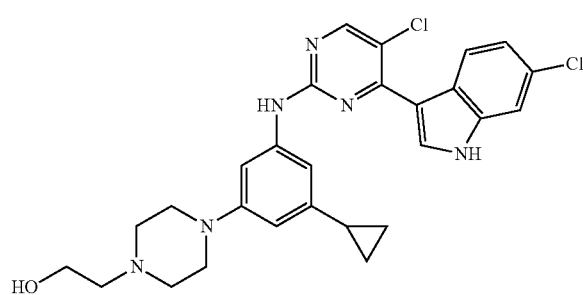 [SMILES: OCCN1CCN(c2cc(Nc3ncc(Cl)c(-c4c[nH]c5cc(Cl)ccc45)n3)cc(C3CC3)c2)CC1]

84 mg of a desired compound was obtained at a yield of 59% in substantially the same manner as in Step 6) of Example 1, except that 88 mg (0.29 mmol) of 6-chloro-3-(2,5-dichloropyrimidine-4-yl)-6-chloro-1H-indole was used instead of 3-(2,5-dichloropyrimidine-4-yl)-6-fluoro-1H-indole in Step 6) of Example 1.

MS (ESI+, m/z): 532 [M+H]+

$^1$H-NMR (300 MHz, DMSO-d6): δ11.99 (s, 1H), 9.39 (s, 1H), 8.57 (d, 1H), 8.51 (s, 1H), 8.46 (s, 1H), 7.55 (d, 1H), 7.19 (s, 1H), 7.11 (dd, 1H), 6.89 (s, 1H), 6.30 (s, 1H), 4.41 (t, 1H), 3.51 (q, 2H), 3.03 (s, 4H), 2.46 (s, 4H), 2.40 (t, 2H), 1.79 (m, 1H), 0.87 (m, 2H), 0.62 (m, 2H).

Example 23: 5-chloro-N-(3-cyclopropyl-5-(4-(pyrrolidine-1-yl)piperidine-1-yl)phenyl)-4-(6-methyl-1H-indole-3-yl)pyrimidine-2-amine

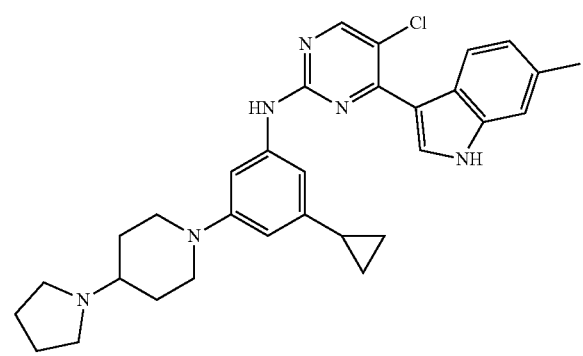 [SMILES: Cc1ccc2c(-c3nc(Nc4cc(C5CC5)cc(N5CCC(N6CCCC6)CC5)c4)ncc3Cl)c[nH]c2c1]

135 mg of a desired compound was obtained at a yield of 73% in substantially the same manner as in Step 6) of Example 1, except that 100 mg (0.35 mmol) of 3-cyclopropyl-5-(4-(pyrrolidine-1-yl)piperidine-1-yl)aniline was used instead of 2-(4-(3-amino-5-cyclopropylphenyl)piperazine-1-yl)ethane-1-ol, and 146 mg (0.53 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 527 [M+H]+

$^1$H-NMR (300 MHz, DMSO-$d_6$): δ 11.76 (s, 1H), 8.45 (m, 3H), 7.27 (s, 1H), 7.23 (s, 1H), 6.96 (s, 1H), 6.93 (s, 1H), 6.30 (s, 1H), 3.53 (d, 2H), 3.34 (m, 7H), 2.42 (s, 3H), 1.85 (m, 3H), 1.69 (s, 4H), 1.43 (d, 2H), 0.86 (m, 2H), 0.62 (m, 2H).

Example 24: 1-(1-(3-((5-chloro-4-(6-methyl-1H-indole-3-yl)pyrimidine-2-yl)amino)-5-cyclopropyl-phenyl)piperidine-4-yl)azetidine-3-ol

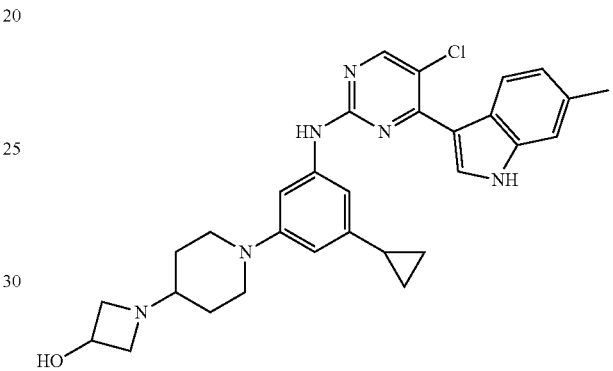

130 mg of a desired compound was obtained at a yield of 71% in substantially the same manner as in Step 6) of Example 1, except that 100 mg (0.35 mmol) of 1-(1-(3-amino-5-cyclopropylphenyl)piperidine-4-yl)azetidine-3-ol was used instead of 2-(4-(3-amino-5-cyclopropylphenyl)piperazine-1-yl)ethane-1-ol, and 145 mg (0.52 mmol) of 3-(2,5-dichloropyrimidine-4-yl)-6-methyl-1H-indole was used instead of 3-(2,5-dichloropyrimidine-4-yl)-6-fluoro-1H-indole in Step 6) of Example 1.

MS (ESI+, m/z): 529 [M+H]+

$^1$H-NMR (300 MHz, DMSO-$d_6$): δ 11.77 (s, 1H), 9.32 (s, 1H), 8.47 (m, 3H), 7.27 (s, 1H), 7.20 (s, 1H), 6.96 (s, 1H), 6.94 (s, 1H), 5.27 (brs, 1H), 3.73 (m, 5H), 2.72 (m, 5H), 1.90 (m, 3H), 1.31 (m, 2H), 0.88 (m, 2H), 0.62 (m, 2H).

Example 25: 2-(4-(3-((5-chloro-4-(1H-indole-3-yl)pyrimidine-2-yl)amino)-5-methoxyphenyl)piperazine-1-yl)ethane-1-ol

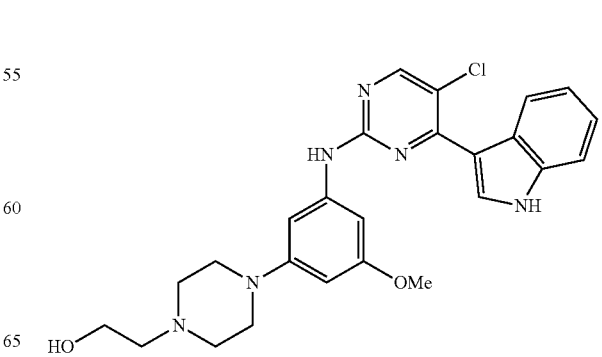

25 mg of a desired compound was obtained at a yield of 27% in substantially the same manner as in Step 6) of Example 1, except that 48 mg (0.19 mmol) of 2-(4-(3-amino-5-methoxyphenyl)piperazine-1-yl)ethane-1-ol was used instead of 2-(4-(3-amino-5-cyclopropylphenyl)piperazine-1-yl)ethane-1-ol, and 56 mg (0.21 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 479 [M+H]$^+$ $^1$H-NMR (300 MHz, DMSO-d$_6$): δ 11.87 (bs, 1H), 9.39 (s, 1H), 8.58 (d, 1H), 8.44 (m, 2H), 7.49 (d, 1H), 7.22 (m, 1H), 7.13 (m, 1H), 6.96 (s, 2H), 6.10 (s, 1H), 3.63 (s, 3H), 3.52 (m, 2H), 3.39 (m, 2H), 3.05 (m, 4H), 2.46 (m, 2H).

Example 26: 2-(4-(3-((5-chloro-4-(6-fluoro-1H-indole-3-yl)pyrimidine-2-yl)amino)phenyl)piperazine-1-yl)ethane-1-ol

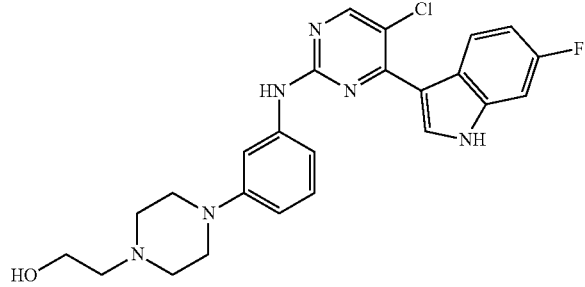 [SMILES: OCCN1CCN(c2cccc(Nc3ncc(Cl)c(-c4c[nH]c5cc(F)ccc45)n3)c2)CC1]

23 mg of a desired compound was obtained at a yield of 28% in substantially the same manner as in Step 6) of Example 1, except that 50 mg (0.177 mmol) of 2-(4-(3-aminophenyl)piperazine-1-yl)ethane-1-ol was used instead of 2-(4-(3-amino-5-cyclopropylphenyl)piperazine-1-yl)ethane-1-ol in Step 6) of Example 1.

MS (ESI+, m/z): 467 [M+H]$^+$ $^1$H-NMR (300 MHz, DMSO-d$_6$): δ11.93 (bs, 1H), 9.47 (s, 1H), 8.60 (m, 1H), 8.48 (s, 1H), 8.45 (s, 1H), 7.33 (s, 1H), 7.29 (m, 2H), 7.13 (t, 1H), 6.98 (m, 1H), 6.59 (m, 1H), 4.42 (t, 1H), 3.53 (q, 2H), 3.05 (m, 4H), 2.48 (m, 4H), 2.41 (t, 2H).

Example 27: 2-(4-(3-((5-chloro-4-(1H-indole-3-yl)pyrimidine-2-yl)amino)phenyl)piperidine-1-yl)ethane-1-ol

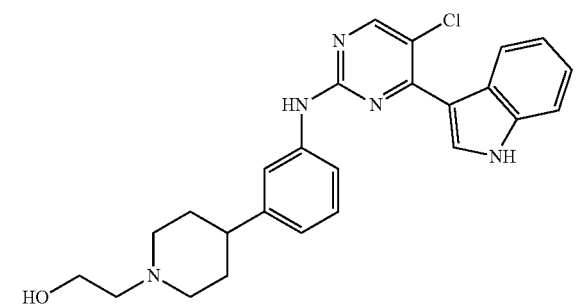 [SMILES: OCCN1CCC(c2cccc(Nc3ncc(Cl)c(-c4c[nH]c5ccccc45)n3)c2)CC1]

20 mg of a desired compound was obtained at a yield of 25% in substantially the same manner as in Step 6) of Example 1, except that 40 mg (0.18 mmol) of 2-(4-(3-aminophenyl)piperidine-1-yl)ethane-1-ol was used instead of 2-(4-(3-amino-5-cyclopropylphenyl)piperazine-1-yl)ethane-1-ol, and 53 mg (0.20 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 448 [M+H]$^+$ $^1$H-NMR (300 MHz, DMSO-d6): δ11.92 (s, 1H), 9.57 (s, 1H), 8.58 (d, 1H), 8.47 (m, 2H), 7.67 (s, 1H), 7.64 (d, 1H), 7.52 (d, 1H), 7.25 (q, 2H), 7.12 (t, 1H), 6.88 (d, 1H), 4.41 (bs, 1H), 3.43 (m, 2H), 2.94 (m, 2H), 2.41 (m, 3H), 2.03 (m, 2H), 1.61 (m, 4H).

Example 28: 2-(4-(3-((5-chloro-4-(1H-indole-3-yl)pyrimidine-2-yl)amino)phenyl) piperazine-1-yl)ethane-1-ol

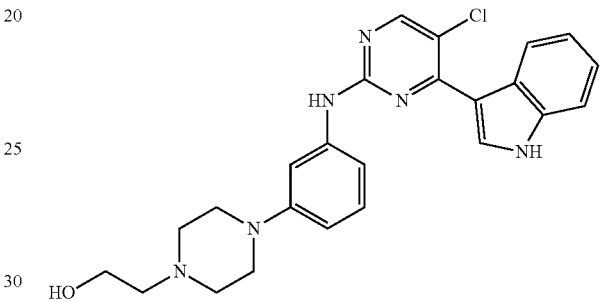

33 mg of a desired compound was obtained at a yield of 39% in substantially the same manner as in Step 6) of Example 1, except that 42 mg (0.19 mmol) of 2-(4-(3-aminophenyl)piperazine-1-yl)ethane-1-ol was used instead of 22-(4-(3-amino-5-cyclopropylphenyl)piperazine-1-yl)ethane-1-ol, and 55 mg (0.21 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 449 [M+H]$^+$ $^1$H-NMR (300 MHz, DMSO-d$_6$): δ11.88 (s, 1H), 9.43 (s, 1H), 8.57 (m, 1H), 8.46 (m, 2H), 7.49 (d, 1H), 7.34 (s, 1H), 7.26 (m, 4H), 6.57 (m, 1H), 4.41 (m, 1H), 3.52 (m, 2H), 3.04 (s, 4H), 2.47 (m, 4H), 2.38 (m, 2H).

Example 29: 5-chloro-N-(3-(4-(dimethylamino)piperidine-1-yl)phenyl)-4-(1H-indole-3-yl)pyrimidine-2-amine

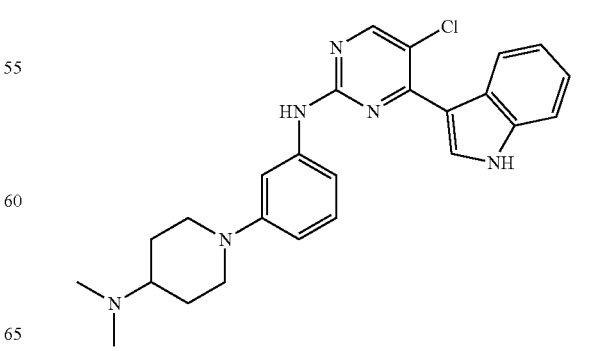

47 mg of a desired compound was obtained at a yield of 66% in substantially the same manner as in Step 6) of Example 1, except that 35 mg (0.16 mmol) of 1-(3-aminophenyl)-N, N-dimethylpiperidine-4-amine was used instead of 2-(4-(3-amino-5-cyclopropylphenyl)piperazine-1-yl)ethane-1-ol, and 48 mg (0.18 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 447 [M+H]+

$^1$H-NMR (300 MHz, DMSO-$d_6$): δ11.90 (s, 1H), 9.43 (s, 1H), 8.58 (d, 1H), 8.44 (m, 2H), 7.51 (d, 1H), 7.38 (s, 1H), 7.22 (t, 2H), 7.12 (q, 2H), 6.59 (dd, 1H), 3.61 (m, 3H), 2.60 (t, 2H), 2.20 (s, 6H), 1.78 (d, 2H), 1.44 (m, 2H).

Example 30: 5-chloro-N-(3-(3-(dimethylamino)pyrrolidine-1-yl)phenyl)-4-(1H-indole-3-yl)pyrimidine-2-amine

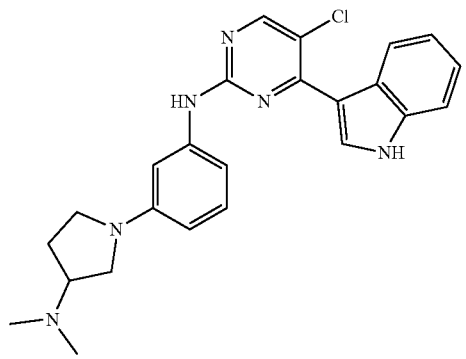 [SMILES: CN(C)C1CCN(c2cccc(Nc3ncc(Cl)c(-c4c[nH]c5ccccc45)n3)c2)C1]

26 mg of a desired compound was obtained at a yield of 38% in substantially the same manner as in Step 6) of Example 1, except that 33 mg (0.16 mmol) of (S)-1-(3-amino-5-cyclopropylphenyl)-N, N-dimethylpyrrolidine-3-amine was used instead of 2-(4-(3-amino-5-cyclopropylphenyl)piperazine-1-yl)ethane-1-ol, and 48 mg (0.18 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 473 [M+H]+

$^1$H-NMR (300 MHz, DMSO-$d_6$): δ11.88 (bs, 1H), 9.38 (s, 1H), 8.58 (d, 1H), 8.47 (d, 1H), 8.43 (s, 1H), 7.48 (d, 1H), 7.21 (t, 1H), 7.11 (m, 3H), 6.98 (s, 1H), 6.20 (m, 1H), 3.48 (m, 2H), 3.29 (m, 2H), 2.94 (t, 1H), 2.78 (m, 1H), 2.12 (s, 6H), 1.73 (m, 1H).

Example 31: 2-(4-(3-((5-chloro-4-(6-fluoro-1H-indole-3-yl)pyrimidine-2-yl)amino)-5-methoxyphenyl)piperazine-1-yl)ethane-1-ol

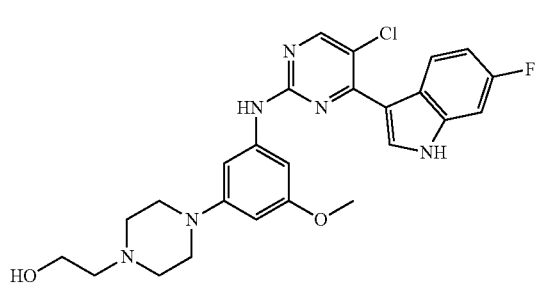 [SMILES: COc1cc(Nc2ncc(Cl)c(-c3c[nH]c4cc(F)ccc34)n2)cc(N2CCN(CCO)CC2)c1]

40 mg of a desired compound was obtained at a yield of 50% in substantially the same manner as in Step 6) of Example 1, except that 40 mg (0.16 mmol) of 2-(4-(3-amino-5-methoxyphenyl)piperazine-1-yl)ethane-1-ol was used instead of 2-(4-(3-amino-5-cyclopropylphenyl)piperazine-1-yl)ethane-1-ol in Step 6) of Example 1.

MS (ESI+, m/z): 497 [M+H]+

$^1$H-NMR (300 MHz, DMSO-d6): δ11.95 (s, 1H), 9.46 (s, 1H), 8.60 (dd, 1H), 8.50 (m, 2H), 7.29 (dd, 1H), 6.99 (m, 3H), 6.13 (s, 1H), 4.43 (t, 1H), 3.66 (s, 3H), 3.52 (q, 2H), 3.06 (bs, 4H), 2.49 (bs, 4H), 2.40 (t, 2H).

Example 32: 2-(4-(3-((5-chloro-4-(1H-indole-3-yl)pyrimidine-2-yl)amino)-5-isopropoxyphenyl) piperazine-1-yl)ethane-1-ol

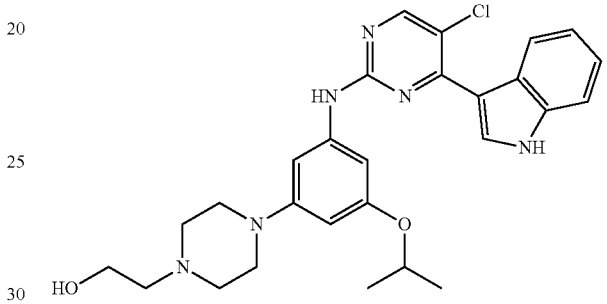

61 mg of a desired compound was obtained at a yield of 67% in substantially the same manner as in Step 6) of Example 1, except that 50 mg (0.18 mmol) of 2-(4-(3-amino-5-isopropoxyphenyl)piperazine-1-yl)ethane-1-ol was used instead of 2-(4-(3-amino-5-cyclopropylphenyl)piperazine-1-yl)ethane-1-ol, and 54 mg (0.20 mmol) of 3-(2,5-dichloropyrimidine-4-yl)-1H-indole was used instead of 3-(2,5-dichloropyrimidine-4-yl)-6-fluoro-1H-indole in Step 6) of Example 1.

MS (ESI+, m/z): 507 [M+H]+

$^1$H-NMR (300 MHz, DMSO-$d_6$): δ11.87 (bs, 1H), 9.36 (s, 1H), 8.56 (d, 1H), 8.44 (s, 1H), 7.49 (d, 1H), 7.22 (m, 1H), 7.13 (m, 1H), 6.95 (m, 2H), 6.06 (s, 1H), 4.48 (m, 1H), 4.40 (m, 1H), 3.52 (m, 2H), 3.02 (m, 4H), 2.48 (m, 5H), 1.20 (m, 6H).

Example 33: 2-(4-(3-((5-chloro-4-(6-fluoro-1H-indole-3-yl)pyrimidine-2-yl)amino)-5-isopropoxyphenyl)piperazine-1-yl)ethane-1-ol

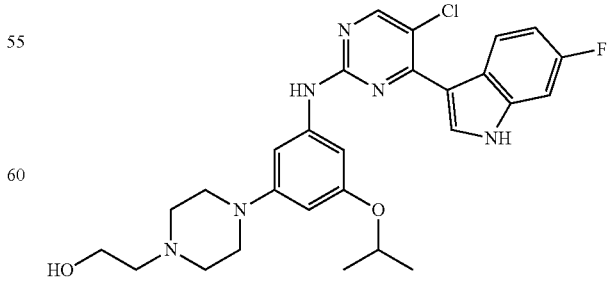

74 mg of a desired compound was obtained at a yield of 78% in substantially the same manner as in Step 6) of Example 1, except that 50 mg (0.18 mmol) of 2-(4-(3-amino-5-isopropoxyphenyl)piperazine-1-yl)ethane-1-ol was used instead of 2-(4-(3-amino-5-cyclopropylphenyl)piperazine-1-yl)ethane-1-ol in Step 6) of Example 1.

MS (ESI+, m/z): 525 [M+H]+

$^1$H-NMR (300 MHz, DMSO-$d_6$): δ11.91 (bs, 1H), 9.39 (s, 1H), 8.59 (m, 1H), 8.46 (s, 2H), 7.28 (d, 1H), 6.97 (m, 3H), 6.07 (s, 1H), 4.48 (m, 1H), 4.40 (m, 1H), 3.50 (m, 2H), 3.27 (m, 4H), 2.48 (m, 3H), 1.17 (m, 6H).

Example 34: 5-chloro-N-(3-cyclopropyl-5-(piperazine-1-ylmethyl)phenyl)-4-(6-fluoro-1H-indole-3-yl)pyrimidine-2-amine Step 1) Preparation of 3-bromo-5-nitrobenzoic acid

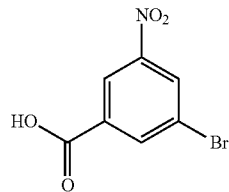

11.2 g (67 mmol) of 3-nitrobenzoic acid was dissolved in 30 mL of concentrated (conc.) sulfuric acid (H$_2$SO$_4$), and the temperature was raised to 60° C. 14.3 g (80.4 mmol) of N-bromosuccinimide was added thereto three times for 15 minutes. The mixture was then stirred at a temperature of 60° C. for 2 hours. Once the reaction was complete, ice was added to the reaction mixture. The resulting solid was filtered, and then dried at a temperature of 50° C. in an oven for 12 hours to thereby obtain 16.4 g of a desired compound at a yield of 99%.

$^1$H-NMR (300 MHz, DMSO-$d_6$): δ8.59 (s, 1H), 8.51 (s, 1H), 8.38 (s, 1H).

Step 2) Preparation of (3-bromo-5-nitrophenyl)methanol

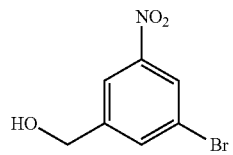 [SMILES: O=[N+]([O-])c1cc(Br)cc(CO)c1]

4.0 g (16.3 mmol) of 3-bromo-5-nitrobenzoic acid prepared in Step 1) was dissolved in 25 mL of THF, and the temperature was lowered to 0° C. 32.5 mL (65.2 mmol) of borane-dimethyl sulfide (2.0 M in THF) was slowly added dropwise thereto for 45 minutes. The mixture was stirred at room temperature for 12 hours, and then stirred under reflux at a temperature of 70° C. for 1.5 hours. Once the reaction was complete, the resultant was cooled to room temperature, and saturated sodium hydrogen carbonate was added dropwise thereto. An extraction process was performed thereon three times using ethyl acetate, and an organic layer was washed with saline water, dried using anhydrous sodium sulfate, and concentrated under reduced pressure. The obtained residue was purified using column chromatography (chloromethylene:methanol=10:1 (v/v)), and the resulting solution was concentrated under reduced pressure to thereby obtain 3.0 g of a desired compound at a yield of 80%.

$^1$H-NMR (300 MHz, DMSO-$d_6$): δ 8.23 (s, 1H), 8.17 (s, 1H), 7.96 (s, 1H), 4.63 (s, 2H).

Step 3) Preparation of (3-cyclopropyl-5-nitrophenyl)methanol

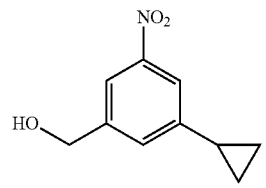 [SMILES: O=[N+]([O-])c1cc(CO)cc(C2CC2)c1]

5 g (22.93 mmol) of (3-bromo-5-nitrophenyl)methanol prepared in Step 2), 5.9 g (68.80 mmol) of cyclopropylboronic acid, 514 mg (2.29 mmol) of Pd(OAc)$_2$, 14.6 g (68.80 mmol) of—potassium phosphate, and 1.8 g (6.88 mmol) of triphenylphosphine were dissolved in 75 mL of a mixed solvent of toluene and H$_2$O (at a ratio of 2:1), and then purged with nitrogen for 5 minutes to remove gas. The reaction mixture was sealed, and the temperature was raised to 100° C., followed by stirring under reflux for 12 hours. Once the reaction was complete, the mixture solution was cooled to room temperature, and the mixture solution was filtered using a celite filter. The celite layer was washed with ethyl acetate. An organic layer was separated from the mixture solution, and the organic layer was washed with saline water, dried using anhydrous sodium sulfate, and concentrated under reduced pressure. The obtained residue was purified using column chromatography (ethyl acetate:hexane=1:10 (v/v)), and the resulting solution was concentrated under reduced pressure to thereby obtain 1.25 g of a desired compound at a yield of 50%.

$^1$H-NMR (300 MHz, DMSO-$d_6$): δ8.07 (s, 1H), 7.71 (s, 1H), 7.25 (s, 1H), 4.70 (s, 2H), 1.90 (m, 1H), 1.01 (m, 2H), 0.71 (m, 2H).

Step 4) Preparation of 2-(4-(3-nitrobenzyl)piperazine-1-yl)ethane-1-ol

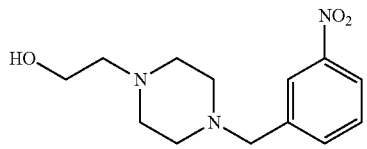

1.0 g (6.53 mmol) of (3-cyclopropyl-5-nitrophenyl)methanol prepared in Step 3) was dissolved in 44 mL of a solvent (THF:water=10:1). Subsequently, 0.52 g (13.06 mmol) of sodium hydroxide and 1.6 g (8.49 mmol) of p-toluenesulfonyl chloride were added thereto. The mixture was stirred at room temperature for 2 hours. Once the reaction was complete, water was added dropwise thereto. An extraction process was performed thereon three times using ethyl acetate, and an organic layer was washed with saline water, dried using anhydrous sodium sulfate, and concentrated under reduced pressure. The obtained residue was dissolved in 20 mL of N, N-dimethyl formamide, and then, 1.33 g (9.60 mmol) of potassium carbonate (K$_2$CO$_3$)

and 0.75 g (5.76 mmol) of 2-(piperazine-1-yl)ethane-1-ol were added thereto, followed by stirring at a temperature of 100° C. for 1 hour. Once the reaction was complete, the mixture solution was cooled to room temperature, and ethyl acetate and water was added dropwise thereto. An organic layer was extracted therefrom, and the organic layer was washed with saline water, dried using anhydrous sodium sulfate, and concentrated under reduced pressure. The obtained residue was purified using column chromatography (chloromethylene:methanol=30:1 (v/v)), and the resulting solution was concentrated under reduced pressure to thereby obtain 602 mg of a desired compound at a yield of 47%.

$^1$H-NMR (300 MHz, DMSO-$d_6$): δ 8.11 (s, 1H), 8.07 (m, 1H), 7.74 (d, 1H), 7.60 (t, 1H), 4.33 (t, 1H), 3.56 (s, 2H), 3.43 (m, 2H), 2.34 (m, 10H).

Step 5) Preparation of 2-(4-(3-aminobenzyl)piperazine-1-yl)ethane-1-ol

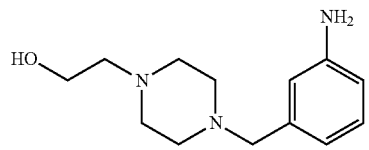 [SMILES: O=[N+]([O-])c1cccc(CN2CCN(CCO)CC2)c1]

50% ethanol was added to iron (Fe) powder, and conc. HCl was slowly added dropwise thereto. The mixture was then stirred under reflux at a temperature of 120° C. for 1 hour to activate the mixture. 602 mg (2.27 mmol) of 2-(4-(3-nitrobenzyl)piperazine-1-yl)ethane-1-ol prepared in Step 4) was added to the activated iron mixture, followed by stirring under reflux at a temperature of 120° C. for 1 hour. Once the reaction was complete, a filtration process was performed thereon using a celite filter. A mixture solution of chloroform and 2-propanol (3:1) and saturated sodium hydrogen carbonate solution were added dropwise to the filtrate. An organic layer was separated from the mixture solution, washed with saline water, dried using anhydrous sodium sulfate, and concentrated under reduced pressure to thereby obtain 330 mg of a desired compound at a yield of 62%.

Step 6) Preparation of 2-(4-(3-((5-chloro-4-(1H-indole-3-yl)pyrimidine-2-yl)amino)benzyl)piperazine-1-yl)ethane-1-ol

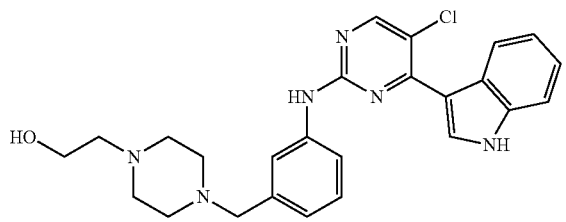 [SMILES: OCCN1CCN(Cc2cccc(Nc3ncc(Cl)c(-c4c[nH]c5ccccc45)n3)c2)CC1]

45 mg (0.19 mmol) of 2-(4-(3-aminobenzyl)piperazine-1-yl)ethane-1-ol prepared in Step 5) and 50 mg (0.19 mmol) of 3-(2,5-dichloropyrimidine-4-yl)-1H-indole (prepared according to WO 2013-014448) were dissolved in 2-butanol, and 36 mg (0.19 mmol) of p-toluenesulfonate (p-TsOH) was added thereto. This reaction mixture was stirred under reflux at a temperature of 120° C. for 4 hours. Once the reaction was complete, the mixture was cooled to room temperature, and a saturated sodium hydrogen carbonate solution was added dropwise thereto, followed by an extraction process using chloromethylene for 2 times. The extracted organic layer was washed with saline water, dried using anhydrous sodium sulfate, and concentrated under reduced pressure. The obtained residue was purified using column chromatography (chloroform:methanol=9:1 (v/v)), and the resulting solution was concentrated under reduced pressure to thereby obtain 31 mg of a desired compound at a yield of 35%.

MS (ESI+, m/z): 463 [M+H]$^+$ $^1$H-NMR (300 MHz, DMSO-$d_6$): δ11.89 (bs, 1H), 9.58 (s, 1H), 8.55 (d, 1H), 8.48 (m, 2H), 7.70 (m, 2H), 7.49 (d, 1H), 7.20 (m, 2H), 7.12 (t, 1H), 6.91 (d, 1H), 4.32 (m, 1H), 3.66 (m, 5H), 2.34 (m, 9H).

Example 35: 2-(4-(3-((5-chloro-4-(6-fluoro-1H-indole-3-yl)pyrimidine-2-yl)amino)-5-methoxybenzyl)piperazine-1-yl)ethane-1-ol

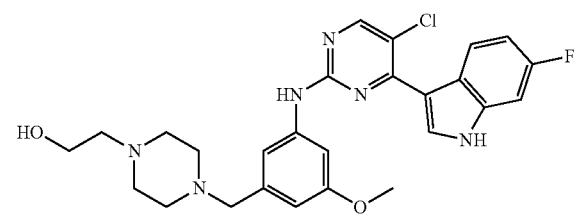 [SMILES: COc1cc(CN2CCN(CCO)CC2)cc(Nc2ncc(Cl)c(-c3c[nH]c4cc(F)ccc34)n2)c1]

79 mg of a desired compound was obtained at a yield of 59% in substantially the same manner as in Step 6) of Example 35, except that 63 mg (0.24 mmol) of 2-(4-(3-amino-5-methoxybenzyl)piperazine-1-yl)ethane-1-ol was used instead of 2-(4-(3-aminobenzyl)piperazine-1-yl)ethane-1-ol, and 68 mg (0.24 mmol) of 3-(2,5-dichloropyrimidine-4-yl)-6-fluoro-1H-indole was used instead of 3-(2,5-dichloropyrimidine-4-yl)-1H-indole in Step 6) of Example 35.

MS (ESI+, m/z): 511 [M+H]$^+$ $^1$H-NMR (300 MHz, DMSO-$d_6$): δ11.96 (bs, 1H), 9.62 (s, 1H), 8.63 (m, 1H), 8.51 (d, 1H), 8.48 (s, 1H), 7.38 (s, 1H), 7.25 (m, 2H), 6.93 (m, 1H), 6.51 (s, 1H), 4.35 (t, 1H), 3.69 (s, 3H), 3.37 (m, 4H), 2.32 (m, 10H).

Example 36: 2-(4-(3-((5-chloro-4-(6-fluoro-1H-indole-3-yl)pyrimidine-2-yl)amino)benzyl)piperazine-1-yl)ethane-1-ol

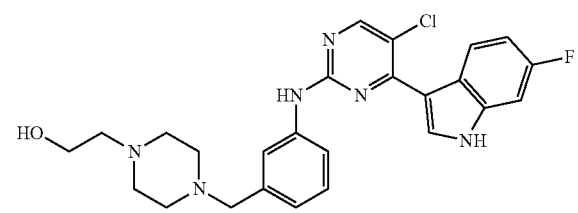 [SMILES: OCCN1CCN(Cc2cccc(Nc3ncc(Cl)c(-c4c[nH]c5cc(F)ccc45)n3)c2)CC1]

53 mg of a desired compound was obtained at a yield of 52% in substantially the same manner as in Step 6) of Example 35, except that 59 mg (0.21 mmol) of 3-(2,5- dichloropyrimidine-4-yl)-6-fluoro-1H-indole was used instead of 3-(2,5-dichloropyrimidine-4-yl)-1H-indole in Step 6) of Example 35.

MS (ESI+, m/z): 481 [M+H]$^+$ $^1$H-NMR (300 MHz, DMSO-d$_6$): δ 11.94 (bs, 1H), 9.62 (s, 1H), 8.61 (m, 1H), 8.57 (m, 1H), 7.69 (m, 2H), 7.25 (m, 2H), 6.94 (m, 2H), 4.34 (m, 1H), 3.46 (m, 5H), 2.32 (m, 9H).

Example 37: 2-(4-(3-((5-chloro-4-(1H-indole-3-yl)pyrimidine-2-yl)amino)-5-methoxybenzyl)piperazine-1-yl)ethane-1-ol

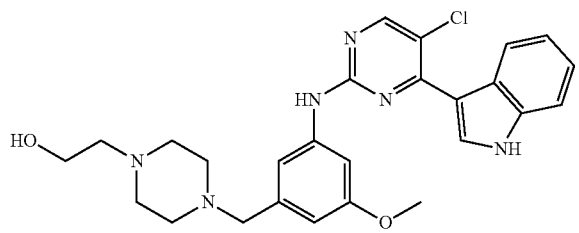 [SMILES: COc1cc(CN2CCN(CCO)CC2)cc(Nc2ncc(Cl)c(-c3c[nH]c4ccccc34)n2)c1]

44 mg of a desired compound was obtained at a yield of 47% in substantially the same manner as in Step 6) of Example 35, except that 50 mg (0.19 mmol) of 2-(4-(3-amino-5-methoxybenzyl)piperazine-1-yl)ethane-1-ol was used instead of 2-(4-(3-aminobenzyl)piperazine-1-yl)ethane-1-ol in Step 6) of Example 35.

MS (ESI+, m/z): 493 [M+H]$^+$ $^1$H-NMR (300 MHz, DMSO-d$_6$): δ11.89 (bs, 1H), 9.56 (s, 1H), 8.60 (d, 1H), 8.48 (m, 2H), 7.49 (d, 1H), 7.38 (s, 1H), 7.37 (m, 3H), 6.49 (s, 1H), 4.33 (m, 1H), 3.66 (s, 2H), 3.40 (m, 5H), 2.32 (m, 9H).

Example 38: 2-(4-(3-((5-chloro-4-(1H-indole-3-yl)pyrimidine-2-yl)amino)-5-cyclopropyl benzyl) piperazine-1-yl)-2-methylpropane-1-ol

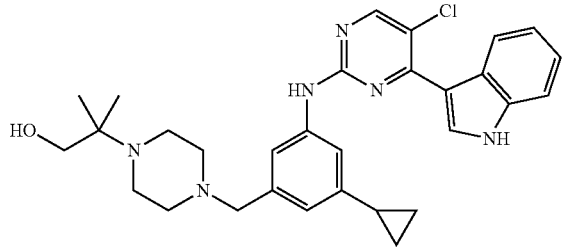 [SMILES: CC(C)(CO)N1CCN(Cc2cc(Nc3ncc(Cl)c(-c4c[nH]c5ccccc45)n3)cc(C3CC3)c2)CC1]

31 mg of a desired compound was obtained at a yield of 45% in substantially the same manner as in Step 6) of Example 35, except that 40 mg (0.13 mmol) of 2-(4-(3-amino-5-cyclopropylbenzyl)piperazine-1-yl)-2-methylpropane-1-ol was used instead of 2-(4-(3-aminobenzyl)piperazine-1-yl)ethane-1-ol in Step 6) of Example 35.

MS (ESI+, m/z): 531 [M+H]$^+$ $^1$H-NMR (300 MHz, DMSO-d6): δ11.92 (s, 1H), 9.50 (s, 1H), 8.59 (d, 1H), 8.50 (d, 1H), 8.45 (s, 1H), 7.51 (m, 3H), 7.22 (t, 1H), 7.12 (t, 1H), 6.63 (s, 1H), 3.77 (m, 1H), 3.24 (bs, 2H), 2.33 (bs, 4H), 1.85 (m, 1H), 1.23 (m, 2H), 0.92 (m, 10H), 0.61 (m, 2H).

Example 39: (S)-1-((1-(3-((5-chloro-4-(1H-indole-3-yl)pyrimidine-2-yl)amino)-5-cyclopropylbenzyl)piperidine-4-yl)(methyl)amino)propane-2-ol

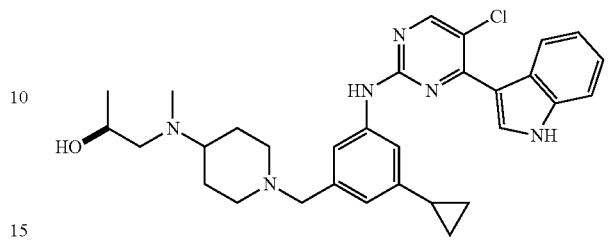

26 mg of a desired compound was obtained at a yield of 30% in substantially the same manner as in Step 6) of Example 35, except that 50 mg (0.16 mmol) of (S)-1-((1-(3-amino-5-cyclopropylbenzyl)piperidine-4-yl)(methyl)amino)propane-2-ol was used instead of 2-(4-(3-aminobenzyl)piperazine-1-yl)ethane-1-ol in Step 6) of Example 35.

MS (ESI+, m/z): 545 [M+H]$^+$ $^1$H-NMR (300 MHz, DMSO-d6): δ11.94 (s, 1H), 9.51 (s, 1H), 8.60 (d, 1H), 8.50 (d, 1H), 8.45 (s, 1H), 7.51 (m, 3H), 7.22 (t, 1H), 7.12 (t, 1H), 6.62 (s, 1H), 3.66 (bs, 1H), 3.50 (s, 2H), 2.81 (d, 2H), 2.31 (s, 3H), 1.89 (m, 2H), 1.60 (m, 2H), 1.48 (m, 3H), 1.27 (m, 2H), 1.02 (d, 3H), 0.91 (m, 2H), 0.61 (m, 2H).

Example 40: (S)-1-((1-(3-((5-chloro-4-(6-methyl-1H-indole-3-yl)pyrimidine-2-yl)amino)-5-cyclopropylbenzyl)piperidine-4-yl)(methyl)amino)propane-2-ol

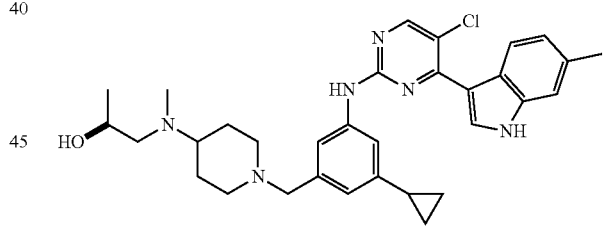

67 mg of a desired compound was obtained at a yield of 75% in substantially the same manner as in Step 6) of Example 35, except that 50 mg (0.16 mmol) of (S)-1-((1-(3-amino-5-cyclopropylbenzyl)piperidine-4-yl)(methyl)amino)propane-2-ol was used instead of 2-(4-(3-aminobenzyl)piperazine-1-yl)ethane-1-ol, and 48 mg (0.17 mmol) of 3-(2,5-dichloropyrimidine-4-yl)-6-methyl-1H-indole was used instead of 3-(2,5-dichloropyrimidine-4-yl)-1H-indole in Step 6) of Example 35.

MS (ESI+, m/z): 559 [M+H]$^+$ $^1$H-NMR (300 MHz, DMSO-d6): δ11.78 (s, 1H), 9.49 (s, 1H), 8.47 (m, 3H), 7.48 (m, 1H), 7.39 (s, 1H), 7.27 (s, 1H), 6.95 (d, 1H), 6.63 (s, 1H), 3.85 (bs, 1H), 3.50 (m, 2H), 2.82 (d, 2H), 2.42 (s, 3H), 2.28 (s, 3H), 1.86 (m, 3H), 1.63 (m, 2H), 1.51 (m, 3H), 1.24 (m, 2H), 1.03 (d, 3H), 0.91 (m, 2H), 0.62 (m, 2H).

Example 41: 2-(4-(3-((5-chloro-4-(6-methyl-1H-indole-3-yl)pyrimidine-2-yl)amino)-5-cyclopropyl-benzyl)piperazine-1-yl)-2-methylpropane-1-ol

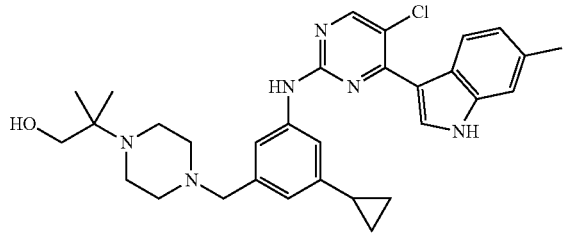 [SMILES: Cc1ccc2c(-c3nc(Nc4cc(CN5CCN(C(C)(C)CO)CC5)cc(C5CC5)c4)ncc3Cl)c[nH]c2c1]

40 mg of a desired compound was obtained at a yield of 52% in substantially the same manner as in Step 6) of Example 35, except that 43 mg (0.14 mmol) of 2-(4-(3-amino-5-cyclopropylbenzyl)piperazine-1-yl)-2-methylpropane-1-ol was used instead of 2-(4-(3-aminobenzyl)piperazine-1-yl)ethane-1-ol, and 43 mg (0.16 mmol) of 3-(2,5-dichloropyrimidine-4-yl)-6-methyl-1H-indole was used instead of 3-(2,5-dichloropyrimidine-4-yl)-1H-indole in Step 6) of Example 35.

MS (ESI+, m/z): 545 [M+H]+

1H-NMR (300 MHz, DMSO-d6): δ 11.77 (s, 1H), 9.47 (s, 1H), 8.46 (m, 3H), 7.44 (s, 1H), 7.38 (s, 1H), 7.27 (s, 1H), 6.95 (d, 1H), 6.62 (s, 1H), 4.56 (m, 1H), 3.64 (s, 2H), 3.37 (m, 4H), 3.16 (m, 2H), 2.41 (s, 3H), 2.33 (m, 4H), 1.78 (m, 1H), 0.91 (m, 8H), 0.62 (m, 2H).

Example 42: (S)-1-(1-(3-((5-chloro-4-(1H-indole-3-yl)pyrimidine-2-yl)amino)-5-cyclopropylbenzyl)piperidine-4-yl)pyrrolidine-3-ol

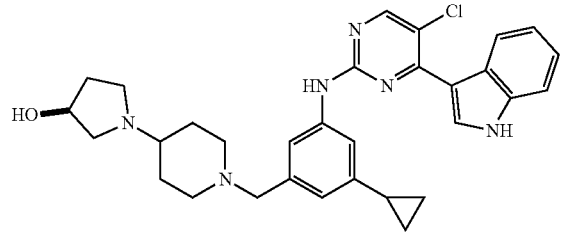 [SMILES: O[C@H]1CCN(C2CCN(Cc3cc(Nc4ncc(Cl)c(-c5c[nH]c6ccccc56)n4)cc(C4CC4)c3)CC2)C1]

60 mg of a desired compound was obtained at a yield of 69% in substantially the same manner as in Step 6) of Example 35, except that 50 mg (0.16 mmol) of (S)-1-(1-(3-amino-5-cyclopropylbenzyl)piperidine-4-yl)pyrrolidine-3-ol was used instead of 2-(4-(3-aminobenzyl)piperazine-1-yl)ethane-1-ol in Step 6) of Example 35.

MS (ESI+, m/z): 543 [M+H]+

1H-NMR (300 MHz, DMSO-d6): δ11.94 (s, 1H), 9.50 (s, 1H), 8.59 (d, 1H), 8.49 (s, 1H), 8.45 (s, 1H), 7.61 (m, 3H), 7.24 (m, 2H), 6.62 (s, 1H), 4.63 (d, 1H), 4.12 (m, 2H), 2.71 (m, 4H), 2.45 (m, 2H), 1.92 (m, 4H), 1.70 (m, 2H), 1.45 (m, 1H), 1.33 (m, 4H), 0.90 (m, 2H), 0.61 (m, 2H).

Example 43: (S)-1-(1-(3-((5-chloro-4-(6-methyl-1H-indole-3-yl)pyrimidine-2-yl)amino)-5-cyclopropyl-benzyl)piperidine-4-yl)pyrrolidine-3-ol

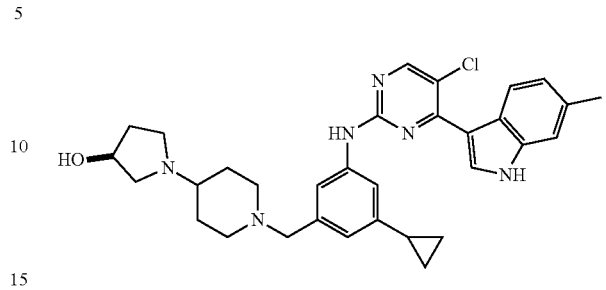

50 mg of a desired compound was obtained at a yield of 56% in substantially the same manner as in Step 6) of Example 35, except that 50 mg (0.16 mmol) of (S)-1-(1-(3-amino-5-cyclopropylbenzyl)piperidine-4-yl)pyrrolidine-3-ol was used instead of 2-(4-(3-aminobenzyl)piperazine-1-yl)ethane-1-ol, and 47 mg (0.17 mmol) of 3-(2,5-dichloropyrimidine-4-yl)-6-methyl-1H-indole was used instead of 3-(2,5-dichloropyrimidine-4-yl)-1H-indole in Step 6) of Example 35.

MS (ESI+, m/z): 557 [M+H]+

1H-NMR (300 MHz, DMSO-d6): δ 11.78 (s, 1H), 9.47 (s, 1H), 8.47 (m, 3H), 7.46 (s, 1H), 7.40 (s, 1H), 7.27 (s, 1H), 6.96 (d, 1H), 6.62 (s, 1H), 4.64 (d, 1H), 4.13 (m, 2H), 3.17 (d, 2H), 2.72 (t, 4H), 2.42 (s, 3H), 2.33 (d, 1H), 1.93 (m, 3H), 1.70 (m, 2H), 1.60 (m, 1H), 1.33 (m, 4H), 0.90 (m, 2H), 0.63 (m, 2H).

Example 44: (S)-1-(1-(3-((5-chloro-4-(6-methoxy-1H-indole-3-yl)pyrimidine-2-yl)amino)-5-cyclopropylbenzyl)piperidine-4-yl)pyrrolidine-3-ol

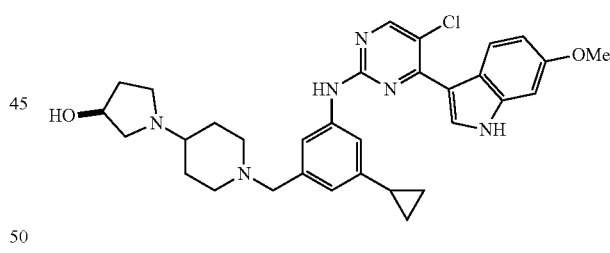

29 mg of a desired compound was obtained at a yield of 30% in substantially the same manner as in Step 6) of Example 35, except that 54 mg (0.17 mmol) of (S)-1-(1-(3-amino-5-cyclopropylbenzyl)piperidine-4-yl)pyrrolidine-3-ol was used instead of 2-(4-(3-aminobenzyl)piperazine-1-yl)ethane-1-ol, and 50 mg (0.17 mmol) of 3-(2,5-dichloropyrimidine-4-yl)-6-methoxy-1H-indole was used instead of 3-(2,5-dichloropyrimidine-4-yl)-1H-indole in Step 6) of Example 35.

MS (ESI+, m/z): 573 [M+H]+

1H-NMR (300 MHz, DMSO-d6): δ 11.71 (s, 1H), 9.45 (s, 1H), 8.49 (m, 3H), 7.41 (d, 2H), 6.97 (s, 1H), 6.75 (d, 1H), 6.62 (s, 1H), 4.62 (s, 1H), 4.33 (s, 1H), 4.12 (s, 1H), 3.79 (s, 3H), 2.72 (m, 4H), 2.25 (m, 1H), 1.89 (m, 4H), 1.70 (m, 2H), 1.45 (m, 1H), 0.95 (m, 4H), 0.90 (m, 2H), 0.61 (m, 2H).

Example 45: 1-(3-((5-chloro-4-(6-methyl-1H-indole-3-yl)pyrimidine-2-yl)amino)-5-cyclopropylbenzyl)piperidine-4-ol

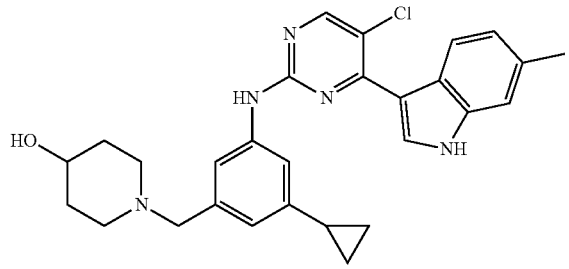 [SMILES: Cc1ccc2c(-c3nc(Nc4cc(CN5CCC(O)CC5)cc(C5CC5)c4)ncc3Cl)c[nH]c2c1]

100 mg of a desired compound was obtained at a yield of 88% in substantially the same manner as in Step 6) of Example 35, except that 57 mg (0.23 mmol) of 1-(3-amino-5-cyclopropylbenzyl)piperidine-4-ol was used instead of 2-(4-(3-aminobenzyl)piperazine-1-yl)ethane-1-ol, and 96 mg (0.35 mmol) of 3-(2,5-dichloropyrimidine-4-yl)-6-methyl-1H-indole was used instead of 3-(2,5-dichloropyrimidine-4-yl)-1H-indole in Step 6) of Example 35.

MS (ESI+, m/z): 488 [M+H]$^+$ $^1$H-NMR (300 MHz, DMSO-$d_6$): δ 11.82 (s, 1H), 9.52 (s, 1H), 8.53 (m, 3H), 7.47 (d, 2H), 7.32 (s, 1H), 6.99 (d, 1H), 6.68 (s, 1H), 4.59 (s, 1H), 3.48 (m, 2H), 2.70 (m, 2H), 2.46 (s, 3H), 2.05 (m, 2H), 1.87 (m, 1H), 1.72 (d, 2H), 1.41 (d, 2H), 0.92 (m, 2H), 0.65 (d, 2H).

Example 46: (S)-5-chloro-N-(3-cyclopropyl-5-((3-(dimethylamino)pyrrolidine-1-yl)methyl)phenyl)-4-(6-methyl-1H-indole-3-yl)pyrimidine-2-amine

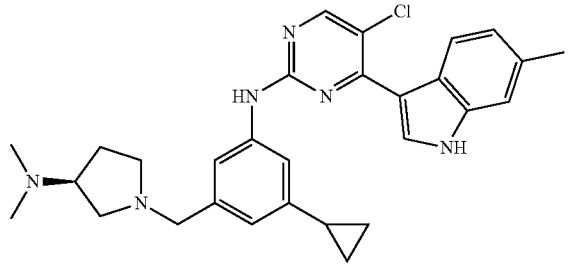

180 mg of a desired compound was obtained at a yield of 96% in substantially the same manner as in Step 6) of Example 35, except that 100 mg (0.37 mmol) of (S)-1-(3-amino-5-cyclopropylbenzyl)-N,N-dimethylpyrrolidine-3-amine was used instead of 2-(4-(3-aminobenzyl)piperazine-1-yl)ethane-1-ol, and 153 mg (0.55 mmol) of 3-(2,5-dichloropyrimidine-4-yl)-6-methyl-1H-indole was used instead of 3-(2,5-dichloropyrimidine-4-yl)-1H-indole in Step 6) of Example 35.

MS (ESI+, m/z): 501 [M+H]$^+$ $^1$H-NMR (300 MHz, DMSO-$d_6$): δ 11.83 (s, 1H), 9.52 (s, 1H), 8.52 (m, 3H), 7.56 (s, 1H), 7.42 (s, 1H), 7.32 (s, 1H), 6.99 (d, 1H), 6.67 (s, 1H), 3.58 (d, 1H), 3.47 (m, 2H), 2.87 (m, 1H), 2.65 (t, 1H), 2.47 (s, 3H), 2.32 (m, 2H), 2.19 (s, 6H), 1.88 (m, 2H), 1.70 (m, 1H), 1.09 (t, 1H), 0.93 (d, 2H), 0.65 (d, 2H).

Example 47: 1-(4-(3-((5-chloro-4-(6-fluoro-1H-indole-3-yl)pyrimidine-2-yl)amino)-5-cyclopropylbenzyl)piperazine-1-yl)-2-hydroxyethane-1-one

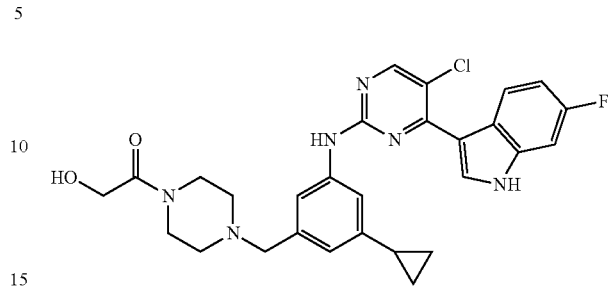

19 mg of a desired compound was obtained at a yield of 19% in substantially the same manner as in Step 6) of Example 35, except that 53 mg (0.18 mmol) of 1-(4-(3-amino-5-cyclopropylbenzyl)piperazine-1-yl)2-hydroxyethane-1-one was used instead of 2-(4-(3-aminobenzyl)piperazine-1-yl)ethane-1-ol, and 51 mg (0.18 mmol) of 3-(2,5-dichloropyrimidine-4-yl)-6-fluoro-1H-indole was used instead of 3-(2,5-dichloropyrimidine-4-yl)-1H-indole in Step 6) of Example 35.

MS (ESI+, m/z): 535 [M+H]$^+$ $^1$H-NMR (300 MHz, DMSO-$d_6$): δ 11.95 (bs, 1H), 9.54 (s, 1H), 8.60 (t, 1H), 8.51 (s, 1H), 8.47 (s, 1H), 7.48 (s, 1H), 7.39 (s, 1H), 7.28 (dd, 1H), 6.92 (m, 1H), 6.66 (s, 1H), 4.50 (t, 1H), 4.04 (d, 1H), 3.40 (bs, 4H), 3.28 (m, 2H), 2.32 (m, 4H), 1.85 (m, 1H), 0.83 (m, 2H), 0.60 (m, 2H).

Example 48: 1-(4-(3-((5-chloro-4-(6-methyl-1H-indole-3-yl)pyrimidine-2-yl)amino)-5-cyclopropylbenzyl)piperazine-1-yl)-2-hydroxyethane-1-one

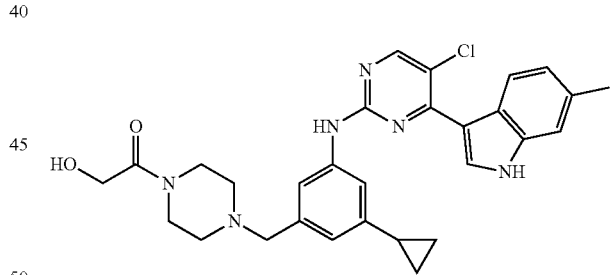

31 mg of a desired compound was obtained at a yield of 32% in substantially the same manner as in Step 6) of Example 35, except that 53 mg (0.18 mmol) of 1-(4-(3-amino-5-cyclopropylbenzyl)piperazine-1-yl)2-hydroxyethane-1-one was used instead of 2-(4-(3-aminobenzyl)piperazine-1-yl)ethane-1-ol, and 56 mg (0.20 mmol) of 3-(2,5-dichloropyrimidine-4-yl)-6-methyl-1H-indole was used instead of 3-(2,5-dichloropyrimidine-4-yl)-1H-indole in Step 6) of Example 35.

MS (ESI+, m/z): 531 [M+H]$^+$ $^1$H-NMR (300 MHz, DMSO-d6): δ11.77 (s, 1H), 9.48 (s, 1H), 8.47 (m, 3H), 7.51 (s, 1H), 7.40 (s, 1H), 7.27 (s, 1H), 6.96 (d, 1H), 6.65 (s, 1H), 4.50 (t, 1H), 4.05 (d, 2H), 3.79 (m, 1H), 3.40 (s, 4H), 3.27 (m, 1H), 2.42 (s, 3H), 2.32 (m, 4H), 1.86 (m, 1H), 0.93 (m, 2H), 0.65 (m, 2H).

Example 49: 2-(4-(3-((5-chloro-4-(6-ethyl-1H-indole-3-yl)pyrimidine-2-yl)amino)-5-cyclopropyl benzyl)piperazine-1-yl)ethane-1-ol

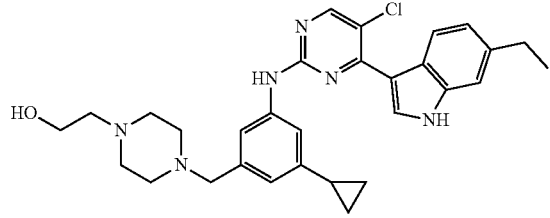 [SMILES: CCc1ccc2c(-c3nc(Nc4cc(CN5CCN(CCO)CC5)cc(C5CC5)c4)ncc3Cl)c[nH]c2c1]

70 mg of a desired compound was obtained at a yield of 65% in substantially the same manner as in Step 6) of Example 35, except that 56 mg (0.20 mmol) of 2-(4-(3-amino-5-cyclopropylbenzyl)piperazine-1-yl)ethane-1-ol was used instead of 2-(4-(3-aminobenzyl)piperazine-1-yl) ethane-1-ol, and 84 mg (0.30 mmol) of 3-(2,5-dichloropyrimidine-4-yl)-6-ethyl-1H-indole was used instead of 3-(2,5-dichloropyrimidine-4-yl)-1H-indole in Step 6) of Example 35.

MS (ESI+, m/z): 531 [M+H]$^+$ $^1$H-NMR (300 MHz, DMSO-d$_6$): δ 11.78 (s, 1H), 9.47 (s, 1H), 8.48 (m, 3H), 7.47 (s, 1H), 7.41 (s, 1H), 7.29 (s, 1H), 6.98 (d, 1H), 6.34 (s, 1H), 4.35 (t, 1H), 3.45 (q, 2H), 2.72 (q, 2H), 2.36 (m, 1H), 1.84 (m, 1H), 1.24 (t, 4H), 0.91 (m, 2H), 0.64 (m, 2H).

Example 50: (3-((5-chloro-4-(1H-indole-3-yl)pyrimidine-2-yl)amino)-5-methoxyphenyl)(4-(2-hydroxyethyl)piperazine-1-yl)methanone

Step 1) Preparation of 3-methoxy-5-nitrobenzoyl chloride

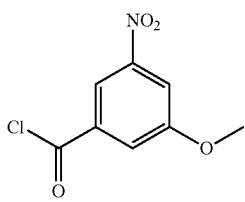

1.0 g (5.07 mmol) of 3-methoxy-5-nitrobenzoate was dissolved in 10 mL of dichloromethane. 0.9 mL (10.14 mmol) of oxalyl chloride and 3 to 4 drops of N, N-dimethylformamide were added thereto. The mixture was stirred at room temperature for 3 hours. Once the reaction was complete, a solvent was removed under reduced pressure to obtained 1.09 g of a desired compound at a yield of 99%.

Step 2) (4-(2-hydroxyethyl)piperazine-1-yl)(3-methoxy-5-nitrophenyl)methanone

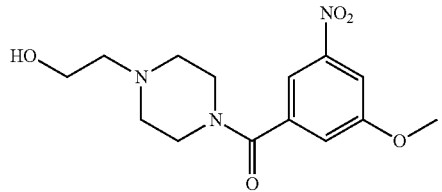

1.09 g (5.06 mmol) 3-methoxy-5-nitrobenzoyl chloride prepared in Step 1) and 2.0 g (15.18 mmol) of 2-(piperazine-1-yl)ethane-1-ol, and 2.1 mL (15.18 mmol) of triethylamine were dissolved in 10 mL of dichloromethane, and then, the mixture was stirred at room temperature for 17 hours. Once the reaction was complete, water and chloroform were added dropwise thereto. An organic layer was separated therefrom and washed with water 2 times. The organic layer was washed with saline water and dried using anhydrous sodium sulfate, followed by removal of a solvent under reduced pressure. The obtained residue was purified using MPLC (chloroform:methanol=20:1 (v/v)), and the resulting solution was concentrated under reduced pressure to thereby obtain 1.08 g of a desired compound at a yield of 69%.

Step 3) (3-amino-5-methoxyphenyl)(4-(2-hydroxyethyl)piperazine-1-yl)methanone

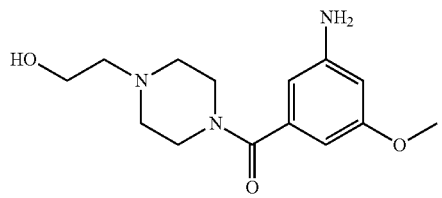 [SMILES: COc1cc(C(=O)N2CCN(CCO)CC2)cc([N+](=O)[O-])c1]

975 mg (17.46 mmol) of iron and 0.12 mL (1.40 mmol) of hydrochloric acid were dissolved in 12 mL of 50% ethanol. The mixture was stirred under reflux at a temperature of 110° C. for 1 hour. 1.08 g (3.49 mmol) of (4-(2-hydroxyethyl)piperazine-1-yl)(3-methoxy-5-nitrophenyl) methanone prepared in Step 2) was slowly added thereto. This mixture was stirred under reflux at a temperature of 110° C. for 1 hour. Once the reaction was complete, the mixture was cooled to room temperature, and then was neutralized using a saturated sodium hydrogen carbonate aqueous solution. A filtration process was performed thereon using a celite filter. Subsequently, a washing process was performed thereon using chloroform and methanol. An organic layer was separated therefrom, which was then dried using anhydrous sodium sulfate and concentrated under reduced pressure. The obtained residue was purified using MPLC (chloroform:methanol=8:1 (v/v)), and the resulting solution was concentrated under reduced pressure to thereby obtain 806 mg of a desired compound at a yield of 83%.

$^1$H-NMR (300 MHz, DMSO-d$_6$): δ6.13 (s, 1H), 6.07 (s, 1H), 5.97 (s, 1H), 5.23 (bs, 2H), 3.62 (s, 3H), 3.49 (m, 4H), 2.38 (m, 6H).

Step 4) (3-((5-chloro-4-(1H-indole-3-yl)pyrimidine-2-yl)amino)-5-methoxyphenyl)(4-(2-hydroxyethyl)iperazine-1-yl)methanone

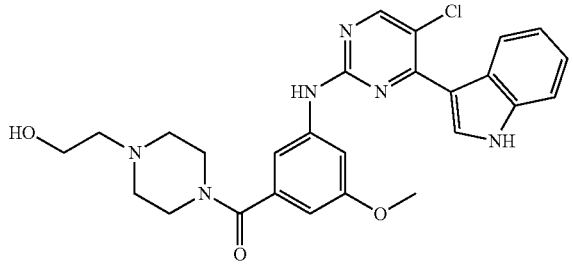 [SMILES: COc1cc(Nc2ncc(Cl)c(-c3c[nH]c4ccccc34)n2)cc(C(=O)N2CCN(CCO)CC2)c1]

53 mg (0.19 mmol) of (3-amino-5-methoxyphenyl)(4-(2-hydroxyethyl)piperazine-1-yl)methanone prepared in Step 3), 50 mg (0.19 mmol) of 3-(2,5-dichloropyrimidine-4-yl)-6-methyl-1H-indole, and 36 mg (0.19 mmol of p-toluenesulfonic acid monohydrate were dissolved in 1.2 mL of 2-butanol. Then, the mixture was stirred at a temperature of 120° C. in a sealed tube for 17 hours. Once the reaction was complete, the mixture was cooled to room temperature, and then, chloroform, methanol, and saturated sodium hydrogen carbonate were added thereto. An organic layer was separated therefrom, which was then dried using anhydrous sodium sulfate and concentrated under reduced pressure. The obtained residue was purified using MPLC (chloroform:methanol=7:1 (v/v)), and the resulting solution was concentrated under reduced pressure to thereby obtain 25 mg of a desired compound at a yield of 26%.

MS (ESI+, m/z): 507 [M+H]$^+$ $^1$H-NMR (300 MHz, DMSO-d$_6$): δ11.93 (bs, 1H), 9.76 (s, 1H), 8.56 (m, 1H), 8.49 (s, 2H), 7.48 (m, 3H), 7.23 (m, 1H), 7.13 (m, 1H), 6.50 (s, 1H), 4.41 (m, 1H), 3.50 (s, 3H), 3.46-3.34 (m, 6H), 2.46 (m, 6H).

Example 51: 1-(2-(3-((5-chloro-4-(6-methyl-1H-indole-3-yl)pyrimidine-2-yl)amino)-5-cyclopropyl-phenoxy)ethyl)piperidine-4-ol Step 1) 2-amino-3-bromo-5-nitrophenol

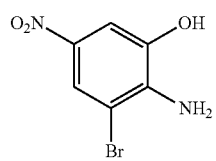 [SMILES: Nc1c(O)cc([N+](=O)[O-])cc1Br]

25 g (162 mmol) of 2-amino-5-nitrophenol was dissolved in 1.0 L of acetonitrile, and 28.8 g (170 mmol) of N-bromosuccinimide was slowly added thereto. The mixture was stirred at room temperature for 2 hours, and a solvent was removed therefrom under reduced pressure. The result was stirred in a mixture solution of ethyl acetate and hexane (1:1). The obtained solid underwent a filtration process to thereby obtain 31.5 g of a desired compound at a yield of 83%.

$^1$H-NMR (300 MHz, DMSO-d$_6$): δ 10.66 (s, 1H), 7.83 (s, 1H), 7.46 (s, 1H), 6.15 (s, 2H).

Step 2) Preparation of 3-bromo-5-nitrophenol

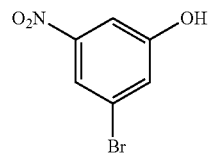 [SMILES: O=[N+]([O-])c1cc(O)cc(Br)c1]

75.6 g (0.32 mmol) of 2-amino-3-bromo-5-nitrophenol prepared in Step 1) was dissolved in 1.5 L of ethanol. The mixture was cooled to a temperature of −10° C. 62.3 mL (1.17 mmol) of sulfuric acid was added thereto at a temperature in a range of −10° C. to −2° C. for 30 minutes. The temperature of the reaction mixture was raised to 50° C., and sodium nitrite was slowly added thereto for 30 minutes. The temperature of the reaction mixture was raised to 80° C. and the mixture was stirred under reflux for 3 hours. Once the reaction was complete, a solvent was removed therefrom under reduced pressure, and water and ethyl acetate were added dropwise thereto. An organic layer was extracted therefrom three times, and then washed with saline water. The organic layer was dried using anhydrous sodium sulfate, and then concentrated under reduced pressure. The obtained residue was purified using column chromatography (ethyl acetate:hexane=0.5:10 (v/v)), and the resulting solution was concentrated under reduced pressure to thereby obtain 60 g of a desired compound at a yield of 85%.

$^1$H-NMR (300 MHz, DMSO-d$_6$): δ 10.90 (s, 1H), 7.75 (s, 1H), 7.51 (s, 1H), 7.36 (s, 1H).

Step 3) Preparation of 3-cyclo-5-nitrophenol

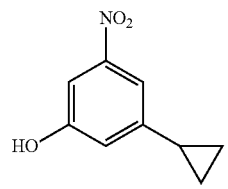 [SMILES: O=[N+]([O-])c1cc(O)cc(C2CC2)c1]

3.0 g (13.76 mmol) of 3-bromo-5-nitrophenol prepared in Step 2), 3.54 g (41.28 mmol) of cyclopropylboronic acid, 8.8 g (41.28 mmol) of potassium phosphate, 310 mg (1.38 mmol) of palladium(II) acetate, and 1.1 g (4.13 mmol) of triphenylphosphine were dissolved in a mixture of 30 mL of toluene and 15 mL of water, followed by stirring under reflux at a temperature of 100° C. for 16 hours. Once the reaction was complete, the mixture was cooled to room temperature, and the mixture was filtered using a celite filter. The resultant was washed with chloroform. An organic layer was separated therefrom, washed with water 2 times, and dried using anhydrous sodium sulfate, followed by removal of a solvent under reduced pressure. The obtained residue was purified using MPLC (chloroform:methanol=20:1 (v/v)), and the resulting solution was concentrated under reduced pressure to thereby obtain 1.52 g of a desired compound at a yield of 62%.

$^1$H-NMR (300 MHz, DMSO-d$_6$): δ 10.32 (s, 1H), 7.34 (s, 1H), 7.29 (s, 1H), 6.86 (s, 1H), 1.99 (m, 1H), 0.98 (m, 2H), 0.70 (m, 2H).

Step 4) Preparation of 1-(2-(3-cyclopropyl-5-nitrophenoxy)ethyl)piperidine-4-ol

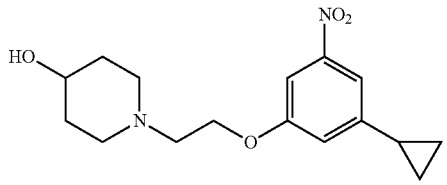

500 mg (2.79 mmol) of 3-cyclo-5-nitrophenol prepared in Step 3) and 0.37 mL (4.19 mmol) of 1,2-dibromoethane were dissolved in 7 mL of acetonitrile, followed by addition of 2.7 g (8.37 mmol) of cesium carbonate. The reaction mixture was stirred at room temperature for 24 hours. Once the reaction was complete, water and ethyl acetate were added dropwise thereto. An organic layer was extracted therefrom, and the organic layer was washed with saline water, dried using anhydrous sodium sulfate, and concentrated under reduced pressure. The obtained residue was dissolved in 10 mL of acetonitrile, followed by addition of 544 mg (5.38 mmol) of 4-hydroxypiperidine and 745 mg (5.38 mmol) of potassium carbonate. The temperature of the reaction mixture was raised to 90° C. and the mixture was stirred under reflux for 4 hours. Once the reaction was complete, water and ethyl acetate were added dropwise thereto. An organic layer was separated therefrom and washed with water 2 times. The organic layer was washed with saline water and dried using anhydrous sodium sulfate, followed by removal of a solvent under reduced pressure. The obtained residue was purified using column chromatography (dichloromethane:methanol=10:1 (v/v)), and the resulting solution was concentrated under reduced pressure to thereby obtain 464 mg of a desired compound at a yield of 56%.

$^1$H-NMR (300 MHz, DMSO-$d_6$): δ7.47 (m, 2H), 7.07 (s, 1H), 4.52 (s, 1), 4.13 (m, 2H), 3.41 (m, 1H), 2.77 (m, 2H), 2.63 (m, 2H), 2.09 (m, 3H), 1.80 (m, 2H), 1.36 (m, 2H), 1.01 (m, 2H), 0.79 (m, 2H).

Step 5) Preparation of 1-(2-(3-amino-5-cyclopropylphenoxy)ethyl)piperidine-4-ol

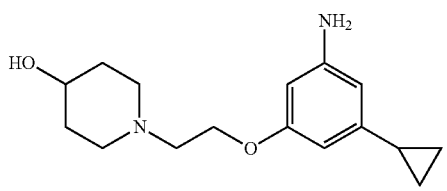 [SMILES: O=[N+]([O-])c1cc(OCCN2CCC(O)CC2)cc(C2CC2)c1]

464 mg (1.51 mmol) of 1-(2-(3-cyclopropyl-5-nitrophenoxy)ethyl)piperidine-4-ol prepared in Step 4) was dissolved in 10 mL of methanol, followed by addition of 50 mg (10%) of Pd/C. Under hydrogen gas atmosphere, the mixture was stirred for 3 hours. Once the reaction was complete, a filtration process was performed thereon using a celite filter, and the filtrate was removed under reduced pressure to obtain 429 mg of a desired compound at a yield of 99%.

Step 6) Preparation of 1-(2-(3-((5-chloro-4-(6-methyl-1H-indol-3-yl)pyrimidine-2-yl)amino)-5-cyclopropylphenoxy)ethyl)piperidine-4-ol

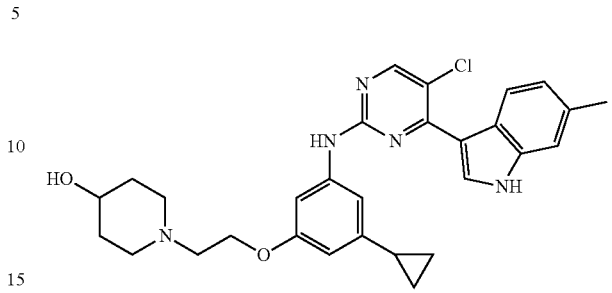

100 mg (0.36 mmol) of 1-(2-(3-amino-5-cyclopropylphenoxy)ethyl)piperidine-4-ol prepared in Step 5) and 151 mg (0.54 mmol) of 3-(2,5-dichloropyrimidine-4-yl)-6-methyl-1H-indole were dissolved in 2-butanol, followed by addition of 103 mg (0.54 mmol) of p-TsOH thereto. This reaction mixture was stirred under reflux at a temperature of 120° C. for 3 hours. Once the reaction was complete, the mixture was cooled to room temperature, and a saturated sodium hydrogen carbonate solution was added dropwise thereto, followed by an extraction process using chloromethylene for 2 times. The extracted organic layer was washed with saline water, dried using anhydrous sodium sulfate, and concentrated under reduced pressure. The obtained residue was purified using column chromatography (chloroform:methanol=9:1 (v/v)), and the resulting solution was concentrated under reduced pressure to thereby obtain 105 mg of a desired compound at a yield of 56%.

MS (ESI+, m/z): 518 [M+H]$^+$ $^1$H-NMR (300 MHz, DMSO-$d_6$): δ11.77 (s, 1H), 9.46 (s, 1H), 8.48 (m, 3H), 7.29 (d, 2H), 7.04 (s, 1H), 6.95 (d, 1H), 6.25 (s, 1H), 4.52 (d, 1H), 3.93 (t, 2H), 3.43-3.32 (m, 1H), 2.64 (m, 2H), 2.58 (t, 2H), 2.43 (s, 3H), 2.05 (m, 2H), 1.81 (m, 1H), 1.67 (d, 2H), 1.34 (m, 2H), 0.89 (m, 2H), 0.67 (m, 2H).

Example 52: 1-(2-(3-((5-chloro-4-(6-methyl-1H-indole-3-yl)pyrimidine-2-yl)amino-5-ethylphenoxy)ethyl)piperidine-4-ol

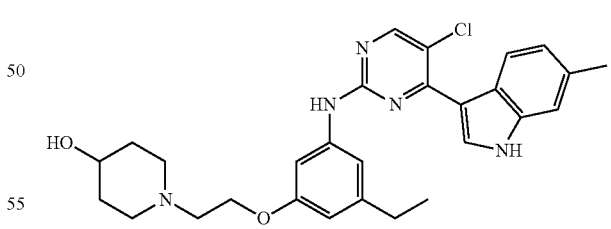

150 mg of a desired compound was obtained at a yield of 79% in substantially the same manner as in Step 6) of Example 51, except that 100 mg (0.38 mmol) of 1-2-(3-amino-5-ethylphenoxy)ethyl)piperidine-4-ol was used instead of 1-(2-(3-amino-5-cyclopropylphenoxy)ethyl)piperidine-4-ol in Step 6) of Example 51.

MS (ESI+, m/z): 518 [M+H]$^+$ $^1$H-NMR (300 MHz, DMSO-$d_6$): δ11.77 (s, 1H), 9.50 (s, 1H), 8.48 (m, 3H), 7.30 (d, 2H), 7.19 (s, 1H), 6.94 (d, 1H), 6.42 (s, 1H), 4.53 (d, 1H), 3.95 (t, 2H), 3.42 (m, 1H), 2.72

(m, 2H), 2.60 (m, 2H), 2.54 (m, 2H), 2.06 (m, 2H), 1.69 (m, 2H), 1.39 (m, 2H), 1.16 (t, 3H).

Example 53: (R)-2-(3-(3-((5-chloro-4-(6-methyl-1H-indole-3-yl)pyrimidine-2-yl)amino)-5-cyclopropylphenoxy)pyrrolidine-1-yl)ethane-1-ol Step 1) Preparation of turt-butyl (R)-3-(3-cyclopropyl-5-nitrophenoxy)pyrrolidine-1-carboxylate

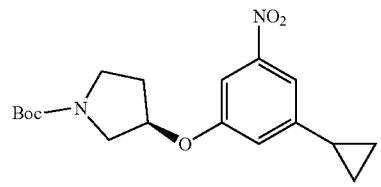 [SMILES: CC(C)(C)OC(=O)N1CC[C@@H](Oc2cc(C3CC3)cc([N+](=O)[O-])c2)C1]

3.0 g (16.74 mmol) of 3-cyclo-5-nitrophenol prepared in Step 3) of Example 51, 5.3 g (20.09 mmol) of turt-butyl (S)-3-((methylsulfonyl)oxy)pyrrolidine-1-carboxylate, and 11.0 g (33.49 mmol) of cesium carbonate were dissolved in 80 mL of N, N-dimethylformamide, followed by stirring at a temperature of 100° C. for 14 hours. Once the reaction was complete, the resultant was cooled to room temperature, and water and ethyl acetate were added dropwise thereto. An organic layer was extracted therefrom, and the organic layer was washed with saline water, dried using anhydrous sodium sulfate, and concentrated under reduced pressure. The obtained residue was purified using column chromatography (chloroform:methanol=9:1 (v/v)), and the resulting solution was concentrated under reduced pressure to thereby obtain 3.9 g of a desired compound at a yield of 67%.

Step 2) Preparation of (R)-2-(3-(3-cyclopropyl-5-nitrophenoxy)pyrrolidine-yl)ethane-1-ol

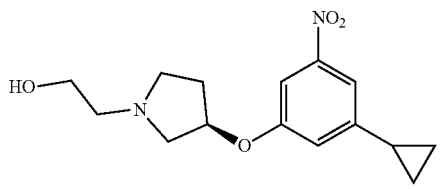 [SMILES: Nc1cc(O[C@@H]2CCN(CCO)C2)cc(C2CC2)c1]

3.9 g (11.19 mmol) of turt-butyl (R)-3-(3-cyclopropyl-5-nitrophenoxy)pyrrolidine-1-carboxylate prepared in Step 1) was dissolved in 40 mL of dichloromethane, followed by dropwise addition of 12 mL of trifluoroacetic acid thereto. The reaction mixture was stirred at room temperature for 1 hours. Once the reaction was complete, an organic solvent was concentrated under reduced pressure. The obtained residue, 1.65 mL (22.38 mmol) of bromoethanol, and 8.6 mL (61.55 mmol) of triethylamine were dissolved in 30 mL of N, N-dimethylformamide. The mixture was stirred at room temperature for 17 hours. Once the reaction was complete, the resultant was cooled to room temperature, and water and ethyl acetate were added dropwise thereto. An organic layer was separated therefrom and washed with water 2 times. The organic layer was washed with saline water and dried using anhydrous sodium sulfate, followed by removal of a solvent under reduced pressure. The obtained residue was purified using column chromatography (dichloromethane:methanol=20:1 (v/v)), and the resulting solution was concentrated under reduced pressure to thereby obtain 1.8 g of a desired compound at a yield of 55%.

$^1$H-NMR (300 MHz, DMSO-$d_6$): δ 7.47 (s, 1H), 7.37 (m, 1H), 7.02 (s, 1H), 4.97 (m, 1H), 4.43 (m, 1H), 3.45 (m, 2H), 2.81 (m, 1H), 2.71 (m, 2H), 2.04 (m, 1H), 2.20 (m, 1H), 2.06 (m, 1H), 1.75 (m, 1H), 1.01 (m, 2H), 0.77 (m, 2H).

Step 3) Preparation of (R)-2-(3-(3-amino-5-cyclopropylphenoxy)pyrrolidine-yl)ethane-1-ol

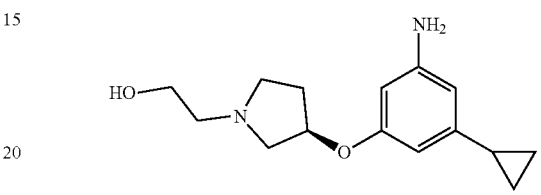

1.7 g (30.79 mmol) of iron and 0.21 mL (2.46 mmol) of hydrochloric acid were dissolved in 20 mL of 50% ethanol. The mixture was stirred under reflux at a temperature of 110° C. for 1 hour. 1.8 g (6.16 mmol) of (R)-2-(3-(3-cyclopropyl-5-nitrophenoxy)pyrrolidine-yl)ethane-1-ol prepared in Step 2) was slowly added thereto. This mixture was stirred under reflux at a temperature of 110° C. for 1 hour. Once the reaction was complete, the mixture was cooled to room temperature, and then was neutralized using a saturated sodium hydrogen carbonate aqueous solution. A filtration process was performed thereon using a celite filter. Subsequently, a washing process was performed thereon using chloroform and methanol. An organic layer was separated therefrom, which was then dried using anhydrous sodium sulfate and concentrated under reduced pressure. The obtained residue was purified using MPLC (chloroform:methanol=8:1 (v/v)), and the resulting solution was concentrated under reduced pressure to thereby obtain 1.48 g of a desired compound at a yield of 87%.

$^1$H-NMR (300 MHz, DMSO-$d_6$): δ5.83 (m, 2H), 5.71 (s, 1H), 4.88 (brs, 2H), 4.64 (m, 1H), 4.41 (m, 1H), 3.45 (m, 2H), 2.75 (m, 1H), 2.60 (m, 1H), 2.45 (m, 2H), 2.10 (m, 1H), 1.66 (m, 2H), 0.79 (m, 2H), 0.51 (m, 2H).

Step 4) Preparation of (R)-2-(3-(3-((5-chloro-4-(6-methyl-1H-indole-3-yl)pyrimidine-2-yl)amino)-5-cyclopropylphenoxy)pyrrolidine-1-yl)ethane-1-ol

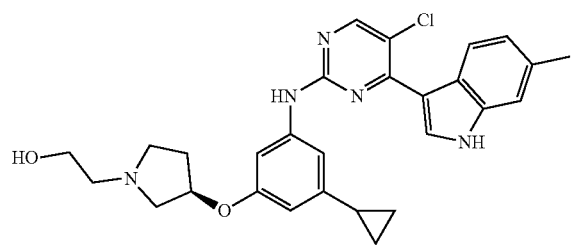 [SMILES: Cc1ccc2c(-c3nc(Nc4cc(O[C@@H]5CCN(CCO)C5)cc(C5CC5)c4)ncc3Cl)c[nH]c2c1]

195 mg of a desired compound was obtained at a yield of 44% in substantially the same manner as in Step 6) of Example 51, except that 230 mg (0.88 mmol) of (R)-2-(3-(3-amino-5-cyclopropylphenoxy)pyrrolidine-1-yl)ethane-1- ol was used instead of 1-(2-(3-amino-5-cyclophenoxy)ethyl) piperidine-4-ol in Step 6) of Example 51.

MS (ESI+, m/z): 504 [M+H]+

$^1$H-NMR (300 MHz, DMSO-d$_6$): δ11.76 (bs, 1H), 9.54 (s, 1H), 8.45 (m, 3H), 7.46 (s, 2H), 7.26 (s, 1H), 7.09 (m, 1H), 6.16 (s, 1H), 4.74 (m, 1H), 4.49 (m, 1H), 3.48 (m, 2H), 2.69 (m, 4H), 2.40 (s, 3H), 2.26 (m, 1H), 1.78 (m, 2H), 0.88 (m, 2H), 0.61 (m, 2H).

Example 54: Preparation of 2-(4-(3-((5-chloro-4-(6-methyl-1H-indole-3-yl)pyrimidine-2-yl)amino)-5-cyclopropylphenoxy)piperidine-1-yl)ethane-1-ol

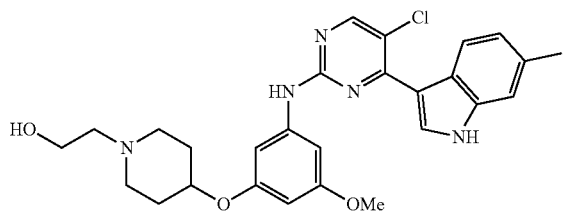 [SMILES: COc1cc(Nc2ncc(Cl)c(-c3c[nH]c4cc(C)ccc34)n2)cc(OC2CCN(CCO)CC2)c1]

185 mg of a desired compound was obtained at a yield of 40% in substantially the same manner as in Step 4) of Example 53, except that 250 mg (0.90 mmol) of 2-(4-(3-amino-5-cyclopropylphenoxy)piperidine-1-yl)ethane-1-ol was used instead of (R)-2-(3-(3-amino-5-cyclopropylphenoxy)pyrrolidine-yl)ethane-1-ol in Step 4) of Example 53.

MS (ESI+, m/z): 518 [M+H]+

$^1$H-NMR (300 MHz, DMSO-d$_6$): δ11.77 (bs, 1H), 9.53 (s, 1H), 8.40 (m, 3H), 7.46 (s, 1H), 7.43 (s, 1H), 7.10 (m, 2H), 6.22 (s, 1H), 4.53 (m, 1H), 3.46 (m, 2H), 2.40 (s, 3H), 1.81 (m, 4H), 1.78 (m, 2H), 0.88 (m, 2H), 0.61 (m, 2H).

Example 55: Preparation of 2-(4-(3-((5-chloro-4-(1H-indole-3-yl)pyrimidine-2-yl)amino)-5-methoxyphenoxy)piperidine-1-yl)ethane-1-ol

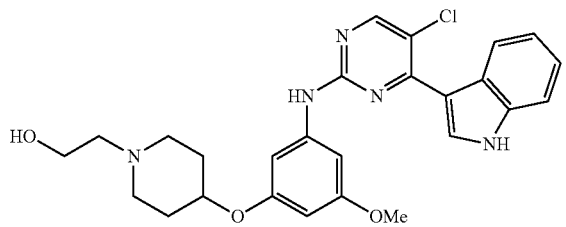 [SMILES: COc1cc(Nc2ncc(Cl)c(-c3c[nH]c4ccccc34)n2)cc(OC2CCN(CCO)CC2)c1]

81 mg of a desired compound was obtained at a yield of 40% in substantially the same manner as in Step 4) of Example 53, except that 110 mg (0.41 mmol) of 2-(4-(3-amino-5-methoxyphenoxy)piperidine-1-yl)ethane-1-ol was used instead of (R)-2-(3-(3-amino-5-cyclopropylphenoxy)pyrrolidine-yl)ethane-1-ol in Step 4) of Example 53.

MS (ESI+, m/z): 494 [M+H]+

$^1$H-NMR (300 MHz, DMSO-d$_6$): δ 11.90 (bs, 1H), 9.53 (s, 1H), 8.53 (d, 1H), 8.45 (m, 2H), 7.50 (m, 1H), 7.18 (m, 3H), 7.07 (s, 1H), 6.11 (s, 1H), 4.19 (m, 1H), 3.64 (s, 3H), 3.47 (m, 2H), 2.70 (m, 2H), 2.39 (m, 1H), 1.96 (m, 2H), 1.21 (m, 2H).

Experimental Examples

The inhibitory activity for kinase and inhibitory activity in cell growth of the foregoing compounds prepared in the Examples were evaluated. The results thereof are as follows.

Experimental Example 1: Evaluation of Inhibitory Activity for Kinase

Inhibitory activity of the exemplary compounds among the foregoing compounds with respect to AXL, CLK2, VEGFR2 (KDR), NUAK1 kinases were measured. Z'-LYTE™ Kinase Assay Kit-Tyr 6 Peptide (Cat. No. PV4122, available from Life Technologies) for AXL, Z'-LYTE™ Kinase Assay Kit-Ser/Thr peptide 6 (Cat. No. PV3179, available from Life Technologies) for CLK2, Z'-LYTE™ Kinase Assay Kit (Cat. No. PV3190, available from Life Technologies) for VEGFR, and Adapta™ Universal Kinase Assay Kit (Cat. No. PV5099, available from Life Technologies) for NUAK1 (ARK5) were used. The experiments were carried out by Life Technologies corporation. The results of activity inhibition (%) at a compound concentration of 100 nM for each kinase are shown in Tables 2 to 5.

TABLE 2

Inhibitory activity (percentage, %) of pyrimidine compound for VEGFR2 kinase

| Compound | Degree of inhibition (%) |
| --- | --- |
| Example 1 | 71 |
| Example 2 | 46 |
| Example 6 | 62 |
| Example 16 | 56 |
| Example 17 | 67 |
| Example 38 | 99 |
| Example 41 | 63 |

TABLE 3

Inhibitory activity (%) of pyrimidine compound for AXL kinase

| Compound | Degree of inhibition (%) |
| --- | --- |
| Example 1 | 52 |
| Example 2 | 56 |
| Example 6 | 49 |
| Example 16 | 27 |
| Example 17 | 66 |
| Example 38 | 51 |
| Example 41 | 50 |

TABLE 4

Inhibitory activity (%) of pyrimidine compound for NUAK1 kinase

| Compound | Degree of inhibition (%) |
| --- | --- |
| Example 1 | 84 |
| Example 2 | 71 |
| Example 6 | 57 |
| Example 16 | 67 |
| Example 17 | 72 |
| Example 38 | 63 |

TABLE 5

| Inhibitory activity (%) of pyrimidine compound for CLK2 kinase | |
|---|---|
| Compound | Degree of inhibition (%) |
| Example 1 | 99 |
| Example 2 | 91 |
| Example 6 | 66 |
| Example 16 | 77 |
| Example 17 | 93 |
| Example 38 | 97 |

Experimental Example 2: Evaluation of Inhibitory Activity in Cell Growth

RS4-11 cell line was incubated in an RPMI1640 culture medium (10% fetal bovine serum (FBS)) at a temperature of 37° C. The incubated cell line was prepared in an amount of 2.0×10$^4$ cells/100 μL, and then plated on 96-well plates. The RPM11640 medium was serially diluted with the test compounds at a concentration in a range of 10 μM to 0.1 nM at a ratio of 1/10. Subsequently, incubation was performed thereon for three days. An MTS test was performed to measure cell viability, and the 50% growth inhibition (GI50) value of the cell line was calculated using GraphPad Prism software. The results thereof are shown in Table 6.

TABLE 6

| Inhibitory activity of pyrimidine compound in cell growth | |
|---|---|
| Compound | GI$_{50}$ (nM) |
| Example 1 | 147 |
| Example 7 | 33 |

MV4-11 cell line was incubated in an IMDM medium (10% FBS) at a temperature of 37° C. The incubated cell line was prepared in an amount of 2×10$^4$ cells/100 μL, and then plated on 96-well plates. The IMDM medium was treated with cascade dilution of the test compounds at a concentration in a range of 1 μM to 0.01 nM at a rate of 1/10. Subsequently, incubation was performed thereon for three days. MTS test was performed to measure cell viability, and the 50% growth inhibition (GI50) value of the cell line was calculated using GraphPad Prism software. The results thereof are shown in Table 7.

TABLE 7

| Inhibitory activity of pyrimidine compound (MV-4-11) in cell growth | |
|---|---|
| Compound | GI$_{50}$ (nM) |
| Example 30 | 0.8 |
| Example 50 | 1.2 |
| Example 52 | 0.8 |
| Example 53 | 1.1 |

As apparent from the foregoing Tables, it was found that the compounds of the present invention exhibit excellent inhibitory activity for kinase and excellent inhibitory activity in cell growth.

While this invention has been particularly shown and described with reference to example embodiments thereof, it will be understood by those skilled in the art that various changes in form and details may be made therein without departing from the spirit and scope of the invention as defined by the appended claims. The example embodiments should be considered in descriptive sense only and not for purposes of limitation. Therefore, the scope of the invention is defined not by the detailed description of the invention but by the claims, and all differences within the scope will be construed as being included in the present invention.

What is claimed is:

1. A compound selected from a substance of Formula 1 and a pharmaceutically acceptable salt thereof:

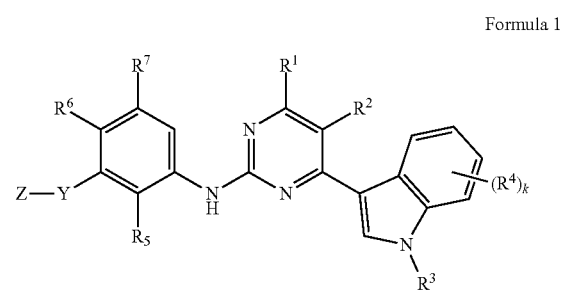

Formula 1 wherein, in Formula 1, $R^1$ is hydrogen, a halogen, a hydroxy group, or a $C_{1-4}$ alkoxy group, $R^2$ is hydrogen, a halogen, a cyano group, a nitro group, an amino group, a carboxamide group, a formyl group, a halo $C_{1-4}$ alkyl group, or a $C_{1-4}$ alkyl group, $R^3$ is hydrogen, a halo $C_{1-4}$ alkyl group, a $C_{1-4}$ alkyl group, a $C_{2-4}$ alkenyl group, or a $C_{2-4}$ alkynyl group, $R^4$(s) are each independently a halogen, a hydroxy group, a cyano group, a nitro group, an amino group, —SR$_c$, —S(=O)R$_c$, —S(=O)$_2$R$_c$, a halo $C_{1-4}$ alkyl group, a $C_{1-4}$ alkoxy group, a hydroxy $C_{1-4}$ alkyl group, a $C_{1-4}$ alkyl group, a $C_{2-4}$ alkenyl group, a $C_{2-4}$ alkynyl group, —NR$_a$R$_b$, —CO$_2$R$_b$, or —CO—NR$_a$R$_b$, wherein, R$_a$ and R$_b$ are each independently hydrogen or a $C_{1-6}$ alkyl group, and R$_c$ is a $C_{1-4}$ alkyl group or —NR$_a$R$_b$, k is an integer from 0 to 4, $R^5$ and $R^6$ are each independently hydrogen, a halogen, a hydroxy group, a nitro group, an amino group, a $C_{1-4}$ alkoxy group, a hydroxy $C_{1-4}$ alkyl group, a $C_{1-4}$ alkyl group, a $C_{2-4}$ alkenyl group, a $C_{2-4}$ alkynyl group, a $C_{3-10}$ cycloalkyl group, or a $C_{3-9}$ heterocycloalkyl group, wherein, the $C_{3-10}$ cycloalkyl group and the $C_{3-9}$ heterocycloalkyl group are each independently unsubstituted or substituted with a halogen, a $C_{1-4}$ alkyl group, or a halo $C_{1-4}$ alkyl group, R7 is a $C_{3-7}$ cycloalkyl group, Y is a direct bond, —(CH$_2$)$_m$—, —O—, —O(CH$_2$)$_m$—, —(CH$_2$)$_m$O—, —C(=O)—, —NR$^9$—, —SO$_2$—, —(CH$_2$)$_m$—O—(CH$_2$)$_n$—, —CO(CH$_2$)$_m$—, —(CH$_2$)$_m$CO—, —(CH$_2$)$_m$—CO—(CH$_2$)$_n$—, —(CH$_2$)$_m$NR$^9$—, —NR$^9$(CH$_2$)$_m$—, —(CH$_2$)$_m$—NR$^9$—(CH$_2$)$_n$—, —(CH$_2$)$_m$SO$_2$—, —SO$_2$(CH$_2$)$_m$—, or —(CH$_2$)$_m$—SO$_2$—(CH$_2$)$_n$—, wherein R$^9$ is hydrogen, a $C_{1-4}$ alkyl group, a $C_{3-10}$ cycloalkyl group, or a $C_{3-9}$ heterocycloalkyl group, and m and n are each independently an integer from 1 to 3, Z is represented by Formula 2:

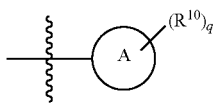

Formula 2 wherein, in Formula 2,
Ⓐ is a $C_{3-10}$ cycloalkyl group or a $C_{2-11}$ heterocycloalkyl group,
$R^{10}$(s) are each independently a halogen, a hydroxy group, a cyano group, a nitro group, an amino group, a thiol group, a formyl group, a linear or branched halo $C_{1-4}$ alkyl group, a linear or branched $C_{1-4}$ alkoxy group, a linear or branched hydroxy $C_{1-4}$ alkyl group, a linear or branched $C_{1-4}$ alkyl group, a linear or branched hydroxy $C_{1-4}$ alkylcarbonyl group, a $C_{2-4}$ alkenyl group, a $C_{2-4}$ alkynyl group, a $C_{3-10}$ cycloalkyl group, a $C_{2-9}$ heterocycloalkyl group, a hydroxy $C_{2-9}$ heterocycloalkyl group, —$NR^{11}R^{12}$, —$COR^{13}$, —$COOR^{13}$, or —$SO_2R^{14}$,
$R^{11}$ and $R^{12}$ are each independently hydrogen, a linear or branched hydroxy $C_{1-4}$ alkyl group, a linear or branched halo $C_{1-4}$ alkyl group, a linear or branched $C_{1-4}$ alkyl group, a $C_{2-4}$ alkenyl group, or a $C_{2-4}$ alkynyl group,
$R^{13}$ is hydrogen, a hydroxy group, a hydroxy $C_{1-4}$ alkyl group, a halo $C_{1-4}$ alkyl group, a $C_{1-4}$ alkyl group, a $C_{2-4}$ alkenyl group, a $C_{2-4}$ alkynyl group, a $C_{3-10}$ cycloalkyl group, or a $C_{2-9}$ heterocycloalkyl group,
$R^{14}$ is a hydroxy group, a halo $C_{1-4}$ alkyl group, a $C_{1-4}$ alkyl group, a $C_{2-4}$ alkenyl group, a $C_{2-4}$ alkynyl group, a $C_{3-10}$ cycloalkyl group, a $C_{2-9}$ heterocycloalkyl group, an aryl group, or —$NR_aR_b$, and
q is an integer from 0 to 5.

2. The compound of claim 1, wherein Y is —$(CH_2)_m$—, —O—, or —C(=O)—.

3. The compound of claim 1, wherein Y is —$CH_2$— or —$(CH_2)_2$—.

4. The compound of claim 1, wherein $R^7$ is a cyclopropyl group.

5. The compound of claim 1, wherein Z is any one selected from Formulae 3 to 5:

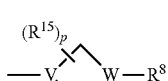

Formula 3

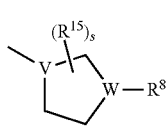

Formula 4

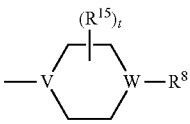

Formula 5 wherein, in Formulae 3 to 5,
V and W are each independently N or CH, provided that at least one of V and W is not CH, $R^8$ is selected from the group consisting of hydrogen, a halogen, a linear or branched $C_{1-4}$ alkyl group, a linear or branched hydroxy $C_{1-4}$ alkyl group, a hydroxy group, —$NR^{11}R^{12}$, a linear or branched hydroxy $C_{1-4}$ alkylcarbonyl group, a heterocycloalkyl group, a hydroxy substituted heterocycloalkyl group, a linear or branched halo $C_{1-4}$ alkyl group, and a linear or branched $C_{1-4}$ alkoxy group,
$R^{11}$ and $R^{12}$ are each independently a hydrogen, a linear or branched $C_{1-4}$ alkyl group, or a linear or branched hydroxy $C_1$-$C_4$ alkyl group,
$R^{15}$(s) are each independently a linear or branched $C_{1-4}$ alkyl group, a linear or branched hydroxy $C_{1-4}$ alkyl group, or a halogen,
p is an integer from 0 to 4, and
s and t are each independently an integer from 0 to 5, provided that $R^8$ is hydrogen, or an integer from 0 to 4, provided that $R^8$ is not hydrogen.

6. The compound of claim 1, wherein
$R^1$ is hydrogen, a hydroxy group, or a $C_{1-4}$ alkoxy group,
$R^2$ is hydrogen, a halogen, a linear or branched $C_{1-4}$ alkyl group, or a linear or branched halo $C_{1-4}$ alkyl group;
$R^3$ is hydrogen,
$R^4$ is a halogen, a hydroxy group, a linear or branched $C_{1-4}$ alkoxy group, a linear or branched hydroxy $C_{1-4}$ alkyl group, or a linear or branched $C_{1-4}$ alkyl group,
k is an integer from 0 to 2,
$R^5$ and $R^6$ are each independently hydrogen or a hydroxy group,
$R^7$ is a cyclopropyl group,
Y is —$(CH_2)_m$—, —$(CH_2)_m$—O—$(CH_2)_n$—, or —$(CH_2)_m$—CO—$(CH_2)_n$—,
Ⓐ is a $C_{3-6}$ heterocycloalkyl group comprising one or two heteroatoms selected from O, N, and S,
$R^{10}$(s) are each independently a hydroxy group, a linear or branched hydroxy $C_{1-4}$ alkyl group, a linear or branched $C_{1-4}$ alkyl group, a $C_{3-10}$ cycloalkyl group, a $C_{2-9}$ heterocycloalkyl group, a hydroxy $C_{2-9}$ heterocycloalkyl group, —$NR^{11}R^{12}$, or —$COR^{13}$,
q is an integer from 0 to 3,
$R^{11}$ and $R^{12}$ are each independently hydrogen, a linear or branched hydroxy $C_{1-4}$ alkyl group, or a linear or branched $C_{1-4}$ alkyl group, and
$R^{13}$ is hydrogen, a linear or branched hydroxy $C_{1-4}$ alkyl group, a linear or branched halo $C_{1-4}$ alkyl group, or a linear or branched $C_{1-4}$ alkyl group.

7. A compound selected from the group consisting of:
1  2-(4-(3-((5-chloro-4-(6-fluoro-1H-indole-3-yl)pyrimidine-2-yl)amino)-5-cyclopropylphenyl)piperazine-1-yl)ethane-1-ol
2  2-(4-(3-((5-chloro-4-(6-methyl-1H-indole-3-yl)pyrimidine-2yl)amino)-5-cyclopropylphenyl)piperazine-1-yl)ethane-1-ol
3  5-chloro-N-(3-cyclopropyl-5-(4-(dimethylamino)piperidine-1-yl)phenyl)-4-(1H-indole-3-yl)pyrimidine-2-amine
4  (S)-1-((1-(3-((5-chloro-4-(1H-indole-3-yl)pyrimidine-2-yl)amino)-5-cyclopropylphenyl)piperidine-4-yl)(methyl)amino)propane-2-ol
5  (S)-1-((1-(3-((5-chloro-4-(6-methyl-1H-indole-3-yl)pyrimidine-2-yl)amino)-5-cyclopropylphenyl)piperidine-4-yl)(methyl)amino)propane-2-ol
6  5-chloro-N-(3-cyclopropyl-5-(4-(dimethylamino)piperidine-1-yl)phenyl)-4-(6-methyl-1H-indole-3-yl)pyrimidine-2-amine 7   2-(4-(3-((5-chloro-4-(6-methoxy-1H-indole-3-yl)pyrimidine-2-yl)amino)-5-cyclopropylphenyl)piperazine-1-yl)ethane-1-ol
8   (S)-1-(1-(3-((5-chloro-4-(1H-indole-3-yl)pyrimidine-2-yl)amino)-5-cyclopropylphenyl)piperidine-4-yl)pyrrolidine-3-ol
9   (S)-1-(1-(3-((5-chloro-4-(6-methyl-1H-indole-3-yl)pyrimidine-2-yl)amino)-5-cyclopropylphenyl)piperidine-4-yl)pyrrolidine-3-ol
10  5-chloro-N-(3-cyclopropyl-5-(4-(dimethylamino)piperidine-1-yl)phenyl)-4-(6-methoxy-1H-indole-3-yl)pyrimidine-2-amine
11  (S)-1-(1-(3-((5-chloro-4-(6-methoxy-1H-indole-3-yl)pyrimidine-2-yl)amino)-5-cyclopropylphenyl)piperidine-4-yl)pyrrolidine-3-ol
12  2-(4-(3-((4-(1H-indole-3-yl)-5-methylpyrimidine-2-yl)amino)-5-cyclopropylphenyl)piperazine-1-yl)ethane-1-ol
13  5-chloro-N-(3-cyclopropyl-5-(4-morpholinopiperidine-1-yl)phenyl)-4-(6-methyl-1H-indole-3-yl)pyrimidine-2-amine
14  5-chloro-N-(3-cyclopropyl-5-(4-(ethyl(methyl)amino)piperidine-1-yl)phenyl)-4-(6-methyl-1H-indole-3-yl)pyrimidine-2-amine
15  5-chloro-N-(3-cyclopropyl-5-(4-(diethylamino)piperidine-1-yl)phenyl)-4-(6-methyl-1H-indole-3-yl)pyrimidine-2-amine
16  5-chloro-N-(3-cyclopropyl-5-(3-(dimethylamino)pyrrolidine-1-yl)phenyl)-4-(6-methyl-1H-indole-3-yl)pyrimidine-2-amine
17  2-(4-(3-((5-chloro-4-(6-methyl-1H-indole-3-yl)pyrimidine-2-yl)amino)-5-cyclopropylphenyl)piperazine-1-yl)-2-methylpropane-1-ol
18  N-(3-(4-aminopiperidine-1-yl)-5-cyclopropylphenyl)-5-chloro-4-(6-methyl-1H-indole-3-yl)pyrimidine-2-amine
19  5-chloro-N-(3-cyclopropyl-5-(4-(methylamino)piperidine-1-yl)phenyl)-4-(6-methyl-1H-indole-3-yl)pyrimidine-2-amine
20  2-(4-(3-((5-chloro-4-(6-fluoro-1H-indole-3-yl)pyrimidine-2-yl)amino)-5-cyclopropylphenyl)piperazine-1-yl)-2-methylpropane-1-ol
21  2-(4-(3-((5-chloro-4-(6-methyl-1H-indole-3-yl)pyrimidine-2-yl)amino)-5-cyclopropylphenyl)piperidine-1-yl)ethane-1-ol
22  2-(4-(3-((5-chloro-4-(6-chloro-1H-indole-3-yl)pyrimidine-2-yl)amino)-5-cyclopropylphenyl)piperazine-1-yl)ethane-1-ol
23  5-chloro-N-(3-cyclopropyl-5-(4-(pyrrolidine-1-yl)piperidine-1-yl)phenyl)-4-(6-methyl-1H-indole-3-yl)pyrimidine-2-amine
24  1-(1-(3-((5-chloro-4-(6-methyl-1H-indole-3-yl)pyrimidine-2-yl)amino)-5-cyclopropylphenyl)piperidine-4-yl)azetidine-3-ol
25  2-(4-(3-((5-chloro-4-(1H-indole-3-yl)pyrimidine-2-yl)amino)-5-methoxyphenyl)piperazine-1-yl)ethane-1-ol
26  2-(4-(3-((5-chloro-4-(6-fluoro-1H-indole-3-yl)pyrimidine-2-yl)amino)phenyl)piperazine-1-yl)ethane-1-ol
27  2-(4-(3-((5-chloro-4-(1H-indole-3-yl)pyrimidine-2-yl)amino)phenyl)piperidine-1-yl)ethane-1-ol
28  2-(4-(3-((5-chloro-4-(1H-indole-3-yl)pyrimidine-2-yl)amino)phenyl) piperazine-1-yl)ethane-1-ol
29  5-chloro-N-(3-(4-(dimethylamino)piperidine-1-yl)phenyl)-4-(1H-indole-3-yl)pyrimidine-2-amine
30  5-chloro-N-(3-(3-(dimethylamino)pyrrolidine-1-yl)phenyl)-4-(1H-indole-3-yl)pyrimidine-2-amine
31  2-(4-(3-((5-chloro-4-(6-fluoro-1H-indole-3-yl)pyrimidine-2-yl)amino)-5-methoxyphenyl)piperazine-1-yl)ethane-1-ol
32  2-(4-(3-((5-chloro-4-(1H-indole-3-yl)pyrimidine-2-yl)amino)-5-isopropoxyphenyl)piperazine-1-yl)ethane-1-ol
33  2-(4-(3-((5-chloro-4-(6-fluoro-1H-indole-3-yl)pyrimidine-2-yl)amino)-5-isopropoxyphenyl)piperazine-1-yl)ethane-1-ol
34  5-chloro-N-(3-cyclopropyl-5-(piperazine-1-ylmethyl)phenyl)-4-(6-fluoro-1H-indole-3-yl)pyrimidine-2-amine
35  2-(4-(3-((5-chloro-4-(6-fluoro-1H-indole-3-yl)pyrimidine-2-yl)amino)-5-methoxybenzyl)piperazine-1-yl)ethane-1-ol
36  2-(4-(3-((5-chloro-4-(6-fluoro-1H-indole-3-yl)pyrimidine-2-yl)amino)benzyl)piperazine-1-yl)ethane-1-ol
37  2-(4-(3-((5-chloro-4-(1H-indole-3-yl)pyrimidine-2-yl)amino)-5-methoxybenzyl)piperazine-1-yl)ethane-1-ol
38  2-(4-(3-((5-chloro-4-(1H-indole-3-yl)pyrimidine-2-yl)amino)-5-cyclopropylbenzyl)piperazine-1-yl)-2-methylpropane-1-ol
39  (S)-1-((1-(3-((5-chloro-4-(1H-indole-3-yl)pyrimidine-2-yl)amino)-5-cyclopropylbenzyl)piperidine-4-yl)(methyl)amino)propane-2-ol
40  (S)-1-((1-(3-((5-chloro-4-(6-methyl-1H-indole-3-yl)pyrimidine-2-yl)amino)-5-cyclopropylbenzyl)piperidine-4-yl)(methyl)amino)propane-2-ol
41  2-(4-(3-((5-chloro-4-(6-methyl-1H-indole-3-yl)pyrimidine-2-yl)amino)-5-cyclopropylbenzyl)piperazine-1-yl)-2-methylpropane-1-ol
42  (S)-1-(1-(3-((5-chloro-4-(1H-indole-3-yl)pyrimidine-2-yl)amino)-5-cyclopropylbenzyl)piperidine-4-yl)pyrrolidine-3-ol
43  (S)-1-(1-(3-((5-chloro-4-(6-methyl-1H-indole-3-yl)pyrimidine-2-yl)amino)-5-cyclopropylbenzyl)piperidine-4-yl)pyrrolidine-3-ol
44  (S)-1-(1-(3-((5-chloro-4-(6-methoxy-1H-indole-3-yl)pyrimidine-2-yl)amino)-5-cyclopropylbenzyl)piperidine-4-yl)pyrrolidine-3-ol
45  1-(3-((5-chloro-4-(6-methyl-1H-indole-3-yl)pyrimidine-2-yl)amino)-5-cyclopropylbenzyl)piperidine-4-ol
46  (S)-5-chloro-N-(3-cyclopropyl-5-((3-(dimethylamino)pyrrolidine-1-yl)methyl)phenyl)-4-(6-methyl-1H-indole-3-yl)pyrimidine-2-amine
47  1-(4-(3-((5-chloro-4-(6-fluoro-1H-indole-3-yl)pyrimidine-2-yl)amino)-5-cyclopropylbenzyl)piperazine-1-yl)-2-hydroxyethane-1-one
48  1-(4-(3-((5-chloro-4-(6-methyl-1H-indole-3-yl)pyrimidine-2-yl)amino)-5-cyclopropylbenzyl)piperazine-1-yl)-2-hydroxyethane-1-one
49  2-(4-(3-((5-chloro-4-(6-ethyl-1H-indole-3-yl)pyrimidine-2-yl)amino)-5-cyclopropylbenzyl)piperazine-1-yl)ethane-1-ol
50  (3-((5-chloro-4-(1H-indole-3-yl)pyrimidine-2-yl)amino)-5-methoxyphenyl)(4-(2-hydroxyethyl)piperazine-1-yl)methanone
51  1-(2-(3-((5-chloro-4-(6-methyl-1H-indole-3-yl)pyrimidine-2-yl)amino)-5-cyclopropylphenoxy)ethyl)piperidine-4-ol
52  1-(2-(3-((5-chloro-4-(6-methyl-1H-indole-3-yl)pyrimidine-2-yl)amino-5-ethylphenoxy)ethyl)piperidine-4-ol
53  (R)-2-(3-(3-((5-chloro-4-(6-methyl-1H-indole-3-yl)pyrimidine-2-yl)amino)-5-cyclopropylphenoxy)pyrrolidine-1-yl)ethane-1-ol 54  2-(4-(3-((5-chloro-4-(6-methyl-1H-indole-3-yl)pyrimidine-2-yl)amino)-5-cyclopropylphenoxy)piperidine-1-yl)ethane-1-ol 55  2-(4-(3-((5-chloro-4-(1H-indole-3-yl)pyrimidine-2-yl)amino)-5-methoxyphenoxy)piperidine-1-yl)ethane-1-ol.

8. The compound of claim 1, wherein
$R^1$, $R^3$, $R^5$, and $R^6$ are each hydrogen,
$R^2$ is hydrogen or a halogen,
$R^4$ is a $C_{1-4}$ alkyl group or a halogen,
Y is a direct bond, —$CH_2$—, —O—, ethyleneoxy, or —C(=O)—, and
Z is any one selected from Formulae 3 to 5:

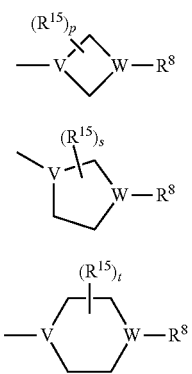

Formula 3

Formula 4

Formula 5 wherein, in Formulae 3 to 5,
V and W are each independently N or CH, provided that at least one of V and W is not CH,
$R^8$ is selected from the group consisting of hydrogen, a halogen, a linear or branched $C_{1-4}$ alkyl group, a linear or branched hydroxy $C_{1-4}$ alkyl group, a hydroxy group, —$NR^{11}R^{12}$, a linear or branched hydroxy $C_{1-4}$ alkylcarbonyl group, a heterocycloalkyl group, a hydroxy substituted heterocycloalkyl group, a linear or branched halo $C_{1-4}$ alkyl group, and a linear or branched $C_{1-4}$ alkoxy group,
$R^{11}$ and $R^{12}$ are each independently hydrogen, a linear or branched $C_{1-4}$ alkyl group, or a linear or branched hydroxy $C_{1-4}$ alkyl group,
$R^{15}$(s) are each independently a linear or branched $C_{1-4}$ alkyl group, a linear or branched hydroxy $C_{1-4}$ alkyl group, or a halogen,
p is an integer from 0 to 4, and
s and t are each independently an integer from 0 to 5, provided that $R^8$ is hydrogen, or an an integer from 0 to 4, provided that $R^8$ is not hydrogen.

9. The compound of claim 1, wherein
Y is a direct bond or —$CH_2$—,
Z is Formula 4 or Formula 5,
$R^8$ is hydrogen, a linear or branched $C_{1-4}$ alkyl group, a linear or branched hydroxy $C_{1-4}$ alkyl group, a heterocycloalkyl group, or a hydroxy substituted heterocycloalkyl group, and
$R^{15}$(s) are each independently a linear or branched $C_{1-4}$ alkyl group, a linear or branched hydroxy $C_{1-4}$ alkyl group, or a halogen.

10. A pharmaceutical composition comprising the compound according to claim 1.

11. A pharmaceutical composition comprising the compound according to claim 2.

12. A pharmaceutical composition comprising the compound according to claim 3.

13. A pharmaceutical composition comprising the compound according to claim 4.

14. A pharmaceutical composition comprising the compound according to claim 5.

15. A pharmaceutical composition comprising the compound according to claim 6.

16. A pharmaceutical composition comprising the compound according to claim 7.

17. A pharmaceutical composition comprising the compound according to claim 8.

18. A pharmaceutical composition comprising the compound according to claim 9.

* * * * *